US007718196B2

(12) United States Patent
Fowler et al.

(10) Patent No.: US 7,718,196 B2
(45) Date of Patent: May 18, 2010

(54) RAPAMYCIN-RESISTANT T CELLS AND THERAPEUTIC USES THEREOF

(75) Inventors: Daniel H. Fowler, Bethesda, MD (US); Unsu Jung, Ashburn, VA (US); Ronald E. Gress, Gaithersburg, MD (US); Bruce Levine, Cherry Hill, NJ (US); Carl June, Merion Station, PA (US)

(73) Assignees: The United States of America, as represented by the Department of Health and Human Services, Washington, DC (US); The Trustees of the University of Pennsylvania, Philadelphia, PA (US)

(*) Notice: Subject to any disclaimer, the term of this patent is extended or adjusted under 35 U.S.C. 154(b) by 6 days.

(21) Appl. No.: 11/298,313

(22) Filed: Dec. 9, 2005
(Under 37 CFR 1.47)

(65) Prior Publication Data
US 2006/0159667 A1 Jul. 20, 2006

Related U.S. Application Data

(63) Continuation-in-part of application No. PCT/US2004/018609, filed on Jun. 10, 2004, which is a continuation-in-part of application No. 10/481,913, filed as application No. PCT/US02/20415 on Jun. 26, 2002, now abandoned, application No. 11/298,313, which is a continuation-in-part of application No. 10/488,196, filed as application No. PCT/US02/27824 on Aug. 29, 2002, now abandoned, application No. 11/298,313, which is a continuation-in-part of application No. 10/494,540, filed as application No. PCT/US02/35240 on Oct. 31, 2002.

(60) Provisional application No. 60/478,736, filed on Jun. 12, 2003, provisional application No. 60/302,936, filed on Jul. 2, 2001, provisional application No. 60/316,854, filed on Aug. 31, 2001, provisional application No. 60/336,473, filed on Oct. 31, 2001.

(51) Int. Cl.
*A61K 35/28* (2006.01)
*C12N 5/08* (2006.01)
(52) U.S. Cl. .................... 424/578; 435/372.3
(58) Field of Classification Search ............. None
See application file for complete search history.

(56) References Cited

U.S. PATENT DOCUMENTS

| 5,624,823 A | 4/1997 | Sachs et al. |
| 5,747,034 A | 5/1998 | de Boer et al. |
| 5,756,085 A | 5/1998 | Sykes et al. |
| 5,770,197 A | 6/1998 | Linsley et al. |
| 5,858,358 A | 1/1999 | June et al. |
| 5,861,310 A | 1/1999 | Freeman et al. |
| 5,869,050 A | 2/1999 | de Boer et al. |
| 5,883,223 A | 3/1999 | Gray |
| 5,948,893 A | 9/1999 | June et al. |
| 5,958,403 A | 9/1999 | Storm et al. |
| 5,958,671 A | 9/1999 | Glimcher et al. |
| 6,001,973 A * | 12/1999 | Strom et al. ............ 530/351 |
| 6,063,772 A | 5/2000 | Tam |
| 6,129,916 A | 10/2000 | Chang |
| 6,150,337 A | 11/2000 | Tam |
| 6,231,893 B1 * | 5/2001 | Singhal ................ 424/577 |

FOREIGN PATENT DOCUMENTS

| WO | WO-90/05541 A1 | 5/1990 |
| WO | WO-94/28912 A1 | 12/1994 |
| WO | WO-95/33823 A1 | 12/1995 |
| WO | WO-98/33891 A1 | 8/1998 |
| WO | WO-98/47531 A2 | 10/1998 |
| WO | WO-99/24045 A1 | 5/1999 |
| WO | WO 03/004625 * | 1/2003 |
| WO | WO-03/038062 A2 | 5/2003 |

OTHER PUBLICATIONS

Ferraresso et al., Transplantation, 1993, vol. 55 pp. 888-894.*
Slavik et al., J of Immunology, 2001, pp. 3201-3209.*
Aarvak et al., "Change in the Th1/Th2 Phenotype of Memory T-Cell Clones from Rheumatoid Arthritis Synovium," Scand. J. Immunol. 50(1):1-9, 1999.
Assenmacher et al., "Commitment of Individual Th1-Like Lymphocytes to Expression of IFN-(Versus II-4 and IL-10: Selective Induction of IL-10 by Sequential Stimulation of Naive Th Cells with IL-12 and IL-4," J. Immunol. 161(6):2825-2832, 1998.

(Continued)

*Primary Examiner*—Michail A Belyavskyi
(74) *Attorney, Agent, or Firm*—Edwards Angell Palmer & Dodge LLP; Peter F. Corless; Christine C. O'Day

(57) ABSTRACT

Methods for generating highly enriched Th1/Tc1 and Th2/Tc2 functions are described. In particular, the generation of these functions are attained by the addition of an immune suppression drug, rapamycin or a rapamycin derivative compound. In addition to enhanced purity of T cell function, the T cells generated in rapamycin also express molecules that improve immune T cell function such as CD28 and CD62L. Such rapamycin generated functional T cell subsets may have application in the prevention or treatment of GVHD after allogeneic hematopoietic stem cell transplantation, the treatment of autoimmunity, or the therapy of infection or cancer.

17 Claims, 31 Drawing Sheets

OTHER PUBLICATIONS

Bradley et al., "The Cytokines Il-4, IFN-γ, and IL-12 Regulate the Development of Subsets of Memory Effector Helper T Cells In Vitro," J. Immunol. 155(4):1713-1723, 1995.

Brinkmann et al., "TCR-independent Activation of Human CD4+ 45RO' T Cells by Anti-CD28 plus IL-2: Induction of Clonal Expansion and Priming for a TH2 Phenotype," J. Immunol. 156(11):4100-4106, 1996.

Demeure et al, "In Vitro Maturation of Human Neonatal CD4 T Lymphocytes. II. Cytokines Present at Priming Modulate the Development of Lymphokine Production," J. Immuno. 152(10):4775-4782, 1994.

Fowler, et al., "Allospecific $CD4^+$, Th1/Th2 and $CD8^+$, Tc1/Tc2 Populations in Murine GVL:Type I Cells Generate GVL and Type II Cells Abrogate GVL," Biol. Blood Marrow Transplant. 2(3):118-125, 1996.

Fowler et al., "Donor CD4-Enriched Cells of Th2 Cytokine Phenotype Regulate Graft-Versus-Host Disease Without Impairing Allogeneic Engraftment in Sublethally Irradiated Mice," Blood 84(10):3540-3549, 1994.

Fowler et al., "Donor Lymphoid Cells of Th2 Cytokine Phenotype Reduce Lethal Graft Versus Host Disease and Facilitate Fully Allogenic Cell Transfers in Sublethally Irradiated Mice," Prog. Clin. Biol. Res. 389:533-540, 1994.

Fowler, et al., "Th2 and Tc2 Cells in the Regulation of GVHD, GVL, and Graft Rejection: Consideration for the Allogeneic Transplantation Therapy of Leukemia and Lymphoma," Leukemia and Lymphoma 38(3-4):221-234, 2000.

Garlie et al., "T Cells Coactivated with Immobilized Anti-CD3 and Anti-CD28 as Potential Immunotherapy for Cancer," J. Immunother. 22:336-345, 1999.

Gerosa, et al., "Interleukin-12 Primes Human CD4 and CD8 T Cell Clones for High Production of Both Interferon-Gamma and Interleukin-10," J. Exp. Med. 183(6):2559-2569, 1996.

Hu-Li et al., "In differentiated $CD4^+$ T Cells, Interleukin 4 Production is Cytokine-Autonomous, Whereas Interferon Production is Cytokine-Dependent." Proc. Natl. Acad. Sci. USA 94:3189-3194, 1997.

Kane et al., "Akt Provides the CD28 Costimulatory Signal for Up-Regulation of IL-2 and IFN-(but not $T_H2$ Cytokines," Nature Immunol. 2(1):37-44, 2001.

Keralavarma et al., "Improved 'Suicide' Retroviral Vector Containing Mutant HSV-TK Gene Confers Increased Sensitivity to Gancyclovir," Blood 94(supp. 12):329b, 1999.

Levine et al., "Effects of CD28 Costimulation on Long-Term Proliferation of $CD4^+$ Cells in the Absence of Exogenous Feeder Cells," J. Immunol. 159(12):5921-5930, 1997.

Levine et al., "Large-Scale Produciton of CD4+ T Cells from HIV-1-Infected Donors After CD3/CD28 Costimulation," J. Hematother. 7:437-448, 1998.

Lovett-Racke et al., "Decreased Dependence of Myelin Basic Protein-Reactive T Cells on CD28-Mediated Costimulation in Multiple Sclerosis Patients," J. Clin. Invest. 101(4):725-730, 1998.

Lum, et al., "Immune Modulation in Cancer Patients After Adoptive Transfer of Anti-CD3/Anti-CD28—Costimulated T Cell—Phase 1 Clinical Trial," J. Immunother. 24:408-419, 2001.

Nakamura et al., "Polarization of IL-4- and IFN-Gamma-Producing CD4+ T Cells following Activation of Naive CD4-T Cells," J. Immunol. 158(3):1085-1094, 1997.

Noble, et al., "Early Th1/Th2 Cell Polarization in the Absence of IL-4 and IL-12: T Cell Receptor Signaling Regulates the Response to Cytokines in CD4 and CD8 T Cells," Eur. J. Immunol. 31:2227-2235, 2001.

Ohta et al.. "Manipulation of Th1/Th2 Balance in Vivo by Adoptive Transfer of Antigen-Specific Thi and Th2 Cells," J. Immunological Methods 209:85-92, 1997.

Palm et al., "Co-Development of Naive $CD4^+$ Cells Towards T Helper Type or T Helper Type 2 Cells Induced by a Combination of IL-12 and IL-4," Immunogiol. 196:475-484, 1996/97.

Parada et al., "Synergistic Activation of $CD4^+$ T Cells by IL-16 and IL-2," J. Immunol. 160:2115-2120,1998.

Petrus et al., "An Immunoablative Regimen of Fludarabine and Cyclophosphamide Prevents Fully MHC-Mismatched Murine Marrow Graft Rejection Independent of GVHD," Biol. Blood Marrow Transplant 6(2A):182-189, 2000.

Riley, et al., "Naive and Memory CD4 T Cells Differ in Their Susceptibilities to Human Immunodeficiency Virus Type 1 Infection following CD28 Costimulation: Implications for Transmission and Pathogenesis," J. Virol. 72(10):8273-8280, 1998.

Sad, et al., "Cytokine-Induced Differentiation of Precursor Mouse CD8+ T Cells into Cytotoxic CD8+ T Cells Secreting Th1 or Th2 Cytokines," Immunity 2(3):271-279, 1994.

Sad, et al., "Single IL-2-Secreting Precursor CD4 T Cell can Develop Into Either Th1 or Th2 Cytokine Secretion Phenotype," J. Immuno. 153(8):3514-3522, 1999.

Schmitt et al., "Differential Effects of Interleukin-12 on the Development of Naive Mouse $CD4^+$ T Cells," Eur. J. Immunol. 24:343-347, 1994.

Seder, et al., "High-Dose IL-2 and IL-15 Enhance the in Vitro Priming of Naive CD4+ T Cells for IFN-Gamma but have Differential Effects on Priming for IL-4," J. Immunol. 156(7):2413-2422, 1996.

Skea, et al., "The Selective Expansion of Functional T Cell Subsets," J. Hematother. Stem Cell Res. 8(5):525-538, 1999.

Sornasse et al., "Differentiation and Stability of T Helper 1 and 2 Cells Derived from Naive Human Neonatal $CD4^+$ T Cells, Analyzed at the Single-Cell Level," J. Exp. Med. 184:473-483, 1996.

Syme, et al. "Effects of Cytokines on the Culture and Differentiation of Dentritic Cells in Vitro," J. Hematother. Stem Cel Res. 10:43-51, 2001.

Powell, J.D. et al, Inhibition of Cell Cycle Progression by Rapamycin Induces T Cell Clonal Anergy Even in the Presnece of Costimulation, The Journal of Immunology, 1999, 162: 2775-2784.

Erard et al. "Presence or Absence of TGF-β Determines IL-4-Induced Generation of Type 1 or Type 2 CD8 T Cell Subsets" The Journal of Immunology, 1999, 162:: 209-214.

Fowler et al. "CD8+ T Cells of Tc2 Phenotype Mediate a GVL Effect and Prevent Marrow Rejection" Vox Sanguinis 1998; 74 (Suppl. 2): 331-340.

Fowler et al. "Non-Host-Reacive Donor CD8+ T Cells of Tc2 Phenotype Potently Inhibit Marrow Graft Rejection" Blood, vol. 91, No. 11 (Jun. 1), 1998: pp. 4045-4050.

Fowler et al. "Donor Lymphoid Cells of Th2 Cytokine Phenotype Reduced Lethal Graft Versus Host Disease and Facilitate Fully Allogeneic Cell Transfers in Sublethally Irradiated Mice" Advances in Bone Marrow Purging and Processing: Fourth International Symposium, pp. 533-540, 1994.

Fowler et al. "Allospecific $CD8^+$ Tc1 and Tc2 Population sin Graft-Versus-Leukemia Effect and Graft-Versus-Host Disease" The Journal of Immunology, 1996, 157: 4811-4821.

Halverson et al. "In Vitro Generation of Allospecific Human CD8+ T Cells of Tc1 and Tc2 Phenotype" Blood, vol. 90, No. 5 (Sep. 1), 1997: pp. 2089-2096.

Lamouse-Smith et al. "Cytokine Requirements for Production of a Novel Anti-CD8-Resistant CTL Population" The Journal of Immunology, 1999, 163: 4160-4167.

Levine et al. "Large-Scale Productio of CD4+ T Cells from HIV-1-Infected Donors After CD3/CD28 Costimulation" Journal of Hematotherapy 7: 437-448 (1998).

Levine et al. "Antiviral Effect and Ex Vivo $CD4^+$ T Cell Proliferation in HIV-Position Patients as a Result of CD28 Costimulation" Science, vol. 272, Jun. 20, 1996.

Mackall et al. "Distinctions Between $CD8^+$ and $CD4^+$ T-Cell Regenerative Paathways Result in Prolonged T-Cell Subset Imbalanced After Intensive Chemotherapy" Blood, vol. 89, No. 10 (May 15), 1997: pp. 3700-3707.

McAdam et al. "Mouse Inducible Costimulatory Molecule (ICOS) Expression Is Enhanced by CD28 Costimulation and Regulates Differentiation of $CD4^+$ T Cells" The Jouranl of Immunology, 2000, 165: 5035-5040.

Medin et al. "Selection of Retrovirally Transduced Cells to Enhanced the Efficency of Gene Therapy" Proceedings of the Association of American Physicians, vol. 109, No. 2, pp. 111-119.

Mosmann et al. "Differentiation and Functions of TCell Subsets" 1997 The molecular basis of cellular defence mechanisms. Wiley, Chichester (Giba Foundation Symposium 204) p. 148-158.

Sad et al. "Interleukin (IL) 4, in the Absence of Antigen Stimulation, Induces and Anenergy-like State in Differentiated $CD8^+$ TC1 Cells: Loss of IL-2 Synthesis and Autonomouse Proliferation but Retention of Cytotoxicity and Synthesis of Other Cytokines" J. Exp. Med. vol. 182 Nov. 1995 1505-1515.

Schafer et al. "p38∝ Mitogen-Activated Protein Kinase Is Activated by CD28-Mediated Signaling and Is Required for IL-4 Production by Human $CD4^+$ $CD45RO^+$ T Cells and Th2 Effector Cells" The Journal of Immunology, 1999, 162: 7110-7119.

Szmania et al. "Isolation and Expansion of Cytomegalovirus-Specific Cytotoxic T Lymphocytes to Clinical Scale From a Single Blood Draw Using Dendritic Cells and HLA-tetramers" Blood, 2001: 98: 505-512.

Thomas et al. "T Cytotoxic 1 and T Cytotoxic 2 CD8 T Cells Both Inhibit IgE Responses" Int Arch Allergy Immunol 2001; 124: 187-189.

Vinay et al. "Differential Expression and Costimulatory Effect of 4-1BB (CD137) and CD28 Molecules on Cytokine-Induced Murine $CD8^+$ Tc1 and Tc2 Cells" Cellular Immunology 192, 63-71 (1999).

Vukmanovic-Stejic et al. "Human Tc1 and Tc2/Tc0 CD8 T-cell Clones DIsplay Distinct Cell Surface and Functional Phenotypes" Blood, 2000; 95: 231-240.

Witzke et al. "Supression Mediated by Anergic $CD4^+$ T Cells Requires Stimulation by MHC-Peptide Complexes and Can be Induced in the Presence of Costimulation" Transplantation, vol. 72, 369-376, No. 3, Aug. 15, 2001.

Zhang et al. "Intracellular Cytokine Profile of T Cells from Childresn With Acute Lymphoblastic Leukemia" Cancer Immunol Immunother (2000) 49: 165-172.

Laport et al. "Adoptive Transfer of CD3/CD28 Ex Vivo Costimulated T Cells in Patients with Relapsed/Refractory Non-Hodgkin's Lymphoma (NHL) Following High Dose Chemotherapy (HDC) With CD34-Selected Peripheral Blood Stem Cell (PBSC) Support" Abstract# 1751, Clinical BMT: Mached Related Donor: II, p. 407a.

Lee et al. "Allogeneic Bone Marrow Transplantation With T Cell Depletion (TCD) and Prophylactic T Cell Reinfusion (PTR) for Patients With High-Risk Lymphoma" Clinical BMT: Matched Related Donor: II, Abstract#1754, p. 407a.

* cited by examiner

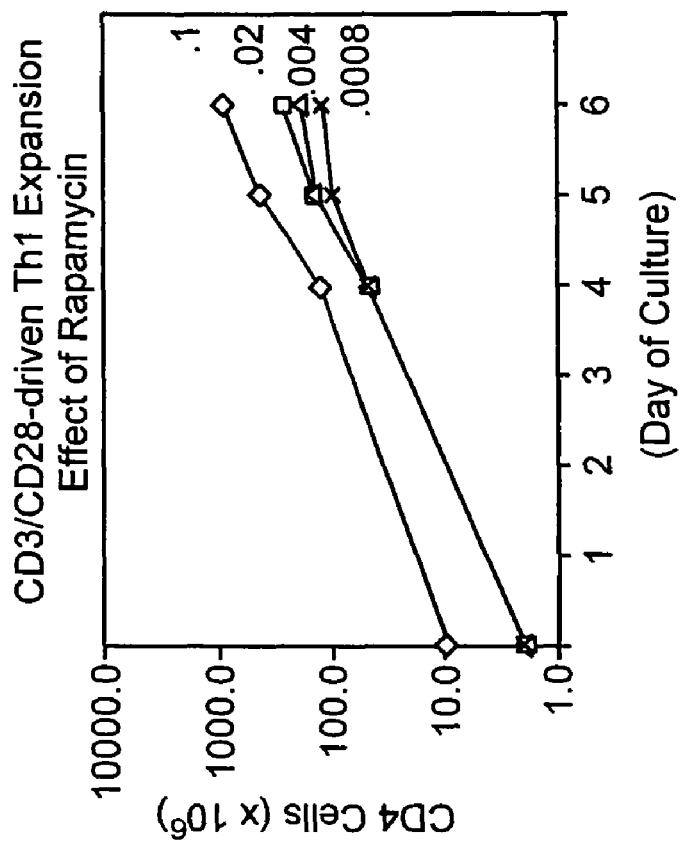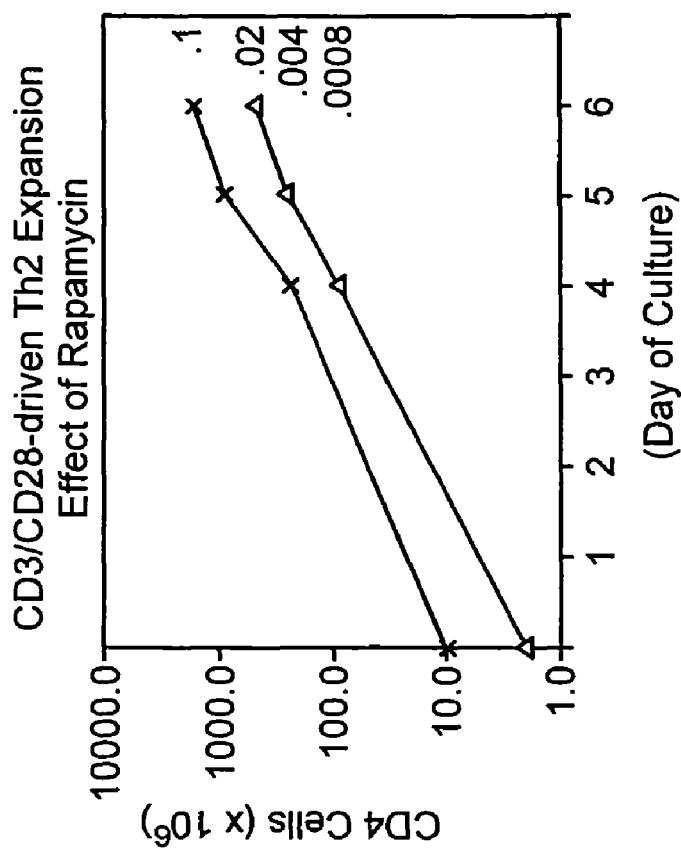
FIG. 4

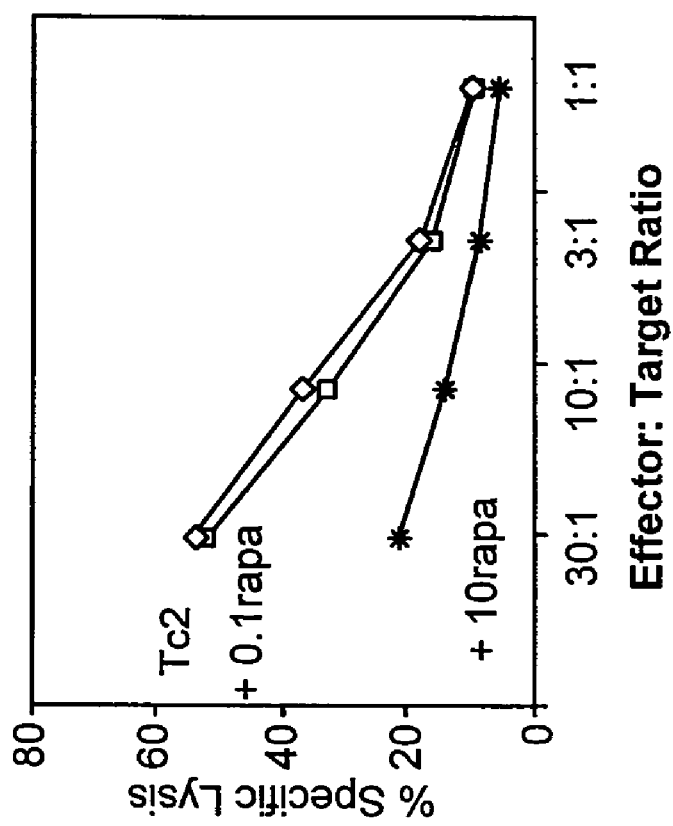
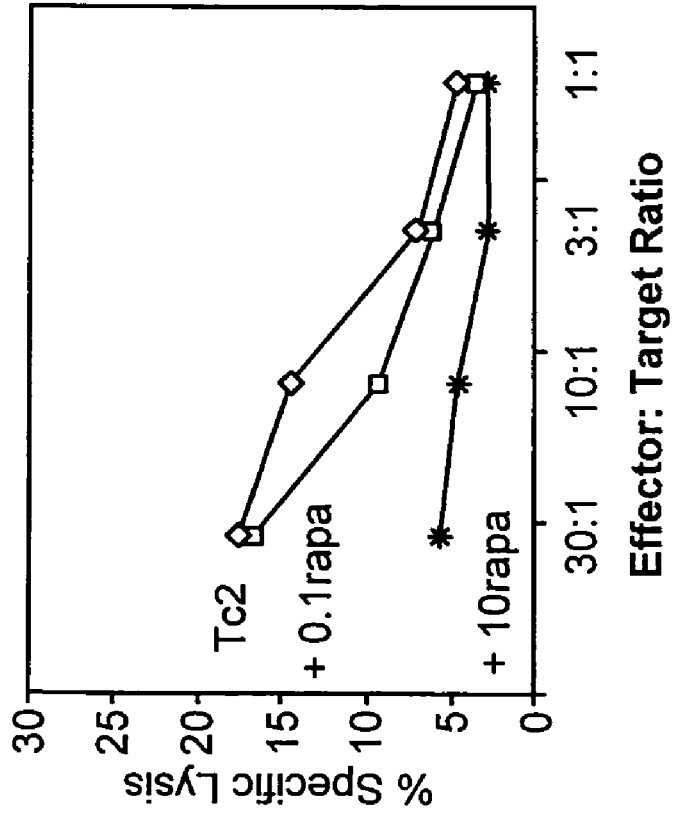
FIG. 16

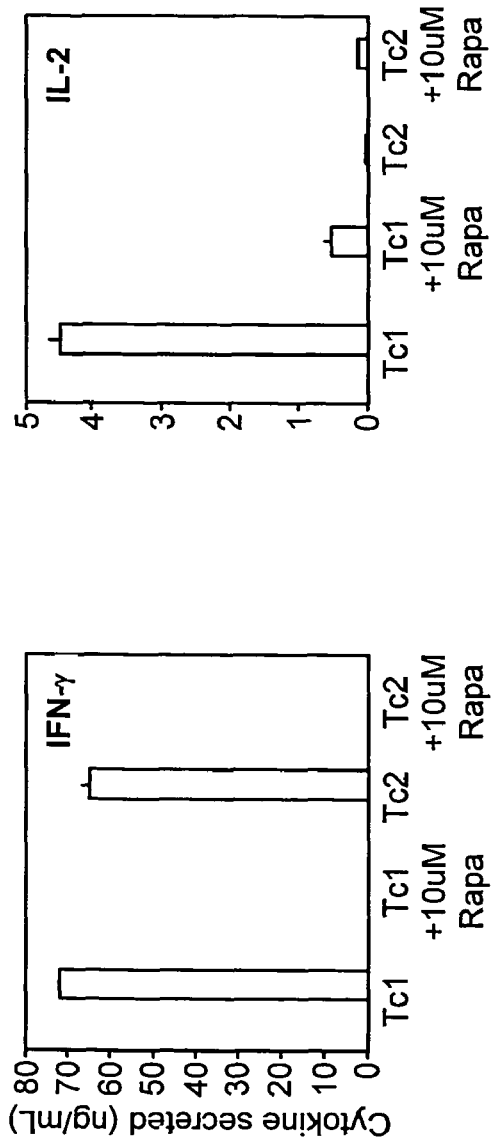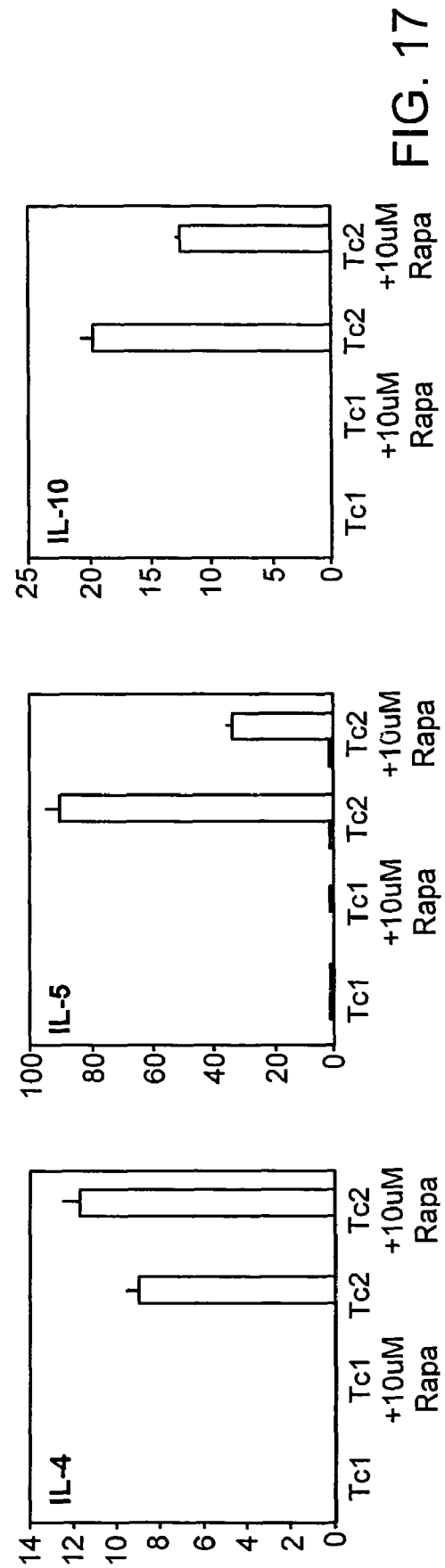
FIG. 17

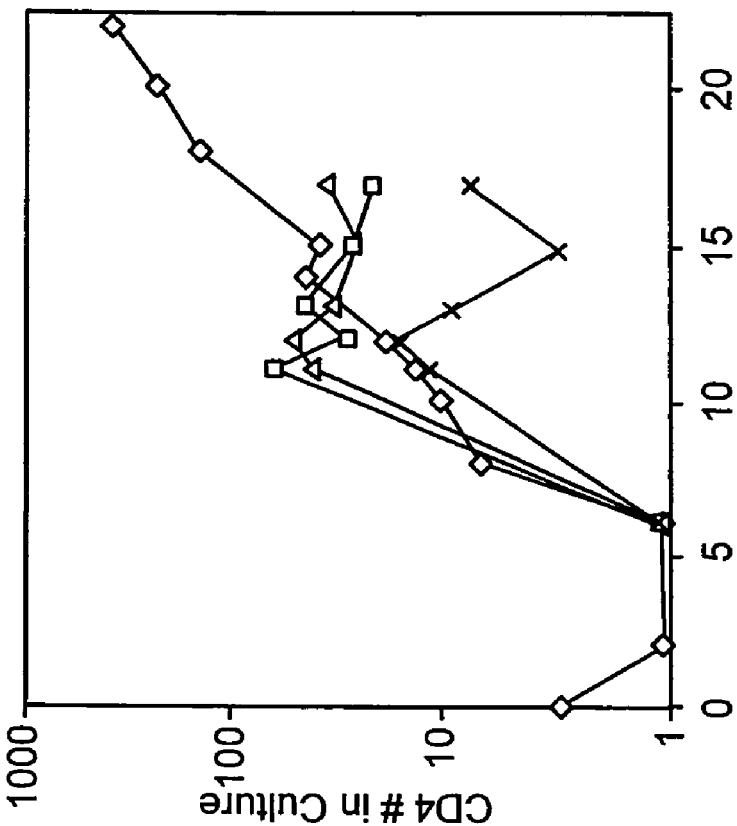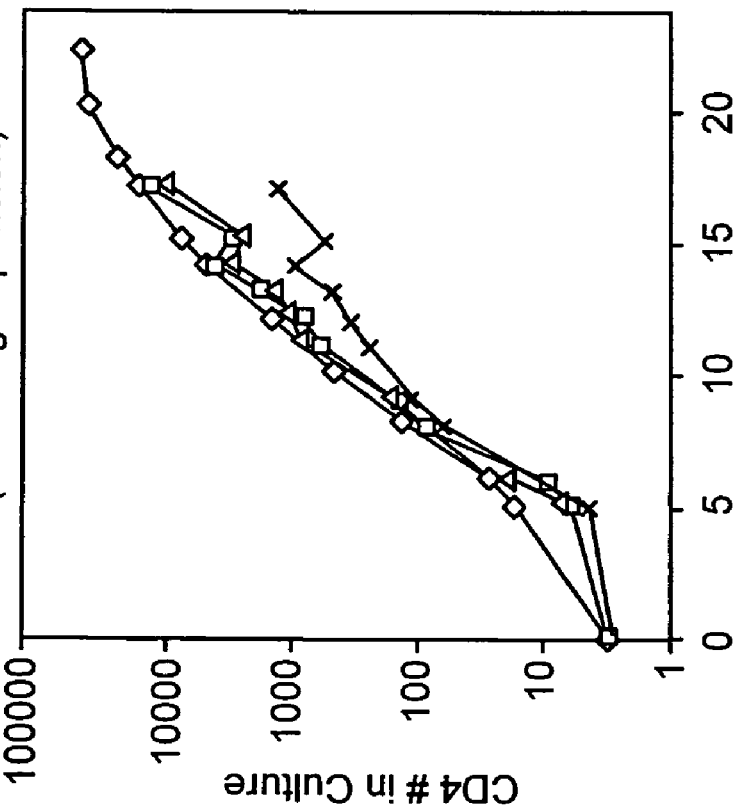
FIG. 23

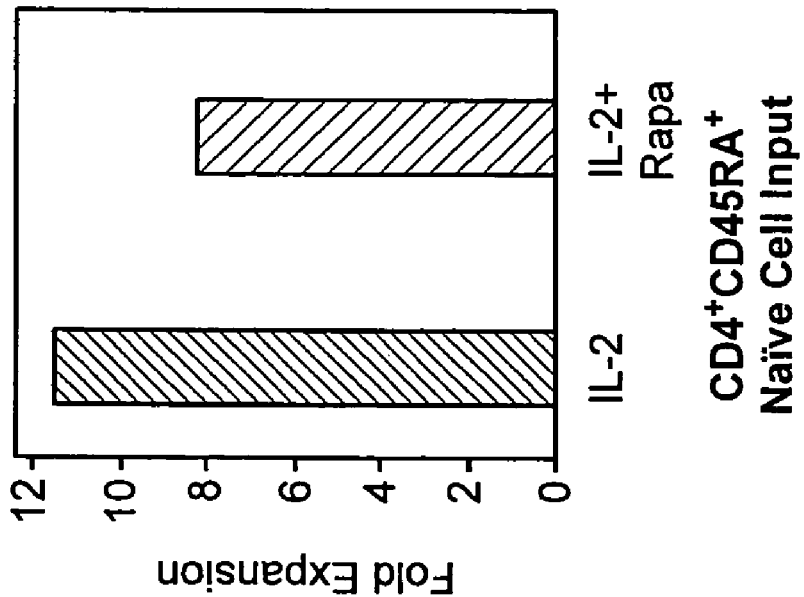
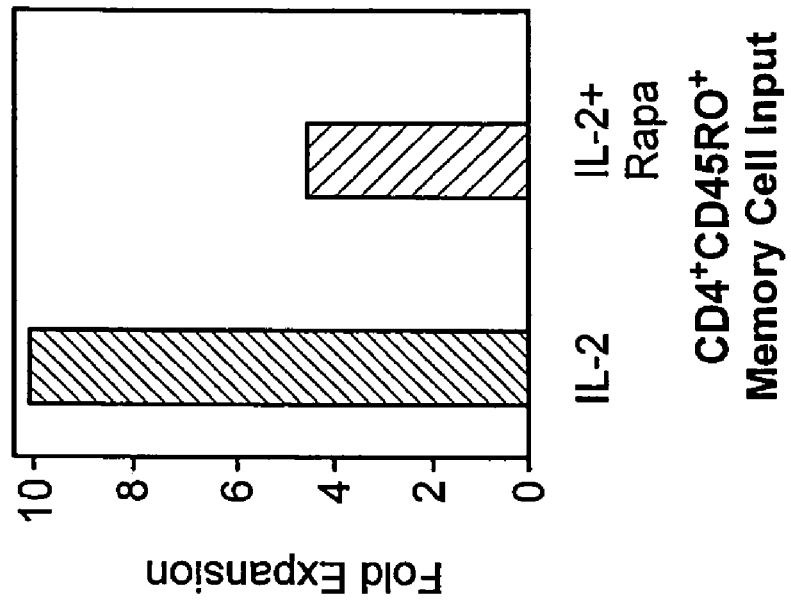
FIG. 31

RAPAMYCIN-RESISTANT T CELLS AND THERAPEUTIC USES THEREOF

CROSS-REFERENCE TO RELATED APPLICATIONS

The present application is the 35 U.S.C. §111 continuation-in-part of PCT Application No. PCT/US2004/018609, which was filed on Jun. 10, 2004, currently pending, which claims the benefit of U.S. Provisional Application No. 60/478,736, which was filed on Jun. 12, 2003; in addition this application is a continuation-in-part of each of the following: i) pending U.S. patent application Ser. No. 10/481,913, which is a continuation of PCT Application No. PCT/US02/20415, which was filed on Jun. 26, 2002, and which claims the benefit of U.S. Provisional Application No. 60/302,936, which was filed on Jul. 2, 2001; ii) pending U.S. patent application Ser. No. 10/488,196, which is a continuation of PCT/US02/27824, which was filed on Aug. 29, 2002, and which claims the benefit of U.S. Provisional Application No. 60/316,854, which was filed on Aug. 31, 2001; and iii) pending U.S. patent application Ser. No. 10/494,540, which is a continuation of PCT/US02/35240, which was filed on Oct. 31, 2002, which claims the benefit of U.S. Provisional Application No. 60/336,473, which was filed on Oct. 31, 2001; each of the aforementioned patent applications is hereby incorporated by reference in its entirety.

FIELD OF THE INVENTION

T cell-based therapies for treatment of medical conditions such as cancer, disease due to infectious disease organisms such as viruses, autoimmune diseases and Graft Versus Host Disease ("GVHD") are provided. In particular, enriched populations selected for Th1, Th2, Tc1 or Tc2 functions are selected for and controlled when administered to a patient in vivo.

BACKGROUND OF THE INVENTION

Ongoing advances in solid organ and hematopoietic stem cell transplantation (HSCT), including new immunosuppressive agents and improvements in histocompatibility matching, organ procurement, and surgical techniques, are gradually improving the outcome of clinical transplantation (Hariharan et al, 2000. *N. Engl. J. Med.* 342:605-12). However, chronic allograft rejection remains the prime determinant of long-term graft survival (Paul. L. C., 1999, *Kidney International* 56:783-793). Furthermore, stem cell graft rejection typically limits the application of allogeneic HSCT to those patients having an HLA-matched sibling donor, which represents a minority of all patients that might benefit from allogeneic HSCT therapy.

Tissue transplantation between genetically non-identical individuals results in immunological rejection of the tissue through T cell-dependent mechanisms. To prevent allograft rejection, immunosuppressive agents such as calcineurin phosphatase inhibitors and glucocorticosteroids which directly or indirectly interfere with IL-2 signaling are administered to transplant recipients (see, e.g., Morris, P. J., 1991, *Curr. Opin. Immunol.* 3:748-751; Sigal et al., 1992, *Ann. Rev. Immunol.* 10:519-560; and L'Azou et al., 1999, *Arch. Toxicol.* 73:337-345). The most commonly used immunosuppressive agents today are the calcineurin inhibitors cyclosporin A and FK506, which act relatively indiscriminately by impairing T cell receptor ("TCR") signal transduction. A third primary immune suppression drug, rapamycin, which has recently received FDA approval for prevention of organ transplant rejection, acts through a distinct mechanism of inhibition of the protein mammalian target of rapamycin (mTOR). The biological effect of these three immunosuppressive agents is short-lasting, and as such, transplant recipients normally require life-long treatment of immunosuppressive agents to prevent transplant rejection. As a result of the long-term non-specific immunosuppression, these immunosuppressive agents have many serious adverse effects. For example, the administration of cyclosporin A or FK506 to a transplant recipient results in degenerative changes in renal tubules. Transplant recipients receiving long-term immunosuppressive treatment have a high risk of developing infections and tumors. For example, patients receiving immunotherapy are at higher risk of developing lymphomas, skin tumors and brain tumors (see, e.g., Fellstrom et al., 1993, *Immunol. Rev.* 134:83-98).

In addition to graft rejection, immune T cells also mediate the primary cause of lethality after allogeneic HSCT, graft-versus-host disease (GVHD). GVHD, which is primarily initiated by donor $CD4^+$ T cells expressing a Th1 cytokine phenotype characterized by IL-2 and IFN-γ secretion, manifests clinically as damage to the skin, intestine, liver, and immune system. To reduce the incidence and severity of GVHD, immune suppression therapy involving either cyclosporin A or FK506 is typically administered, often in combination with other immune suppression agents such as methotrexate. This immune suppression approach to the prevention of GVHD is problematic, as significant morbidity and mortality from GVHD still occurs, and the immune suppression therapy reduces the potency of the allogeneic T cell-mediated graft-versus-leukemia (GVL) or graft-versus-tumor (GVT) effect, and predisposes to multiple viral, bacterial, and fungal infections.

An alternative to immunosuppressive agents for the prevention of allograft rejection is the blockage of specific receptors involved in T cell costimulation. T cell activation requires both TCR-mediated signal transduction and simultaneously delivered costimulatory signals. These costimulatory signals are contributed, in part, by the activation of the costimulatory molecule CD28, which is expressed on resting T cells, by CD80 (B7-1) or CD86 (B7-2) expressed on antigen presenting cells ("APCs"). The activation of the costimulatory molecule CD40, which is expressed on APCs (i.e., B cells, dendritic cells, and macrophages), by CD40 ligand ("CD40L"), which is expressed on activated T cells, contributes to the upregulation of T cell activation by inducing the expression of B7-1 and B7-2 on APCs and the production of certain chemokines and cytokines such as IL-8, MIP-1-α, TNF-α, and IL-12 (Cella et al., 1996, *J. Exp. Med.* 184:747-752: and Caux et al., 1994, *J. Exp. Med.* 180:1263-1272). The CD40/CD40L interaction also results in the differentiation of T cells to T helper ("Th") type 1 cells in part due to the expression of cytokines such as IL-12 by dendritic cells and macrophages.

CTLA-4 is normally expressed as a membrane-bound receptor on T cells and, similar to CD28, binds to B7-1 and B7-2 molecules on APCs; however, signaling of T cells via CTLA-4 downregulates T cells. The administration of soluble CTLA-4Ig is believed to prevent allograft rejection by competing with CD28 for B7-1 and B7-2. Soluble CTLA-4Ig has been administered to transplant recipients to disrupt the CD28/B7 interaction so that T cell costimulation is blocked and allograft rejection does not occur (Zheng et al., 1999, *J. Immunol.* 162:4983-4990; Lenschow et al., 1996, *Ann. Rev. Immunol.* 14:233-258). Unfortunately, CTLA-4Ig has variable efficacy, and typically does not prevent development of chronic rejection.

Anti-CD40L (anti-CD154) monoclonal antibodies have also been administered to transplant recipients to prevent allogaft rejection. These antibodies function by blocking the interaction of CD40 on antigen presenting cells (APC) and CD40L on activated T cells. It has recently been shown that graft survival achieved through the use of anti-CD40L monoclonal antibodies results in a significant inhibition of Th1 type cytokines (i.e., IL-2, IL-12; TNF-α, and IFN-α), and an increase in the levels of the Th2 type cytokines (i.e., IL-4, and IL-10) in the graft sections (Hancock et al., 1996, *Proc. Natl. Acad. Sci. USA* 93:13967-13972). Although the administration of anti-CD40L monoclonal antibodies has been shown to result in permanent graft survival when given to mice in combination with donor-specific spleen cells, adverse side effects such as coagulation have also been shown to be associated with the administration of anti-CD40L monoclonal antibodies. Initial clinical trials in adult renal transplant recipients receiving anti-CD40L monoclonal antibody plus glucocorticoids were halted because of thromboembolic complications though the extent to which thromboembolism was attributable to monoclonal antibodies versus non-specific factors in the antibody formulation is unclear (Kawai et al., 2000, *Nature Med.* 6:114; and Kirk et al., 2000, *Nature Med.* 6:114). Further, in the primate renal allograft study, concomitant use of mainstream immunosuppressive agents such as FK-506, methylprednisolone and mycophenolate mofetil diminished the efficacy of CD40L (CD154) mAb, though the exact contribution of each of the individual drugs to this reduction in efficacy was not determined (Kirk, A. D., 1999, *Nature Medicine* 5:686-693.).

Immunocompromised patients lack a fully active and effective immune system, and are vulnerable to infection by a host of opportunistic organisms that are effectively controlled in a healthy individual. Cancer patients and transplant recipients are especially vulnerable to these infections since their therapeutic regimen often includes radiation and chemotherapeutic agents, which compromise the immune system. Immunodeficient patients, such as AIDS and SCID patients, are also at high risk from these opportunistic pathogens. In particular, patients undergoing bone marrow transplantation (BMT) are severely immunocompromised until their immune systems reconstitute. During the period prior to reconstitution, these patients are susceptible to serious, and sometimes fatal, virus infections caused by normally benign viruses such as adenovirus, cytomegalovirus (CMV), and Epstein-Barr virus (EBV).

In a normal individual, recognition and destruction of virally infected cells is performed principally by $CD8^+$ cytotoxic T lymphocytes (CTLs). The mounting of a CTL immune response requires that the viral proteins undergo intracellular processing to peptide fragments. Selected peptides of defined length are subsequently presented at the cell surface in conjunction with MHC class I molecules. This complex provides the first stimulatory signal recognized by the specific cytotoxic T lymphocyte.

Processing of antigens for presentation by class I MHC involves a complex cellular process (Berzofsky and Berkower, Fundamental Immunology, Third Edition, Paul (ed.), Raven Press, Ltd.: New York, pp. 258-259 (1993). Unlike processing of exogenous antigen via endosomal pathways for presentation by class II MHC, antigen presented by class I MHC generally must be synthesized endogenously and processed by a nonendosomal pathway into peptides. However, exogenous antigens can enter the cytoplasm for processing by the nonendosomal pathway and presentation by class I MHC.

No satisfactory methods presently exist for monitoring whether a transplant graft is being accepted or rejected by a recipient. In general, signs of cellular damage within the transplant tissue can be assayed. Alternatively, for tissues such as kidney or liver, physiological function of the transplant tissue can be assayed. Often, however, by the time overt signs of either cellular damage or a decrease in physiological function are detected, the tissue graft is already beyond rescue. This is particularly true in the case of such organ transplants as heart transplants, with which the first overt signs of rejection are often complete failure of the heart's function. Similarly, in the setting of allogeneic HSCT, there exist no reliable method to detect GVHD prior to the onset of significant end-organ impairment; oftentimes, when GVHD does develop, the donor immune reaction is relatively mature, and can thereby be refractory to even the most potent immune suppression therapies available.

Accordingly, there is a need for improved, safer immunomodulatory treatments that have long-lasting effects for the prevention of transplant rejection or GVHD. In particular, there is a need for treatments that are more specific and less toxic than the currently available therapeutic agents.

In addition to graft rejection and GVHD, immune T cells of autologous or allogeneic source may play a beneficial role in mediating anti-tumor effects and anti-infectious disease effects, including against viral, bacterial, and fungal processes. This T cell biology offers the possibility that adoptive transfer of ex vivo generated T cell populations might be utilized in the therapy of cancer or infection. However, full realization of this possibility is limited by a general inability to amplify a potent autologous immune response against cancer or infectious disease antigens in vivo. Furthermore, immune T cell therapy in the allogeneic setting is limited by allogeneic T cell attack against normal host tissues, which is manifested as GVHD. In the allogeneic anti-tumor immune therapy setting, the graft-versus-leukemia (GVL) or graft-versus-tumor (GVT) effect is reduced by the immune suppression drugs cyclosporine A, FK506, corticosteroids, and methotrexate that are utilized to prevent or treat GVHD. Avoidance of standard GVHD prevention or treatment agents through rapamycin administration post-transplant will predictably facilitate improved GVL and GVT effects, resulting in improved rates of cancer cure.

SUMMARY OF THE INVENTION

We have now found methods and systems for generating highly enriched Th1/Tc1 and Th2/Tc2 functions in a subject. These methods and systems allow for the preferential selection of either Th1/Tc1 or Th2/Th2 functions, administration of the selected functions to a patient and subsequent control of these functions once administered.

More particularly, we have shown that the generation of these functions are attained by the addition of an immune suppression drug, rapamycin. In addition to enhanced purity of T cell function, the T cells generated in rapamycin also express molecules that improve immune T cell function such as CD28 and CD62L.

In a preferred embodiment, the invention provides a method for selecting and expanding enriched T cell subsets, comprising co-stimulating isolated T lymphocytes in vitro by adding cytokines for selecting a T cell subset followed by expansion of the T cell subset in the presence of rapamycin or a rapamycin derivative compound.

In another preferred embodiment, the subset of T cells is selected by culturing T cell subsets with cytokines. Preferably, a Th1/Tc1 subset of T lymphocytes is selected by culturing the lymphocytes in the presence of IL-12, and a Th2/Tc2 subset of T lymphocytes can be preferably generated by addition of IL-4.

Preferably, the T lymphocytes are co-stimulated. The co-stimulation of T lymphocytes suitably comprises initiating one or more intracellular signaling events. For instance, the intracellular signaling events can be initiated by culturing the T lymphocytes with one or more antibodies, polypeptides, polynucleotides, small molecules, or combinations thereof. Alternatively, the intracellular signaling events are initiated by solid phase anti-CD3 and anti-CD28 antibodies binding to their respective ligands.

In a preferred embodiment, a subset of T lymphocytes is selected based on the disease to be treated. Preferably, the T lymphocytes are cultured with cytokines and rapamycin to select for either a Th1/Tc1 or Th2/Tc2 subset. The desired subset is expanded and re-infused into a patient suffering from or susceptible to a disease. Preferably the T lymphocytes are autologous lymphocytes from a patient, and/or they can be derived from an allogeneic donor, which may represent an HLA-matched sibling donor, an HLA-matched donor from a non-family member, or a partially matched family member, such as a haplo-identical donor (parent or child). For instance, a patient to be treated is suffering from, or is susceptible to, cancer or infectious disease organisms, such as a virus. The preferred rapamycin resistant subset of lymphocytes that are infused into the patient are the Th1/Tc1 subset.

In another preferred embodiment, the patient to be treated is suffering from, or is susceptible to graft-versus-host-disease (GVHD). In this instance, in which a patient with cancer is to receive an allogeneic HSCT, the donor T cells of preference would be rapamycin resistant T cells of Th2/Tc2 phenotype, which are typically associated with reduced GVHD. As such, T cells from the donor would be harvested prior to transplantation, in vitro expanded in rapamycin or a rapamycin derivative compound to generate a Th2/Tc2 phenotype, and subsequently administered in the setting of the allogeneic HSCT to allow for a beneficial allogeneic T cell effect, such as the mediation of GVL or GVT effects, or the prevention of stem cell graft rejection, with reduced GVHD.

In another preferred embodiment, the selected T cell subsets are preferably cultured in at least about 0.01 µM rapamycin or a rapamycin derivative compound, more preferably the T cell subsets are cultured in at least about 0.1 µM rapamycin or a rapamycin derivative compound, most preferably the T cell subsets are cultured in at least about or up to 1.0 µM, 2.0 µM, 4.0 µM, 6.0 µM, or 10.0 µM rapamycin or a rapamycin derivative compound. It is preferred that the rapamycin resistant T cell subset populations express surface markers such as CD28, and preferably CD62L.

In another preferred embodiment, methods for preventing and/or treating GVHD in a mammal, comprise, harvesting allogeneic cells from the transplant donor, selecting for a subset of rapamycin resistant CD4$^+$ T cells and CD8$^+$ T cells in vitro; and, administering to the mammal rapamycin resistant T cells concomitantly with rapamycin. The subset of rapamycin resistant T cells that are administered to a mammal is a Th2/Tc2 subset. Preferably, the rapamycin resistant Th2 cell subset express CD4 and the Tc2 cell subset express CD8. Most preferably, the rapamycin resistant Th2/Tc2 cells express CD62L and secrete cytokines, preferably type II cytokines. References to rapamycin resistant T cells in inclusive of T cells that are resistant to rapamycin or a rapamycin derivative compound. Typically, T cells that are resistant to rapamycin or a rapamycin derivative compound also will be resistant to rapamycin.

In another preferred embodiment, rapamycin or a rapamycin derivative compound is co-administered with rapamycin resistant T cells to a mammal in need of therapy. The dosage of rapamycin or a rapamycin derivative compound to be administered to the mammal will be tailored to each recipient based on serum monitoring of rapamycin drug levels. Because of the in vitro generation, rapamycin exposed T cells will have a selective advantage in such an in vivo state, the achievement of rapamycin levels at the higher side of the therapeutic range is desirable. Preferably, rapamycin and any derivative, salt, ethers and the like can be used.

In another aspect, the invention provides methods for treating a patient suffering from or susceptible to cancer, comprises, harvesting autologous cells from the mammal; selecting for a subset of rapamycin resistant CD4$^+$ T cells and CD8$^+$ T cells in vitro; and, administering to the mammal rapamycin resistant T cells concomitantly with rapamycin or a rapamycin derivative compound. The subset of rapamycin resistant T cells for treating a patient suffering from or susceptible to cancer, is preferably a Th1/Tc1 subset and the Th1/Tc1 subset expresses CD62L. Preferably, the Th1 cells express CD4 and the Tc1 cells express CD8. Preferably, the rapamycin resistant Th1/Tc1 cellular subset secretes type I cytokines.

In a further aspect, the invention provides a use of T cells as disclosed herein for the treatment of a targeted disease or disorder, including for the treatment of undesired cell proliferation including cancer, infectious diseases, reduction of graft versus host disease (GVHD) and the like.

In a yet further aspect, the invention provides a use for the preparation of a therapeutic composition of T cells as disclosed herein for treatment of a targeted disease or disorder, including for the treatment of undesired cell proliferation including cancer, infectious diseases, reduction of graft versus host disease (GVHD) and the like.

Preferred methods of the invention including identifying and/or selecting a subject (e.g. a mammal, particularly a human) that is susceptible to or suffering from a condition as disclosed herein such as cancer, an infectious diseases, reduction of graft versus host disease (GVHD) and the like; and thereafter administering to the identified and selected subject a T cell composition as disclosed herein.

The invention also includes pharmaceutical compositions that comprise rapamycin resistant T cells optionally admixed with a pharmaceutically acceptable carrier and optionally packaged together with instructions (e.g. written) for use of the composition for a condition as disclosed herein.

The invention also includes rapamycin resistant T cells, e.g. as may be obtainable as disclosed herein such as by treating a sample of isolated T cells (mammalian, preferably human) with rapamycin or a rapamycin derivative compound and selecting a subset of rapamycin resistant T cells particularly rapamycin resistant CD4$^+$ T cells and/or CD8$^+$ T cells, typically in vitro.

Other aspects of the invention are discussed infra.

DEFINITIONS

The following definitions are provided:

As used herein, the singular forms "a", "an" and "the" include plural referents unless the context clearly dictates otherwise.

As used herein, the term "infectious agent" refers to an organism wherein growth/multiplication leads to pathogenic events in humans or animals. Examples of such agents are: bacteria, fungi, protozoa and viruses.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head and neck, kidney, lung, non-small cell lung, melanoma, mesothelioma, ovary, sarcoma, stomach, uterus and Medulloblastoma. The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic). Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Examples of sarcomas which can be treated with the compositions disclosed herein, and optionally a potentiator and/or chemotherapeutic agent include, but not limited to a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the compositions disclosed herein, and optionally a potentiator and/or another chemotherapeutic agent include but not limited to, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the compositions disclosed herein, and optionally a potentiator and/or a chemotherapeutic agent include but not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellularcarcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers which can be treated with the methods and compositions according to the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests. For example, amelioration or treatment of a patient suffering from an infectious disease organism, such as for example, Hepatitis B Virus, may be determined by a decrease of viral particles in a sample taken from a patient, as measured by, for example, a decrease in plaque forming units (p.f.u.).

The "treatment of neoplastic disease or neoplastic cells", refers to an amount of rapamycin resistant T cells, described throughout the specification and in the Examples which follow, capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

"Treatment of an individual suffering from an infectious disease organism" refers to a decrease or elimination of the disease organism from an individual. For example, a decrease of viral particles as measured by plaque forming units or other automated diagnostic methods such as ELISA, etc., may be used to monitor efficacy of treatment.

"Treatment of an individual suffering from graft-versus-host-disease or GVHD" refers to a decrease or cessation of symptoms associated with GVHD. For example, an amelioration of lacy, livid maculopapular rash, jaundice, diarrhea, abdominal pain, hepatosplenomegaly, alopecia, bullae, desquamation of skin. Treatment or amelioration of GVHD results in clinical downgrading of the disease. For example, acute GVHD, which typically occurs in the first 100 days post-transplant, may be classified according to degree or "stage" of damage in the main target organs of GVHD, the skin, intestine, and liver. For example, liver GVHD is staged from none (stage 0; bilirubin <2 mg/dl) to severe (stage 4; bilirubin >15 mg/dl) based on serum bilirubin level. Skin GVHD is staged based upon the percent body surface area that the rash involves, with stage 0 having no rash and stage 4 having rash of up to 100% body surface area with bullae or desquamation. Intestinal GVHD is staged based upon the volume of daily liquid stool output, with stage 0 being no diarrhea and stage 4 being >1500 ml liquid stool per day with abdominal pain or ileus. Chronic GVHD, which typically occurs after day 100 post-transplant and can last several years post-transplant, is typically scored based upon number of organ sites that the chronic GVHD involves (limited chronic GVHD, one site; extensive chronic GVHD, two or more sites). Chronic GVHD involves the same organs as acute GVHD, but in addition, chronic GVHD may also affect the mucous glands in the eyes, salivary glands in the mouth, and glands that lubricate the stomach lining and intestines.

As used herein, "an ameliorated symptom" or "treated symptom" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

"Cells of the immune system" or "immune cells" as used herein, is meant to include any cells of the immune system that may be assayed, including, but not limited to, B lymphocytes, also called B cells, T lymphocytes, also called T cells, natural killer (NK) cells, natural killer T (NKT) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"Immune effector cells" refers to cells capable of binding an antigen and which mediate an immune response selective for the antigen. These cells include, but are not limited to, T cells (T lymphocytes), B cells (B lymphocytes), monocytes, macrophages, natural killer (NK) cells and cytotoxic T lymphocytes (CTLs), for example CTL lines, CTL clones, and CTLs from tumor, inflammatory, or other infiltrates.

"Immune related molecules" refers to any molecule identified in any immune cell, whether in a resting ("non-stimulated") or activated state, and includes any receptor, ligand, cell surface molecules, nucleic acid molecules, polypeptides, variants and fragments thereof.

"T cells" or "T lymphocytes" are a subset of lymphocytes originating in the thymus and having heterodimeric receptors associated with proteins of the CD3 complex (e.g., a rearranged T cell receptor, the heterodimeric protein on the T cell surfaces responsible for antigen/MHC specificity of the cells). T cell responses may be detected by assays for their effects on other cells (e.g., target cell killing, activation of other immune cells, such as B-cells) or for the cytokines they produce.

As used herein, "allogeneic" is used to refer to immune cells derived from non-self major histocompatibility complex donors. HLA haplotypes/allotypes vary from individual to individual and it is often helpful to determine the individuals HLA type. The HLA type may be determined via standard typing procedures.

As will be recognized by those in the art, the term "host compatible" or "autologous" cells means cells that are of the same or similar haplotype as that of the subject or "host" to which the cells are administered, such that no significant immune response against these cells occurs when they are transplanted into a host.

As used herein, "partially-mismatched HLA", refers to HLA types that are between about 20% to about 90% compatible to the host's HLA type.

"CD4" is a cell surface protein important for recognition by the T cell receptor of antigenic peptides bound to MHC class II molecules on the surface of an APC. Upon activation, naïve CD4 T cells differentiate into one of at least two cell types, Th1 cells and Th2 cells, each type being characterized by the cytokines it produces. "Th1 cells" are primarily involved in activating macrophages with respect to cellular immunity and the inflammatory response, whereas "Th2 cells" or "helper T cells" are primarily involved in stimulating B cells to produce antibodies (humoral immunity). CD4 is the receptor for the human immunodeficiency virus (HIV). Effector molecules for Th1 cells include, but are not limited to, IFN-γ, GM-CSF, TNF-α, CD40 ligand, Fas ligand, IL-3, TNF-β, and IL-2. Effector molecules for Th2 cells include, but are not limited to, IL-4, IL-5, CD40 ligand, IL-3, GS-CSF, IL-10, TGF-β, and eotaxin. Activation of the Th1 type cytokine response can suppress the Th2 type cytokine response, and reciprocally, activation of the Th2 type cytokine response can suppress the Th1 type response.

A "chemokine" is a small cytokine involved in the migration and activation of cells, including phagocytes and lymphocytes, and plays a role in inflammatory responses.

A "cytokine" is a protein made by a cell that affect the behavior of other cells through a "cytokine receptor" on the surface of the cells the cytokine effects. Cytokines manufactured by lymphocytes are sometimes termed "lymphokines." Cytokines are also characterized as Type I (e.g. IL-2 and IFN-γ) and Type II (e.g. IL-4 and IL-10).

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values.

An "epitope", as used herein, is a portion of a polypeptide that is recognized (i.e., specifically bound) by a B-cell and/or T-cell surface antigen receptor. Epitopes may generally be identified using well known techniques, such as those summarized in Paul, Fundamental Immunology, 3rd ed., 243-247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, Antibodies: A Laboratory Manual, Cold Spring Harbor Laboratory, 1988. B-cell and T-cell epitopes may also be predicted via computer analysis.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Immunoassay" is an assay that uses an antibody to specifically bind an antigen (e.g., a marker). The immunoassay is characterized by the use of specific binding properties of a particular antibody to isolate, target, and/or quantify the antigen.

As used herein, the term "transplant" includes any cell, organ, organ system or tissue which can elicit an immune response in a recipient subject mammal. In general, therefore, a transplant includes an allograft or a xenograft cell, organ, organ system or tissue. An allograft refers to a graft (cell, organ, organ system or tissue) obtained from a member of the same species as the recipient. A xenograft refers to a graft (cell, organ, organ system or tissue) obtained from a member of a different species as the recipient.

The term "immune rejection," as used herein, is intended to refer to immune responses involved in transplant rejection, as well as to the concomitant physiological result of such immune responses, such as for example, interstitial fibrosis, chronic graft artheriosclerosis, or vasculitis. The term "immune rejection," as used herein, is also intended to refer to immune responses involved in autoimmune disorders, and the concomitant physiological result of such immune responses, including T cell-dependent infiltration and direct tissue injury; T cell-dependent recruitment and activation of macrophages and other effector cells; and T cell-dependent B cell responses leading to autoantibody production.

The term "transplant rejection," as used herein, refers to T cell-mediated rejection of transplant cells, organs, organ systems or tissue. In general, such transplant rejection generally includes accelerated, acute and chronic rejection. It is intended that the term, as used herein, also refer to GVHD, and the physiological results of such a disorder.

The term "reducing immune rejection," is meant to encompass prevention or inhibition of immune rejection, as well as delaying the onset or the progression of immune rejection. The term is also meant to encompass prolonging survival of a transplant in a subject mammal, or reversing failure of a transplant in a subject. Further, the term is meant to encompass ameliorating a symptom of an immune rejection, including, for example, ameliorating an immunological complication associated with immune rejection, such as for example, interstitial fibrosis, chronic graft atherosclerosis, or vasculitis. The term is also meant to encompass induction of tolerance in a subject mammal that has undergone a transplant.

The term "tolerance," as used herein, refers to a state wherein the immune system of a transplant recipient subject mammal is non-responsive to the transplant. This state is considered donor transplant-specific, and, as such, is distinguished from nonspecific immunosuppression. Operatively, the term as used herein, refers to permanent acceptance of a graft without ongoing immunosuppression, wherein, for example, challenge with a second graft of donor origin (especially when the second graft is of the same tissue as the first graft) should be accepted, and challenge with a third party graft should be rejected.

The term "autoimmune rejection," as used herein, refers to immune responses involved in autoimmune disorders, and the concomitant physiological result of such immune responses.

The term "activated T cell," as used herein, refers to a T cell that expresses antigens indicative of T-cell activation (that is, T cell activation markers). Examples of T cell activation markers include, but are not limited to, CD25, CD26, CD30, CD38, CD69, CD70, CD71, ICOS, OX-40 and 4-1BB. The expression of activation markers can be measured by techniques known to those of skill in the art, including, for example, western blot analysis, northern blot analysis, RT-PCR, immunofluorescence assays, and fluorescence activated cell sorter (FACS) analysis.

The term "resting T cell," as used herein, refers to a T cell that does not express T-cell activation markers. Resting T cells include, but are not limited to, T cells which are $CD25^-$, $CD69^-$, $ICOS^-$; $SLAM^-$, and $4-1BB^-$. The expression of these markers can be measured by techniques known to those of skill in the art, including, for example, western blot analysis, northern blot analysis, RT-PCR, immunofluorescence assays, and fluorescence activated cell sorter (FACS) analysis.

The term "T cell activator," as used herein, refers to any compound or factor that is a T cell receptor stimulatory factor, that is, induces T cell receptor signaling. Preferably, the compound or factor also induces co-stimulatory pathways. Non-limiting examples of T cell activators include, but are not limited to, anti-CD3, antibodies (preferably monoclonal antibodies) either alone or in conjunction with anti-CD28 antibodies (preferably monoclonal antibodies), or mitogens such as, for example, phorbol 12-myristate 13-acetate (PMA), phytohemagglutinin (PHA) or concanavalin-A (Con-A).

BRIEF DESCRIPTION OF THE FIGURES

FIG. 4 is a graph showing that at a high dose of rapamycin, co-stimulation and cytokine supplementation allowed for the expansion of either Th1 or Th2 subsets without any apparent reduction in numbers of CD4-expressing cells.

FIG. 16 is a graph showing CTL assays using Tc2 effectors generated in the presence or absence of rapamycin.

FIG. 17 is a graph showing Tc1 cells expanded in the high dose of rapamycin lost their capacity for IFN-γ secretion and had reduced capacity for IL-2 secretion.

FIG. 23 shows the results of CD4+ cell expansion from n=4 normal donors either without (left panel) or with rapamycin (1.0 µM; right panel).

FIG. 31 is a graph showing purified naïve or memory human CD4 cells co-stimulated either with or without rapamycin.

DETAILED DESCRIPTION OF THE INVENTION

We have now found new methods and T cell based systems in the field of immune therapy against cancers, infectious diseases, reduction of graft versus host disease (GVHD) and the like.

As shown in the examples which follow, we have demonstrated that rapamycin generated T cells were selectively resistant to the inhibitory effects of rapamycin in vivo. In this strategy, in vivo administration of rapamycin-resistant Th1, Th2, Tc1 or Tc2 cells with concomitant administration of rapamycin drug inhibits non-cultured T cells that may not possess the desired function and at the same time allow preferential expansion of the in vitro cultured T cell of optimal function. This new immune therapy strategy greatly amplifies the in vivo effects of immune therapeutic T cells of a selected function.

Preferred methods of T cell subset generation are growth in in vitro T cell culture conditions comprising the immune suppression drug rapamycin to generate rapamycin-resistant cells having a desired T lymphocyte function, such as for example, T helper cells (Th1 or Th2 function) and/or cytotoxic T cells (Tc1 or Tc2 function). Preferably, the desired T cell subset is selected for, activated, and co-administered with rapamycin to a patient in need of therapy. For example, patients with cancer or infectious disease, where a Th1 or Tc1 cell would provide optimal T cell function, T cells are harvested from the patient, activated and expanded in the identified conditions with rapamycin to generate rapamycin-resistant Th1 or Tc1 cells, then re-infused to the patient with simultaneous administration of rapamycin drug. This expands the therapeutic T cell against cancer or infection, and inhibits any non-cultured T cell in the body that might otherwise adversely affect the therapeutic T cell response.

Alternatively, in cases of GVHD prevention or treatment, or therapy of autoimmune disease, T cells would be harvested from the patient, expanded in conditions containing rapamycin to generate, preferably, rapamycin resistant Th2 or Tc2 cells, and then re-infused to the patient with simultaneous administration of the rapamycin drug. Preferably, the immune therapeutic T cells are expanded to prevent GVHD or treat autoimmune disease, and inhibit any non-cultured T cell in the body that may otherwise promote GVHD or autoimmune disease.

As used herein, "therapeutic T cell" refers to the rapamycin resistant T cell subsets, for example, Th1/Tc1 and Th2/Tc2.

As used herein, the term "rapamycin" refers to rapamycin and/or structurally modified rapamycin compounds (such structurally modified rapamycin compounds sometimes referred to herein as rapamycin derivatives). The unmodified compound is the macrolide antibiotic that can be produced by *Streptomyces hyhoscopius* having the structure as disclosed e.g. in J. B. McAlpine et al. *J. Antibiotics* (1991) 44:688 and S. L. Schrieber et al., *J. Am. Chem. Soc.*, (1991) 113:7433.

Figure 1:
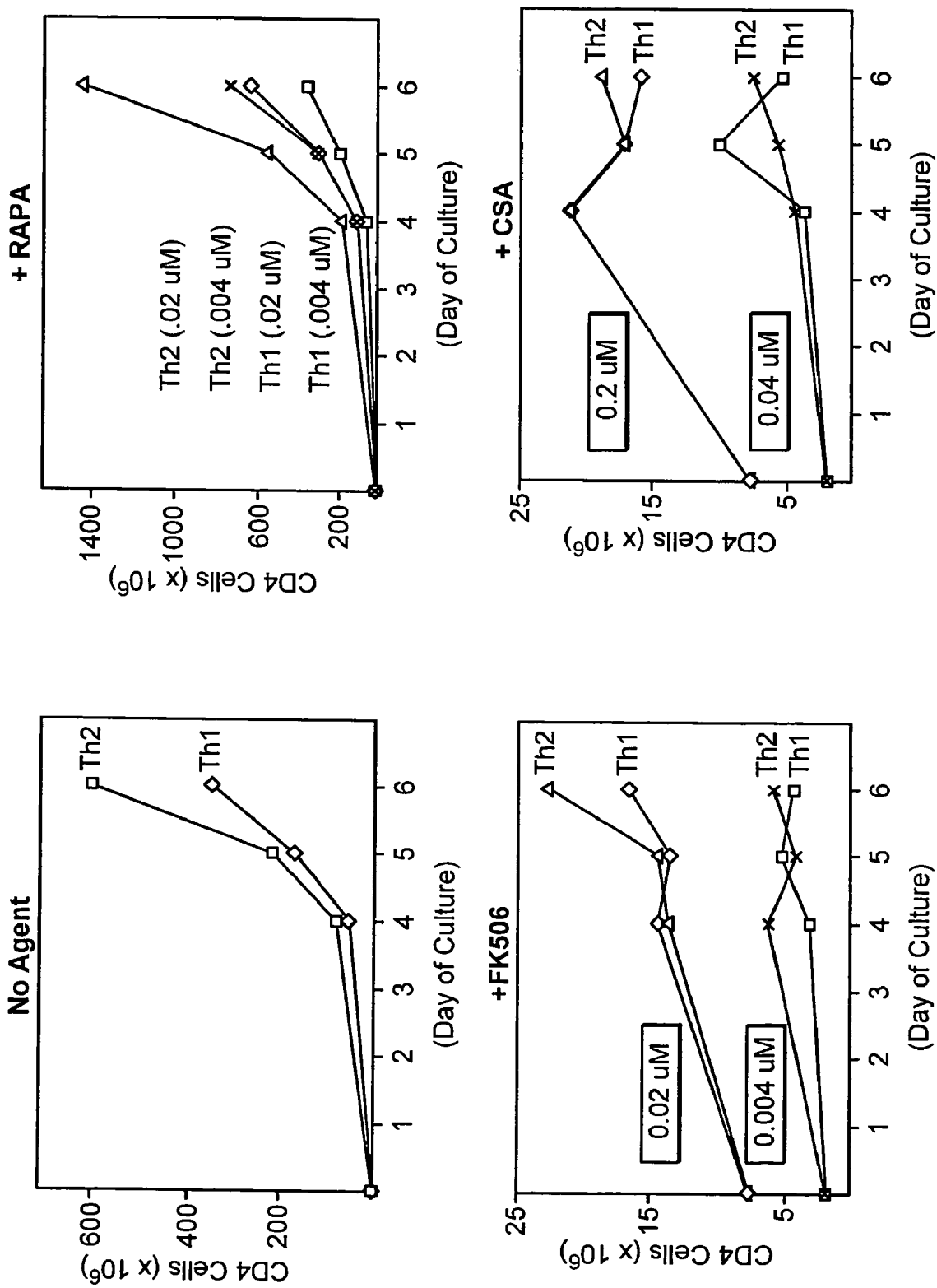
FIG. 1 is a graph illustrating the differential effect of CSA, FK506, and rapamycin on the generation of murine $CD4^+$ Th1 and Th2 cells.

That unmodified rapamycin is in general a preferred rapamycin compound and is the compound referred to in the examples which follow. Additional suitable and preferred structurally modified rapamycin compounds (or rapamycin derivatives) can be identified through simple testing. For instance, suitable rapamycin derivatives for identifying resistant cells can be evaluated using in vitro assays as described in detail in the Examples which follow. Briefly, cells such as for example T cells are stimulated and cultured in the presence of cytokines till the cells reach a desired concentration, such as for example $2\times10^6$ cells. Candidate rapamycin derivative compounds are added to the cell culture in varying concentrations such as at least about 0.004 µM up to about 0.02 µM. Viable cells as determined by microscopic observations or dye exclusion assays are counted by a Multi-Sizer Instrument (Coulter), and the cellular expansion, for example, CD4 expansion is plotted, as shown in FIG. 1. If a candidate rapamycin compound results in decrease in cell populations as compared to normal controls and controls incubated with rapamycin, then the compound is considered suitable for use in the methods and compositions of the invention. Candidate rapamycin compounds, include, but are not limited to, tetrazole containing rapamycin analogs disclosed in U.S. Pat. No. 6,329,386; acyl derivatives of rapamycin disclosed in U.S. Pat. No. 4,316,885; mono- and diester derivatives of rapamycin; 27-oximes of rapamycin; 42-oxo analog of rapamycin; bicyclic rapamycins disclosed in U.S. Pat. No. 5,120,725; rapamycin dimers disclosed in U.S. Pat. No. 5,120,727; silyl ethers, arylsulfonates and sulfamates of rapamycin disclosed in U.S. Pat. No. 5,120,842; sulfonates disclosed in U.S. Pat. No. 5,177,203; mono- and di-acyl derivatives of rapamycin; water soluble rapamycin compounds disclosed in U.S. Pat. No. 4,650,803; hydrogenated rapamycin derivatives such as those disclosed in U.S. Pat. No. 5,023,262; all references cited herein, are incorporated herein in their entirety.

The number of cells of desired function, administered to the patient will vary depending on various factors such as the disease or condition to be treated, the condition of the patient, which should be determined via consideration of all appropriate factors by the practitioner. Preferably, however, about $1\times10^6$ to about $1\times10^{12}$ cells of desired function are administered to a patient, more preferably about $1\times10^8$ to about $1\times10^{11}$ cells of desired function are administered to a patient, and even more preferably, about $1\times10^9$ to about $1\times10^{10}$ cells of desired function are administered to an adult human. Most preferred, the number of cells administered are about $2.5\times10^9$ cells. These amounts will vary depending on the age, weight, size, condition, sex of the patient, the type of disease to be treated, the route of administration, whether the treatment is regional or systemic, and other factors. Those skilled in the art should be readily able to derive appropriate dosages and schedules of administration to suit the specific circumstance and needs of the patient.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of CD8⁺ cells of Th1/Tc1 function via intravenous infusion is appropriate.

T cells from patients are, preferably activated ex vivo, either by soluble anti-CD3 antibody, or most preferably, are co-activated by using anti-CD3 and anti-CD28 monoclonal antibodies, either by soluble or immobilized on a solid support. A preferred solid support are plastics, or any surface upon which antibodies can be immobilized, or beads, such as, for example, Dynal beads. Particularly preferred surface antigens for optimal co-stimulation are CD3 and/or CD28 and particular secreted cytokines (like IL-2, IL-4, IL-10, IFN-γ).

The present invention is also useful as the activation is conducted in vitro and the activated helper or cytotoxic T-cells are reintroduced into the patient. Activation is achieved by the crosslinking of the T cell receptor complex (anti-CD3 and anti-CD28 antibodies) which increase the effectiveness of the activation. Cross linking of the TCR with anti-CD3 triggers a signaling cascade resulting in T cell proliferation, cytokine synthesis, and immune responses. However, optimal activation and proliferation requires costimulation of CD28 receptors on T cells with anti-CD28 or B7 molecules (CD80 and CD86). These interactions enhance proliferation and stabilization of mRNAs for IL-2, IFN-γ, TNF-α, and granulocyte-macrophage colony stimulating factor (GM-CSF). Costimulation of the CD28 receptor also leads to enhanced production of beta chemokines RANTES, and MIP1-α. The enhanced secretion of chemokines at the tumor site may augment recruitment of effector cells.

The presentation of antigen to CD8 T-cells is accomplished by major histocompatibility complex (MHC) molecules of the Class I type. The major histocompatibility complex (MHC) refers to a large genetic locus encoding an extensive family of glycoproteins which play an important role in the immune response. The MHC genes, which are also referred to as the HLA (human leukocyte antigen) complex, are located on chromosome 6 in humans. The molecules encoded by MHC genes are present on cell surfaces and are largely responsible for recognition of tissue transplants as "non-self". Thus, membrane-bound MHC molecules are intimately involved in recognition of antigens by T-cells.

MHC products are grouped into three major classes, referred to as I, II, and III. T-cells that serve mainly as helper cells express CD4 and primarily interact with Class II molecules, whereas CD8-expressing cells, which mostly represent cytotoxic effector cells, interact with Class I molecules.

As used herein, the term "transplantation antigen" is used to refer to antigenic molecules that are expressed on the cell surface of transplanted cells, either at the time of transplantation, or at some point following transplantation. Generally these antigenic molecules are proteins and glycoproteins. The primary transplantation antigens are products of the major histocompatibility complex (MHC), located on chromosome 6 in humans. The human MHC complex is also called the human leukocyte antigen (HLA) complex. MHC antigens are divided into MHC class I antigens (in humans, this class includes HLA-A, -B, and -C antigens) and MHC class II antigens (in humans, this class includes HLA-DP, -DQ, and -DR antigens). Thus, the terms "MHC-II antigens", "MHC class II antigens", and "MHC class II transplantation antigens" are used interchangeably herein to refer to the class of proteins, which in humans, includes HLA-DP, -DQ and -DR antigens. While the terms "MHC class II genes" and "MHC-II genes" are used interchangeably herein to refer to the genes which encode the MHC class II transplantation antigens. The term "MHC-II" is used herein to refer to the gene locus which encodes the MHC class II transplantation antigens, as well as the group of proteins encoded by that locus. Transplantation antigens also include cell surface molecules other than MHC class I and II antigens. These antigens include the following: (1) the ABO antigens involved in blood cell recognition; (2) cell adhesion molecules such as ICAM, which is involved in leukocyte cell-cell recognition; and (3) β2-microglobulin, a polypeptide associated with the 44 kd heavy chain polypeptide that comprises the HLA-I antigens but is not encoded by the MHC complex. Even in those cases where the most complete HLA matching is correctly done, GVHD frequently results. It has been suggested that GVHD results, in those instance, from alloaggression due to minor histocompatibility antigen differences for which many authors have suggested the depletion of donor T cells as a means to avoid GVHD. Although this strategy of T cell depletion may avoid GVHD, such patients are at increased risk for tumor relapse, infection, and graft rejection, and as such, T cell depletion has both positive and negative consequences.

Class I molecules are membrane glycoproteins with the ability to bind peptides derived primarily from intracellular degradation of endogenous proteins. Complexes of MHC molecules with peptides derived from viral, bacterial and other foreign proteins comprise the ligand that triggers the antigen responsiveness of T-cells. In contrast, complexes of MHC molecules with peptides derived from normal cellular products play a role in "teaching" the T-cells to tolerate self-peptides, in the thymus. Class I molecules do not present entire, intact antigens; rather, they present peptide fragments "loaded" onto their "peptide binding groove".

The presentation of Class I MHC molecules bound to peptide alone has generally been ineffective in activating CD8 cells. In nature, the CD8 cells are activated by antigen-presenting cells, such as, for example, dendritic cells, which present not only a peptide-bound Class I MHC molecule, but also a costimulatory molecule. Such costimulatory molecules include B7 which is now recognized to be two subgroups designated as B7.1 and B7.2. It has also been found that cell adhesion molecules such as integrins assist in this process.

Dendritic cells are antigen-presenting cells that are found in all tissues and organs, including the blood. Specifically, dendritic cells present antigens for T lymphocytes, i.e., they process and present antigens, and stimulate responses from naive and memory T cells. In addition to their role in antigen presentation, dendritic cells directly communicate with non-lymph tissue and survey non-lymph for an injury signal (e.g., ischemia, infection, or inflammation) or tumor growth. Once signaled, dendritic cells initiate the immune response by releasing IL-1 which triggers lymphocytes and monocytes.

When the CD8 T-cell interacts with an antigen-presenting cell, such as a dendritic cells, having the peptide bound by a Class I MHC and costimulatory molecule, the CD8 T-cell is activated to proliferate and becomes an effector T-cell. See, generally, Janeway and Travers, Immunobiology, published by Current Biology Limited, London (1994), incorporated by reference.

In another preferred embodiment, rapamycin resistant T cells co-administered with rapamycin ameliorate GVHD as determined by the change in stage of GVHD. Preferably, graft-versus-host-disease is ameliorated by at least about 50%, more preferably by at least about 75%, most preferably about at least 90%, 95%, 98%, 99%, 99.9% or 100%.

In another preferred embodiment, autologous T cells from the patient are cultured in rapamycin and/or a rapamycin derivative and under conditions to generate a Th2 response. Preferred conditions include the addition of cytokines such as IL-4 and IL-2, and rapamycin and/or a rapamycin derivative, alone. Specific conditions are described in the Examples which follow.

In another preferred embodiment, allogeneic donor Th2 cells are used to supplement the allotransplant. Preferably, the allogeneic Th2 cells increase in number with a concomitant decrease in GVHD.

In another preferred embodiment, immune T cell therapy is utilized for the treatment of a wide range of medical conditions such as cancer, disease due to infectious disease organisms such as viruses, autoimmune diseases, immunosuppressed individuals, burn victims and Graft versus Host Disease.

In another preferred embodiment, the invention provides for pharmaceutical compositions comprising rapamycin and/or a rapamycin derivative compound and/or rapamycin resistant T cells, rapamycin resistant stem cells and/or rapamycin resistant dendritic cells.

In a further aspect, the invention provides use of a rapamycin resistant T cell; a rapamycin resistant stem cell; a rapamycin resistant dendritic cell; composition for the treatment or prevention (including prophylactic treatment) of a disease or condition as disclosed herein, including acute GVHD, chronic GVHD, lacy, livid maculopapular rash, jaundice, diarrhea, abdominal pain, hepatosplenomegaly, alopecia, bullae, desquamation of skin; prolonging survival of a transplant in a subject mammal, or reversing failure of a transplant in a subject and ameliorating disorders and symptoms such as associated with immune rejection, including, for example, interstitial fibrosis, chronic graft atherosclerosis, or vasculitis; treatment of cancers such as, leukemias, lymphomas, melanomas, carcinomas and sarcomas; diseases caused by or otherwise associated with a virus such as viruses of the herpes family, e.g., herpes simplex viruses (HSV) including herpes simplex 1 and 2 viruses (HSV 1, HSV 2), varicella zoster virus (VZV; shingles), human herpes virus 6, cytomegalovirus (CMV), Epstein-Barr virus (EBV), and other herpes virus infections such as feline herpes virus infections, and diseases associated with hepatitis viruses including hepatitis B viruses (HBV) B virus. Examples of clinical conditions which are caused by such viruses include herpetic keratitis, herpetic encephalitis, cold sores and genital infections (caused by herpes simplex), chicken pox and shingles (caused by varicella zoster) and CMV-pneumonia and retinitis, particularly in immunocompromised patients including renal and bone marrow transplant patients and patients with Acquired Immune Deficiency Syndrome (AIDS). Epstein-Barr virus can cause infectious mononucleosis, and is also suggested as the causative agent of nasopharyngeal cancer, immunoblastic lymphoma and Burkitt's lymphoma Additional specific examples of retroviral infections which may be suitably treated in accordance with the invention include human retroviral infections such as HIV-1, HIV-2, and Human T-cell Lymphotropic Virus (CLV) e.g. HTLV-I or HTLV-II infections.

In yet a further aspect, the invention provides use of a rapamycin resistant T cell; a rapamycin resistant stem cell; a rapamycin resistant dendritic cell; composition for the preparation of a medicament for the treatment or prevention (including prophylactic treatment) of a disease or condition as disclosed herein, including acute GVHD, chronic GVHD, lacy, livid maculopapular rash, jaundice, diarrhea, abdominal pain, hepatosplenomegaly, alopecia, bullae, desquamation of skin; prolonging survival of a transplant in a subject mammal, or reversing failure of a transplant in a subject and ameliorating disorders and symptoms such as associated with immune rejection, including, for example, interstitial fibrosis, chronic graft atherosclerosis, or vasculitis; treatment of cancers such as, leukemias, lymphomas, melanomas, carcinomas and sarcomas; diseases caused by or otherwise associated with a virus such as viruses of the herpes family, e.g., herpes simplex viruses (HSV) including herpes simplex 1 and 2 viruses (HSV 1, HSV 2), varicella zoster virus (VZV; shingles), human herpes virus 6, cytomegalovirus (CMV), Epstein-Barr virus (EBV), and other herpes virus infections such as feline herpes virus infections, and diseases associated with hepatitis viruses including hepatitis B viruses (HBV) B virus. Examples of clinical conditions which are caused by such viruses include herpetic keratitis, herpetic encephalitis, cold sores and genital infections (caused by herpes simplex), chicken pox and shingles (caused by varicella zoster) and CMV-pneumonia and retinitis, particularly in immunocompromised patients including renal and bone marrow transplant patients and patients with Acquired Immune Deficiency Syndrome (AIDS). Epstein-Barr virus can cause infectious mononucleosis, and is also suggested as the causative agent of nasopharyngeal cancer, immunoblastic lymphoma and Burkitt's lymphoma. Additional specific examples of retroviral infections which may be suitably treated in accordance with the invention include human retroviral infections such as HIV-1, HIV-2, and Human T-cell Lymphotropic Virus (HTLV) e.g. HTLV-I or HTLV-II infections.

Preferred methods of the invention including identifying and/or selecting a subject (e.g. a mammal, particularly human) that is susceptible to or suffering from a condition disclosed herein, and thereafter administering to the identified and selected subject one or more compounds of the invention, particularly a subject that is identified and selected as being susceptible to or suffering from acute GVHD, chronic GVHD, lacy, livid maculopapular rash, jaundice, diarrhea, abdominal pain, hepatosplenomegaly, alopecia, bullae, desquamation of skin; prolonging survival of a transplant in a subject mammal, or reversing failure of a transplant in a subject and ameliorating disorders and symptoms such as associated with immune rejection, including, for example, interstitial fibrosis, chronic graft atherosclerosis, or vasculitis; treatment of cancers such as, leukemias, lymphomas, melanomas, carcinomas and sarcomas; diseases caused by or otherwise associated with a virus such as viruses of the herpes family, e.g., herpes simplex viruses (HSV) including herpes simplex 1 and 2 viruses (HSV 1, HSV 2), varicella zoster virus (VZV; shingles), human herpes virus 6, cytomegalovirus (CMV), Epstein-Barr virus (EBV), and other herpes virus infections such as feline herpes virus infections, and diseases associated with hepatitis viruses including hepatitis B viruses (HBV) B virus. Examples of clinical conditions which are caused by such viruses include herpetic keratitis, herpetic encephalitis, cold sores and genital infections (caused by herpes simplex), chicken pox and shingles (caused by varicella zoster) and CMV-pneumonia and retinitis, particularly in immunocompromised patients including renal and bone marrow transplant patients and patients with Acquired Immune Deficiency Syndrome (AIDS). Epstein-Barr virus can cause infectious mononucleosis, and is also suggested as the causative agent of nasopharyngeal cancer, immunoblastic lymphoma and Burkitt's lymphoma. Additional specific examples of retroviral infections which may be suitably treated in accordance with the invention include human retroviral infections such as HIV-1, HIV-2, and Human T-cell Lymphotropic Virus (HTLV) e.g. HTLV-I or HTLV-II infections.

In a preferred embodiment, T cell function is selected based on the cell type that is generated by the immune system in response to that disease. For example, the immune system effectively responds to a viral, bacterial, and fungal infection by generating a Th1/Tc1 cell subset; an effective immune response to other infections may require the generation of a Th2/Tc2 response. It is also possible that both a Th1/Tc1 and Th2/Tc2 immune response may be optimal in some treatment settings, so as to invoke both cellular and antibody arms of the immune response. From work by Mossman and Coffman (Mossmann T. R., Coffmann R. L.: Th1 and Th2 cells: Different patterns of lymphokine secretion lead to different functional properties. *Ann. Rev. Immunol.* 1989, 7: 145-173), growth factors known as cytokines produced by T helper or CD4$^+$ T cells in both human and murine systems were classified into two subsets, Th1 and Th2. These were characterized by their functions in regulating various types of immune responses. Cytokines produced by Th1 cells [interleukin (IL)-2, interferon-alpha, interferon-gamma, tumor necrosis factor-alpha (TNF-$\alpha$), IL-12] stimulated strong cellular immunity whereas Th2 cytokines [IL-4, IL-5, IL-6, IL-10, IL-13] were important for eliciting humoral (antibody) responses in vivo. Cytokines produced by non-CD4$^+$ T cells have been shown to be important in in vivo responses. In particular, the cytotoxic or CD8$^+$ T cells can also be subdivided into two subgroups, Tc1 and Tc2, which correspond to the same subsets in T helper cells (Carter L. L., Dutton R. W.: Type 1 and Type 2: a functional dichotomy for all T cell subsets. *Curr. Opin. Immunol.* 1996, 8: 336-342). This has led to the current nomenclature being generalized from Th1/Th2 to Type 1/Type 2 to reflect more closely the response generated by particular cytokines, rather than the cell types that produces them.

In vitro T cell cytotoxic assays are well known to those skilled in the art. In general, cytotoxicity is measured in a 5 hr $^{51}$Sodium chromate ($^{51}$Cr) release assay. Target cells, that is cells that are recognized by the T cells are plated in flat-bottomed microtiter plates and incubated at 37° C. overnight. The targets are washed and labeled the next day with $^{51}$Cr at 37° C. $^{51}$Cr is taken up by the target cells, either by endocytosis or pinocytosis, and is retained in the cytoplasm. The wells containing target cells are washed, and then T cells, referred to as "effector cells" are plated at different E:T ratios and incubated overnight at 37° C. Cytolysis is a measure of the $^{51}$Cr released from the target cells into the supernatant due to destruction of the target cells by the effector cells. The microtiter plates are centrifuged at 1000 rpm for 10 minutes and an aliquot of about 50 µl to about 100 µl is removed and the level of radioactivity is measured the next day by a gamma counter and the percent specific lysis calculated.

Percent specific lysis is measured by using the formula:

($^{51}$Cr released from the target cells)−(spontaneous $^{51}$Cr released from the target cells)/(maximum $^{51}$Cr released from the target cells)−(spontaneous $^{51}$Cr released from the target cells)×100

The spontaneous $^{51}$Cr released from the target cells is measured with tumor cells to which no effector cells have been added. Maximum $^{51}$Cr released from the target cells is obtained by adding, for example, 1M HCl and represents the total amount of $^{51}$Cr present in the cytoplasm of the target cell.

Other cytotoxicity assays such as the labeling of target cells with tritiated thymidine ($^3$H-TdR) may also be used. $^3$H-TdR is taken up by target cells into the nucleus of the cell. Release of $^3$H-TdR is a measure of cell death by DNA fragmentation. The assay is conducted as above except the incubation period is at least about 48 hours and 50 µl to about 100 µl of the supernatant is measured by a beta-counter in the presence of at least about 1 ml of scintillation fluid. Calculation of percent specific lysis is performed using the above formula.

T cell proliferation assays are used to determine class II MHC antigen recognition. Briefly, target cells are irradiated so that they do not proliferate. The source of the target cells can be allogeneic or autologous cells. CD4$^+$ T cells are incubated with the irradiated target cells in the presence of $^3$H-TdR. The CD4$^+$ T cells react against the Class II MHC by proliferating. Proliferation is measured by the amount of $^3$H-TdR that is taken up by the proliferating T cells as compared to normal control cells.

The search for additional immunosuppressive agents for preventing transplant rejection and for the treatment of autoimmune and inflammatory disorders occupies considerable attention in the pharmaceutical industry. Since cytokines such as interferon-gamma and tumor necrosis factor-alpha play a critical role in transplant rejection and in the pathophysiology of autoimmune disorders, much effort has been invested in the development of agents that suppress their production, secretion and/or end-organ effect.

While not being bound by any theory, the methods described herein, which ameliorate organ transplant rejection and/or GVHD, are believed due to an increase in Th2/Tc2 function. This is surprising and contrary to the teachings in the prior art whereby, immunosuppressants are used to suppress immune responses, thereby, preventing prevent organ rejection or GVHD.

Figure 29:
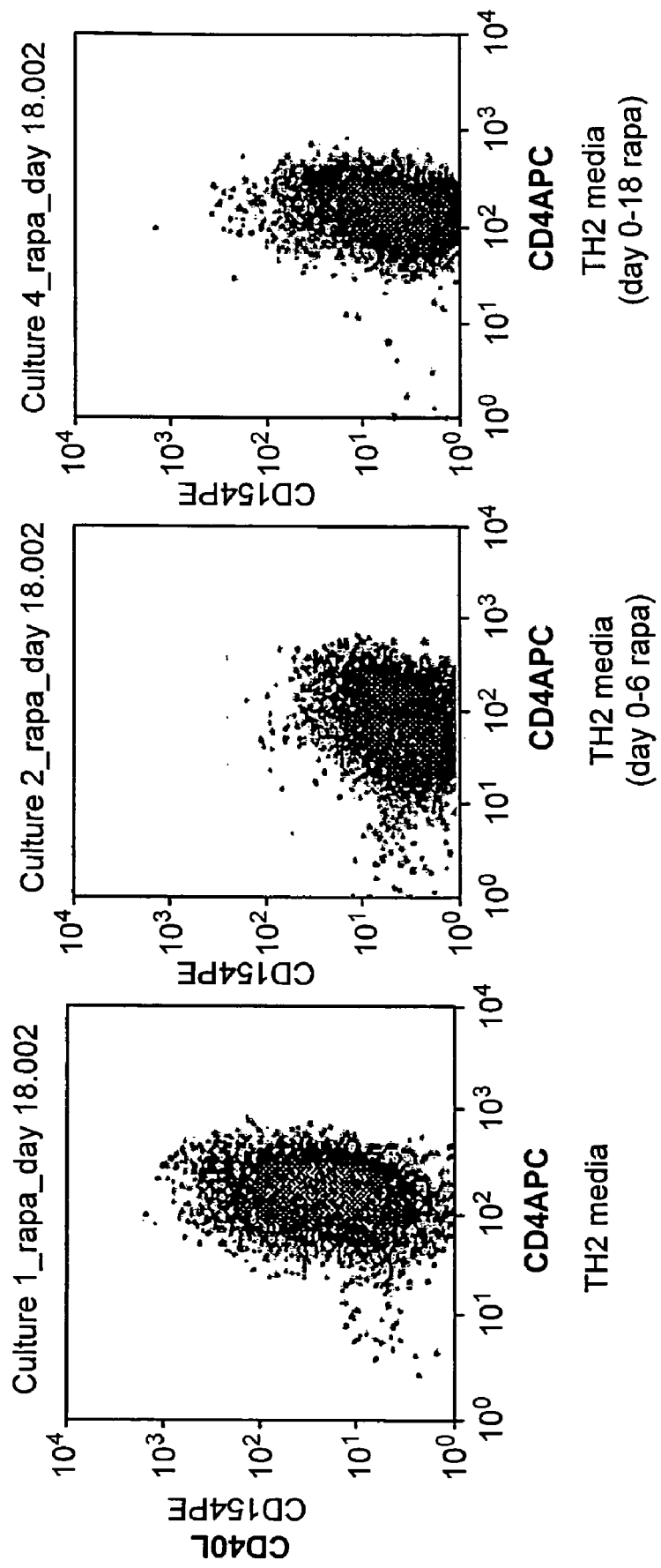
FIG. 29 is a graph showing rapamycin-generated Th2 cells indeed had an increased capacity for rhodamine dye exclusion.
Figure 30:
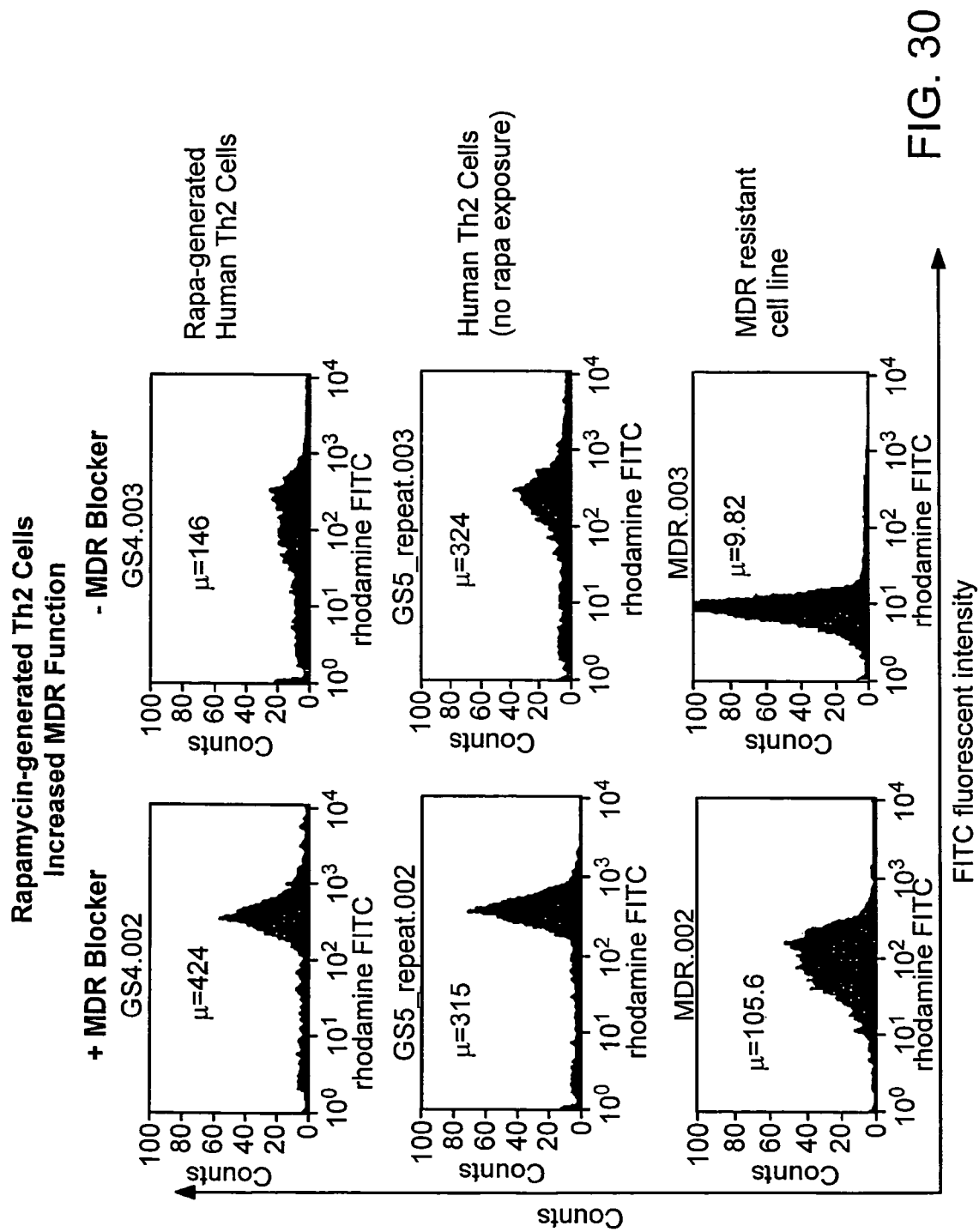
FIG. 30 is a graph showing that rapamycin generated Th2 cells increased MDR function.

Without being bound by any theory, one potential mechanism that may contribute to the observed rapamycin-associated changes in human Th2 cell generation is preferential utilization of the multi-drug resistance (MDR) pump in cells of more naïve phenotype. That is, previous data indicates that human naïve CD45RA$^+$ cells express increased MDR, and to this extent, such cells may be intrinsically more resistant to rapamycin effects. To initiate investigation into this possibility, Th2 cells expanded with or without rapamycin were evaluated for their ability to exclude an MDR substrate, rhodamine. This evaluation was performed by flow cytometry in the presence or absence of an MDR pump inhibitor (results in FIG. 29). As this figure shows, rapamycin-generated Th2 cells indeed had an increased capacity for rhodamine dye exclusion. This enhanced MDR function in the rapamycin-generated Th2 cells was significantly abrogated by the MDR blocking agent.

Graft-versus host disease, the reaction of the donor immune system in allogeneic transplantation against the tissue of the recipient, is initiated by a T-cell reaction. Such T cells, in addition to causing GVHD, can also mediate a beneficial graft-versus-leukemia/lymphoma (GVL) effect or graft-versus-tumor (GVT) effect to eradicate the malignant clone. GVHD occurs at 3 different time points after transplantation, involving different organs and with different clinical and histopathological pictures. Hyper-acute and acute GVHD develop during and after engraftment till day+100 post-transplant; an acute inflammation of the recipient's tissue especially involving skin, soft tissue of the whole gastrointestinal-tract, liver and biliary tract system. In accordance with the degree of skin involvement, amount of diarrhea and the value of ALT/AST and bilirubin four different grades are defined as 0-IV. Acute GVHD≧II typically needs an intensification of the immunosuppressive therapy and grade III/IV are often refractory to high dose immunosuppression.

Chronic GVHD typically develops after day+100, and usually ensues directly from acute GVHD or during the reduction of the immunosuppression. Histologically, the tissue of chronic GVHD shows no inflammation but does show a fibrotic or sclerotic appearance. Skin, liver and the GI-tract tissue are involved and additionally: eyes, sino bronchial-system, lung, pancreas or vagina. A reduced quality of life is the result of decreased organ functions. Therefore, avoiding refractory acute and chronic GVHD is the main goal of the rapamycin resistant T cell based therapy before and after transplantation. The added advantage is that the associated increase of risk of infection is not observed as is the case with treatment with immunosuppressive agents, as the rapamycin resistant T cells are fully functional. (See the examples which follow).

In another preferred embodiment, the rapamycin resistant T cells express CD62L. CD62L mediates lymphocyte homing to high endothelial venules of peripheral lymphoid tissue and leukocyte rolling on activated endothelium at inflammatory sites. CD62L is expressed on the surfaces of most peripheral blood B cells, T cells, monocytes and granulocytes express CD62L. However, some NK cells express CD62L; some spleen lymphocytes, bone marrow lymphocytes, bone marrow myeloid cells and thymocytes express CD62L; and, certain hematopoietic malignant cells express CD62L.

T cells at different stages of maturation or differentiation express surface molecules indicative of that stage or differentiation. For example, memory T cells express $CD45RO^+$. Memory T cells can be expanded (proliferated) without the need of specific antigenic stimulation to maintain the clonal size. Naïve T cell repertoires express $CD45RA^+$. For example, to evaluate the frequency of resting T cells with memory phenotype that could be stimulated by cytokines to grow, limiting dilution experiments can be performed. $CD45RO^+CD4^+$ resting T cells can be cultured with IL-2 alone or in combination with TNF-$\alpha$ and IL-6, in the presence of autologous irradiated macrophages and anti-DR antibodies to prevent autoreactive responses.

Systemic memory T cells are characterized according to the cell surface expression of certain known antigens. Typically, these cells are positive for CD4, and lack expression of CD45RA, and integrin $\alpha 4\beta 7$. They are further characterized by expression of CCR4. A subset of cells of interest are common leukocyte antigen positive ($CLA^+$). Verification of the identity of the cells of interest may be performed by any convenient method, including antibody staining and analysis by fluorescence detection, ELISA, etc., reverse transcriptase PCR, transcriptional amplification and hybridization to nucleic acid microarrays, etc. Some memory T cells associated with the skin are known to express CLA. Thus, any type of cell can be identified when necessary.

Other systemic memory cells are triggered to adhere to endothelial ICAM-1, by LFA-1 binding. These adhesion molecules are implicated in graft rejection, psoriasis, and arthritis. In a preferred embodiment, systemic memory T cells are killed by the co-administration of rapamycin to a patient that has received an organ, tissue or cell transplant. Without, wishing to be bound by theory, removal of memory T cells decreases a cell mediated immune rejection of an allograft. However, rapamycin or a rapamycin derivative compound can be administered together with other agents such as for example, CCR4 blocking agents that prevents triggering of LFA-1 mediated adhesion is useful in the inhibition of graft rejection by preventing the accumulation of memory T cells at the site of graft implantation; preventing intra-islet infiltration by T cells to inhibit development of insulin-dependent diabetes mellitus; blocking infiltration of T cells into the central nervous system to treat multiple sclerosis and other demyelinating diseases; blocking the accumulation of T cells in the synovial joints of patients suffering from rheumatoid arthritis; accumulation of memory T cells to influence immune responsiveness, and the like.

Immune cells express a variety of cell surface molecules which can be detected with either monoclonal antibodies or polyclonal antisera. Immune cells that have undergone differentiation or activation can also be enumerated by staining for the presence of characteristic cell surface proteins by direct immunofluorescence in fixed smears of cultured cells.

T lymphocytes, at whichever stage of maturity and cell differentiation expressing CD62L can be identified. For example, one such method is by measuring cell phenotypes. The phenotypes of immune cells and any phenotypic changes can be evaluated by flow cytometry after immunofluorescent staining using monoclonal antibodies that will bind membrane proteins characteristic of various immune cell types.

A second means of assessing cell differentiation is by measuring cell function. This may be done biochemically, by measuring the expression of enzymes, mRNA's, genes, proteins, or other metabolites within the cell, or secreted from the cell. Bioassays may also be used to measure functional cell differentiation or measure specific antibody production directed at a patient's tumor, tumor cell lines or cells from fresh tumors.

Preferably, rapamycin or a rapamycin derivative enhances the generation of other therapeutic cells such as, for example, dendritic cells, pluripotent stem cells, or hematopoietic stem cells. Rapamycin-generated dendritic cells would, for example, improve cellular immune therapy strategies, as the dendritic cells can be pulsed with tumor or infectious disease antigens to more optimally generate an effective T cell immune response. Purified dendritic cells can be pulsed with (exposed to) antigen, to allow them to take up the antigen in a manner suitable for presentation to other cells of the immune systems. Antigens are classically processed and presented through two pathways. Peptides derived from proteins in the cytosolic compartment are presented in the context of Class I MHC molecules, whereas peptides derived from proteins that are found in the endocytic pathway are presented in the context of Class II MHC. However, those of skill in the art recognize that there are exceptions; for example, the response of $CD8^+$ tumor specific T cells, which recognize exogenous tumor antigens expressed on MHC Class I. A review of MHC-dependent antigen processing and peptide presentation is found in Germain, R. N., Cell 76:287 (1994).

Numerous methods of pulsing dendritic cells with antigen are known; those of skill in the art regard development of suitable methods for a selected antigen as routine experimentation. In general, the antigen is added to cultured dendritic cells under conditions promoting viability of the cells, and the cells are then allowed sufficient time to take up and process the antigen, and express antigen peptides on the cell surface in association with either Class I or Class II MHC, a period of about 24 hours (from about 18 to about 30 hours, preferably 24 hours). Dendritic cells may also be exposed to antigen by transfecting them with DNA encoding the antigen. The DNA is expressed, and the antigen is presumably processed via the cytosolic/Class I pathway.

The present invention provides methods of using therapeutic compositions comprising activated, antigen-pulsed dendritic cells. The use of such cells in conjunction with soluble cytokine receptors or cytokines, or other immunoregulatory molecules is also contemplated. The inventive compositions are administered to stimulate an allogeneic immune response, and can be given by bolus injection, continuous infusion, sustained release from implants, or other suitable technique. Typically, the cells will be administered in the form of a composition comprising the antigen-pulsed, activated dendritic cells in conjunction with physiologically acceptable carriers, excipients or diluents. Such carriers will be nontoxic to recipients at the dosages and concentrations employed. Neutral buffered saline or saline mixed with serum albumin are exemplary appropriate diluents.

Ex Vivo Culture of Dendritic Cells

A procedure for ex vivo expansion of hematopoietic stem and progenitor cells is described in U.S. Pat. No. 5,199,942, incorporated herein by reference. Other suitable methods are known in the art. Briefly, ex vivo culture and expansion comprises: (1) collecting $CD34^+$ hematopoietic stem and progenitor cells from a patient from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used.

Stem or progenitor cells having the CD34 marker constitute only about 1% to 3% of the mononuclear cells in the bone marrow. The amount of $CD34^+$ stem or progenitor cells in the peripheral blood is approximately 10- to 100-fold less than in bone marrow. Cytokines such as flt3-L may be used to increase or mobilize the numbers of dendritic cells in vivo. Increasing the quantity of an individual's dendritic cells may facilitate antigen presentation to T cells for antigen(s) that already exists within the patient, such as a tumor antigen, or a bacterial or viral antigen. Alternatively, cytokines may be administered prior to, concurrently with or subsequent to administration of an antigen to an individual for immunization purposes.

Peripheral blood cells are collected as described in the Examples which follow or, alternatively, can be using procedures known in the art such as, for example, apheresis procedures. See, for example, Bishop et al., *Blood*, vol. 83, No. 2, pp. 610-616 (1994). Briefly, peripheral blood progenitor cells (PBPC) and peripheral blood stem cells (PBSC) are collected using conventional devices, for example, a Haemonetics Model V50 apheresis device (Haemonetics, Braintree, Mass.). Four-hour collections are performed typically no more than five times weekly until approximately $6.5 \times 10^8$ mononuclear cells (MNC)/kg are collected. The cells are suspended in standard media and then centrifuged to remove red blood cells and neutrophils. Cells located at the interface between the two phases (the buffy coat) are withdrawn and resuspended in HBSS. The suspended cells are predominantly mononuclear and a substantial portion of the cell mixture are early stem cells.

A variety of cell selection techniques are known for identifying and separating $CD34^+$ hematopoietic stem or progenitor cells from a population of cells. For example, monoclonal antibodies (or other specific cell binding proteins) can be used to bind to a marker protein or surface antigen protein found on stem or progenitor cells. Several such markers or cell surface antigens for hematopoietic stem cells (i.e., flt-3, CD34, My-10, and Thy-1) are known in the art, as are specific binding proteins.

In one method, antibodies or binding proteins are fixed to a surface, for example, glass beads or flask, magnetic beads, or a suitable chromatography resin, and contacted with the population of cells. The stem cells are then bound to the bead matrix. Alternatively, the binding proteins can be incubated with the cell mixture and the resulting combination contacted with a surface having an affinity for the antibody-cell complex. Undesired cells and cell matter are removed providing a relatively pure population of stem cells. The specific cell binding proteins can also be labeled with a fluorescent label, e.g., chromophore or fluorophore, and the labeled cells separated by sorting. Preferably, isolation is accomplished by an immunoaffinity column.

Immunoaffinity columns can take any form, but usually comprise a packed bed reactor. The packed bed in these bioreactors is preferably made of a porous material having a substantially uniform coating of a substrate. The porous material, which provides a high surface area-to-volume ratio, allows for the cell mixture to flow over a large contact area while not impeding the flow of cells out of the bed. The substrate should, either by its own properties, or by the addition of a chemical moiety, display high-affinity for a moiety found on the cell-binding protein. Typical substrates include avidin and streptavidin, while other conventional substrates can be used.

In one useful method, monoclonal antibodies that recognize a cell surface antigen on the cells to be separated are typically further modified to present a biotin moiety. The affinity of biotin for avidin thereby removably secures the monoclonal antibody to the surface of a packed bed (see Berenson, et al., *J. Immunol. Meth.*, 91:11, 1986). The packed bed is washed to remove unbound material, and target cells are released using conventional methods. Immunoaffinity columns of the type described above that utilize biotinylated anti-CD34 monoclonal antibodies secured to an avidin-coated packed bed are described for example, in WO 93/08268.

An alternative means of selecting the quiescent stem cells is to induce cell death in the dividing, more lineage-committed, cell types using an antimetabolite such as 5-fluorouracil (5-FU) or an alkylating, agent such as 4-hydroxycyclophosphamide (4-HC). The non-quiescent cells are stimulated to proliferate and differentiate by the addition of growth factors that have little or no effect on the stem cells, causing the non-stem cells to proliferate and differentiate and making them more vulnerable to the cytotoxic effects of 5-FU or 4-HC. See Berardi et al., *Science,* 267:104 (1995), which is incorporated herein by reference.

Isolated stem cells can be frozen in a controlled rate freezer (e.g., Cryo-Med, Mt. Clemens, Mich.), then stored in the vapor phase of liquid nitrogen using dimethylsulfoxide as a cryoprotectant. A variety of growth and culture media can be used for the growth and culture of dendritic cells (fresh or frozen), including serum-depleted or serum-based media. Useful growth media include RPMI, TC 199, Iscoves modified Dulbecco's medium (Iscove, et al., F. *J. Exp. Med.*, 147: 923 (1978)), DMEM, Fischer's, alpha medium, NCTC, F-10, Leibovitz's L-15, MEM and McCoy's. Particular nutrients present in the media include serum albumin, transferrin, lipids, cholesterol, a reducing agent such as 2-mercaptoethanol or monothioglycerol, pyruvate, butyrate, and a glucocorticoid such as hydrocortisone 2-hemisuccinate. More particularly, the standard media includes an energy source, vitamins or other cell-supporting organic compounds, a buffer such as HEPES, or Tris, that acts to stabilize the pH of the media, and various inorganic salts. A variety of serum-free cellular growth media is described in WO 95/00632, which is incorporated herein by reference. The collected $CD34^+$ cells are cultured with suitable cytokines, for example, as described herein. $CD34^+$ cells then are allowed to differentiate and commit to cells of the dendritic lineage. These cells are then further purified by flow cytometry or similar means, using markers characteristic of dendritic cells, such as CD1a, HLA DR, CD80 and/or CD86. The cultured dendritic cells are exposed to an antigen, for example, an allogeneic class I HLA molecule, allowed to process the antigen, and then cultured with an amount of a CD40 binding protein to activate the dendritic cell. Alternatively, the dendritic cells are transfected with a gene encoding an allogeneic HLA class I molecule or immune related receptors, and then cultured with an amount of a CD40 binding protein to activate the antigen-presenting dendritic cells.

The activated, antigen-carrying dendritic cells are them administered to an individual in order to stimulate an antigen-specific immune response. The dendritic cells can be administered prior to, concurrently with, or subsequent to, antigen administration. Alternatively, T cells may be collected from the individual and exposed to the activated, antigen-carrying dendritic cells in vitro to stimulate antigen-specific T cells, which are administered to the individual.

Rapamycin-generated pluripotent stem cells would have particular application for stem cell therapy, which includes for example, the treatment of a wide variety of diseases such as Parkinson's Disease, post cerebral vascular accident neurological deficiency, type I diabetes mellitus, and post myocardial infarction deficiency. Rapamycin-generated hematopoietic stem cells would have particular application to the use of hematopoietic stem cell transplantation, which includes therapeutic application for the treatment of immune deficiency syndromes, auto-immune disease, hematologic malignancy, and solid tumors. In each of these embodiments detailed in this invention, the relevant starting cell population is, for example, precursor monocytes or hematopoietic stem cells in the case of dendritic cell therapy. Preferably, highly purified pluripotent stem cells if the desired cell is for use in stem cell therapy. Preferably, CD34+ hematopoietic stem cells are used in the case of hematopoietic stem cell therapy.

The cells are placed into in vitro culture conditions, described herein, in the presence of rapamycin. In each case the cell culture in the presence of rapamycin is performed in the presence of suitable cytokines. For example, for dendritic cell expansion in the presence of rapamycin, the dendritic cells are preferably propagated in cytokines such as IL-4 and GM-CSF. In the case of pluripotent or hematopoeitic stem cell culture in the presence of rapamycin, cytokine additives to the culture comprise, for example, recombinant stem cell factor, IL-3, IL-6, GM-CSF, G-CSF, IL-7, or other recombinant cytokines.

Any cell can be used in the methods of the invention, including but not limited to, stem cells, thymocytes, precursor cells and the like. A precursor cell population includes cells of a mesodermal derived cellular lineage, more particularly of hematopoietic lineage, endothelial lineage, muscle cell lineage, epithelial cell lineage and neural cell lineage.

A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

As used herein, the term "population" refers to cells having the same or different identifying characteristics. The term "lineage" refers to all of the stages of the development of a cell type, from the earliest precursor cell to a completely mature cell (i.e. a specialized cell).

Preferred cells within a stem cell population of the present invention include cells of at least one of the following cellular lineages: hematopoietic cell lineage, erythroid lineage, endothelial lineage, leukocyte lineage, thrombocyte lineage, erythroid lineage (including primitive and definitive erythroid lineages), macrophage lineage, neutrophil lineage, mast cell lineage, megakaryocyte lineage, natural killer cell lineage, eosinophil lineage, T cell lineage, endothelial cell lineage and B cell lineage.

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells will be removed.

Procedures for separation may include but are not limited to, magnetic separation, using antibody-coated magnetic beads, affinity chromatography, cytotoxic agents joined to a monoclonal antibody or used in conjunction with a monoclonal-antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

In another preferred embodiment, cells are isolated and purified cell from a sample, patient or donor individual and are used in functional assays to determine any properties of the cells. Depending on the isolated and purified cellular population, appropriate functional assays known in the art can be conducted. For example, if the population of cells are T cells specific for a desired antigen such as a tumor antigen, cytotoxic T cell assays, T cell proliferation assays, cytokine profiles, determination of surface antigens for T cell maturity or memory T cells, etc., can be carried out.

Isolation of cells useful in the present invention are well known in the art. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. T cells or B cells can be enriched or depleted, for example, by positive and/or negative selection using antibodies to T cell or B cell surface markers, for example by incubating cells with a specific primary monoclonal antibody (mAb), followed by isolation of cells that bind the mAb using magnetic beads coated with a secondary antibody that binds the primary mAb. Peripheral blood or bone marrow derived hematopoietic stem cells can be isolated by similar techniques using stem cell-specific mAbs (e.g., anti-CD34 mAbs). Specific cell populations can also be isolated by fluorescence activated cell sorting according to standard methods. Monoclonal antibodies to cell-specific surface markers known in the art and many are commercially available.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells can be removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

In one preferred embodiment, rapamycin resistant allogeneic cells are administered to a patient. Allogeneic cells may be derived from any person and comprise both $CD4^+$ and $CD8^+$ T cells. Cells are treated with the desired cytokines and rapamycin prior to administering to a patient.

An advantage of the present invention is that the peripheral pool of memory T cells ($CD45RO^+$) are susceptible to rapamycin or a rapamycin derivative compound and are inhibited, thereby decreasing the risk of GVHD. Conversely, the naive T cell repertoire ($CD45RA^+$) is maintained. For example, to evaluate the frequency of resting T cells with memory phenotype that could be stimulated by cytokines to grow, limiting dilution experiments can be performed. $CD45RO^+CD4^+$ resting T cells can be cultured with IL-2 alone or in combination with TNF-α and IL-6, in the presence of autologous irradiated macrophages and anti-DR antibodies to prevent autoreactive responses. The in vitro expansion of immune T cells with a more naïve phenotype may be particularly applicable to the therapy of autoimmune disease. In a therapeutic plan, patients with autoimmune disease may undergo apheresis to isolate T cells, have T cells expanded in rapamycin to enrich for a naïve T cell phenotype, receive immune depleting chemotherapy to eliminate autoreactive T cell clones in vivo, and then receive infusion of in vitro generated T cells from immune reconstitution with a T cell source less likely to reconstitute autoimmunity (T cells with characteristics more typical of naïve T cells; i.e., $CD28^+$, $CD62L^+$).

The allogeneic cells contained in the medicament of the invention may assume any formation. For example, the allogeneic cells suspended in an adequate solution may be used. The solution containing the allogeneic cells can desirably be used as an injection or drip-feed solution. Especially, an injection or drip-feed solution, which is prepared by suspending the allogeneic cells in physiological saline and so on containing about 0.01% to 5% of human serum albumin. The allogeneic cells or the preparations containing them may be frozen and kept in their frozen state so as to be used for remedying or preventing various disease. Cryopreservation should be performed under liquid nitrogen conditions, preferably in solutions that preserve immune T cell function, such as reduced DMSO concentrations of 5% and addition of cryopreservant molecules such as pentastarch.

When the medicaments according to the invention can desirably be administered to a patient by an intravenous drip, arterial injection, local injection and the like. The desirable dosage of the medical solution varies in accordance with the way or place of the administration thereof. However, it is commonly desirable to administer at least about 50 to about 500 ml of the medical solution containing the allogeneic cells in the aforesaid ratio to the patient. It is preferable that the medical solution is administered one time a day to one time a month. In any event, at least one administration of the medicament comprising the allogeneic cells should be made. In the allogeneic setting, the T cells are administered at the time of the HSCT (within 24 hours of stem cell infusion), and can be administered at the time of any other donor T cell infusion, for example, at the time of a donor lymphocyte infusion (DLI).

The dosage of the allogeneic cells contained, as the main ingredient, in the medicament of the invention, may be arbitrarily decided in accordance with the condition of the patient and/or the clinical procedure. In general, about $1 \times 10^2$ to about $1 \times 10^9$ allogeneic cells per kilogram of patient's weight may be used.

The extraction of cells from the donor may be performed any way, for example, by blood collection, pheresis, or other possible operations. It is desirable to draw blood from the vein of the donor, and add heparin or citric acid to the blood thus drawn to prevent blood coagulation. The blood of the order of 0.01 ml to 100 ml is generally drawn in one blood extraction operation, but the amount of the blood to be drawn is not limited in the invention. Taking into consideration the physical burden of the donor, labors involved in collecting the blood, and troublesome operations for separating the lymphocyte cells, it is desirable to draw the blood by 5 ml to 10 ml, preferably 10 ml to 20 ml in one blood extraction operation. For most clinical applications, harvest of sufficient numbers of autologous or allogeneic T cells will require an outpatient apheresis procedure.

The operation for separating the lymphocyte cells from the blood drawn in the aforementioned manner may be accomplished by a known method for separating lymphocyte cells such as a discontinuous density gradient centrifugation method which is performed by using sucrose or lymphocyte separating agents on the market. Alternatively, the apheresis product can be subjected to counterflow centrifugal elutriation as a mechanism to enrich for lymphocyte populations. Furthermore, such lymphocytes can be enriched for the desired T cell subset by negative or positive selection using antibodies and selection beads or selection columns.

The type of the anti-CD3 antibodies used in the invention is not limited to a specific antibody, as far as the antibody makes for proliferation and activation of the desired lymphocyte cells. The anti-CD3 antibodies used for stimulating the lymphocyte cells are possibly yielded in organisms or organic cells by use of refined CD3 molecules.

As the culture medium solution for cultivating the desired cells, there may be used a culture medium derived from a living organism or a culture medium composed by mixing amino acid, vitamins, nucleic acid base and the like with equilibrium salt solution. For example, as the culture medium, RPMI-1640, AIM-V, DMEM, IMDM, X-Vivo 15, or X-Vivo 20 or the like are preferable. In particular, the culture medium of X-Vivo 20 is particularly recommended for expansion of human T cells under the conditions identified here. Such media is further supplemented by the addition of 5% autologous plasma, or 5% human A/B serum. These culture medium components applicable to the invention are commercially available.

The cultivation of the desired cells may be fulfilled by common cell-cultivating methods. For example, it can be carried out in a $CO_2$-incubator at a $CO_2$ concentration of about 1% to about 10%, preferably about 5%, at a temperature of 30° C. to 40° C., most preferred at about 37° C.

The number of days which the cultivation takes place is not specifically restricted, but it is desirable to allow about 2 to about 20 days. For the human condition, a period of about 20 days appears sufficient to achieve the desired T cell cytokine phenotype and to achieve clinically relevant T cell numbers. Such cells appear to be stable, with appropriate re-stimulation with anti-CD3 and anti-CD28 molecules, for several weeks after day 20, and such an expansion may prove valuable in some circumstances that require increased cell number or further in vitro modifications. For example, it may be desirable to first initiate a polyclonal expansion in rapamycin to alter the T cell phenotype towards a naïve T cell character, and then to perform further stimulations in an antigen-specific manner in an attempt to enhance reactivity to cancer or infectious disease antigens. Within the period for the cultivation, it is best to observe the conditions of the cells under a microscope and take count of the number of cells so as to suitably adjust the amount of the culture medium solution by adding the solution. The proliferation of the cells does not appreciably take place within about 1 to about 2 days after commencement of the cultivation, but is generally observed about 3 to six days after the commencement. When the cells are satisfactorily proliferated, the color of the culture medium solution will be changed from orange to yellow. The culture medium is supplemented at about 0.1 to about 5 times the culture solution initially given. It is preferred to monitor the cell number and median cell volume by Coulter Multisizer evaluation daily, as this approach allows accurate determination of T cell expansion and T cell activation.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

EXAMPLES

Materials and Methods

Purification of T Cells

Murine $CD4^+$ splenic T cells from C57Bl/6 mice were purified to >98% purity by negative selection using anti-macrophage, anti-B cell, anti-CD8 cell, and anti-granulocyte antibodies (StemCell Technologies; murine CD4+ T cell enrichment procedure). Murine CD4 cells were plated at a concentration of $0.2 \times 10^6$ cells/ml in RPMI-1640 media supplemented with 10% fetal calf serum (Gemini Bioproducts).

Activation of T Cells and Culture Conditions $CD4^+$ cells were stimulated with magnetic beads (tosylated beads; Dynal) that were coated with anti-murine CD3 PharMingen) and anti-murine CD28 (PharMingen) at a T cell to bead ratio of 1:3. Media in the Th1 condition consisted of recombinant murine IL-12 (2.5 ng/ml; R and D Systems), anti-murine IL-4 neutralizing antibody (clone 11B11; 10 micrograms/ml), recombinant human IL-2 (20 I.U./ml; Chiron), recombinant human IL-7 (20 ng/ml; Peprotech), and the anti-oxidant N-acetyl cysteine (NAC; 3.3 µM. Media in the Th2 condition consisted of recombinant murine IL-4 (1000 I.U./ml; Peprotech), recombinant human IL-2 (20 I.U./ml), recombinant human IL-7 (20 ng/ml), and 3.3 µM NAC.

Immune suppression molecules cyclosporine A (CSA), FK506, and rapamycin were purchased from Sigma and reconstituted according to the manufacturers instructions, with rapamycin and FK506 being tested at 0.004 µM and 0.02 µM concentrations and CSA being tested at 0.04 µM and 0.2 µM concentrations. Media containing IL-2, IL-7, NAC, and the particular immune suppression agent was added to maintain cell concentration at between 0.2 and $1.0 \times 10^6$ cell/ml throughout the culture interval. Cells were counted by a Multi-Sizer Instrument (Coulter), and CD4 expansion is plotted, as shown in FIG. 1.

Lymphocyte Harvest and T Cell Isolation from Human Donors

After determination that the donor is HLA-matched with recipient, the donor undergoes a 2 to 5 liter apheresis procedure using a CS-3000 or an equivalent machine. The apheresis product is subjected to counterflow centrifugal elutriation by standard operating procedures of the NIH Department of Transfusion Medicine, Cell Processing Section. The lymphocyte fraction of the elutriation product (120 to 140 fraction) is depleted of B cells by incubation with an anti-B cell antibody (anti-CD20; Nexell) and an anti-CD8 antibody (Nexell) and sheep anti-mouse magnetic beads (Dynal; obtained through Nexell) by standard operating procedures using the MaxCep Device (Nexell). Flow cytometry will be performed to document that $CD8^+$ T cell contamination is <1%. The resultant CD4-enriched donor lymphocyte product can be cryopreserved in aliquots of 50 to $200 \times 10^6$ cells/vial. Sterility of the population is not tested at this early stage of the Th2 cell generation procedure; such testing occurs after final co-culture of donor CD4 cells.

Peripheral Blood Stem Cell Harvest from Donor

Immediately following lymphocyte harvest, the donor will receive filgrastim as an outpatient (10 µg/kg/day each morning; subcutaneously) for 5, 6, or 7 days. The donor should take the filgrastim as early as possible upon awakening in the morning. This is especially important on days 5, 6, and 7 of the injections.

Apheresis is typically performed on days 5 and 6 of this regimen. On some occasions, sufficient numbers of $CD34^+$ cells might be obtained with a single apheresis on day 5; on other occasions, it may be necessary to perform apheresis on days 5, 6, and 7 to reach the target $CD34^+$ cell number ($\geq 4 \times 10^6$ per kg). The donor is instructed to take filgrastim for the complete 7 day period, unless notified by the transplant team that adequate $CD34^+$ cells were harvested before day 7. If $\geq 3 \times 10^6$ CD34+ cells per kg are harvested after apheresis on days 5, 6, and 7, no further mobilization or apheresis is performed, and the patient is eligible to receive the stem cell transplant with that dose of CD34+ cells. In the event that less than $3 \times 10^6$ $CD34^+$ cells per kg are harvested after apheresis on days 5, 6, and 7, the donor will be given two weeks of rest, and then will be re-treated with filgrastim followed by repeat peripheral blood stem cell harvesting. A 15 to 25 liter large volume whole blood pheresis is performed via a 2-armed approach or via a temporary central venous catheter in the femoral position using the Baxter CS3000Plus, Cobe Spectra, or an equivalent instrument. This procedure typically takes 4 to 6 hours.

The apheresis procedure typically uses ACD-A anti-coagulant; alternatively, partial anti-coagulation with heparin may be utilized. The apheresis product can be cryopreserved and stored at −180 degrees Celsius in a solution containing Plasmalyte A, Pentastarch, human serum albumin, DMSO, and preservative free heparin (10 U/ml). The concentration of $CD34^+$ cells in the apheresis product is determined by flow cytometry, and the number of $CD34^+$ cells in each cryopreserved bag calculated. If the donor and host are ABO incompatible, red blood cells will be depleted from the stem cell product by standard protocols.

In Vitro Generation of Donor CD4+ Th2 Cells

Cryopreserved donor $CD4^+$ T cells are resuspended to a concentration of $0.3 \times 10^6$ cells per ml. Media consist of X-Vivo 20 supplemented with 5% heat-inactivated autologous plasma. The donor $CD4^+$ T cells are cultured in filtered flasks at 37° C. in 5% $CO_2$ humidified incubators. At the time of culture initiation, T cells are stimulated with anti-CD3/anti-CD28 coated magnetic beads (3 to 1 ratio of beads to T cells). At the time of co-culture initiation and on day 2 of culture, the following reagents are added: recombinant human IL-4 (Shering IL-4; 1000 I.U. per ml), and recombinant human IL-2 (purchased from Chiron Therapeutics; 20 I.U. per ml). After day 2, cells are maintained at a concentration of 0.25 to $1.0 \times 10^6$ cells per ml by the addition of fresh X-Vivo 20 media supplemented with autologous plasma (5%), IL-2 (20 I.U./ml), and IL-4 (1000 I.U./ml). The median cell volume is determined using a Multisizer II instrument (Coulter). When the T cell volume approaches 500 fl (acceptable range of 650 to 350), the T cells are restimulated with anti-CD3/anti-CD28 beads; typically, this time of restimulation will be after 8 to 12 days of culture. Bead restimulation is at a bead to T cell ratio of 3:1. T cell concentration is $0.2 \times 10^6$ cells/ml. Media consists of X-Vivo 20 supplemented with autologous plasma (5%), IL-2 (20 I.U./ml), and IL-4 (1000 I.U./ml). After bead restimulation, CD4 cells are maintained at a concentration of 0.25 to $1.0 \times 10^6$ cells per ml by the addition of fresh X-Vivo 20 media supplemented with autologous plasma (5%), IL-2 (20 I.U./ml), and IL-4 (1000 I.U./ml). Rapamycin (commercially available oral solution; Sirolimus, Wyeth-Ayerst) is added to the Th2 culture condition at day 0 at a concentration of 1 micromolar. For some donors who are particularly sensitive to the effects of rapamycin, it may be necessary to initiate culture in lower doses of rapamycin, such as 0.01 to 0.1 micromolar. When the Th2 culture media is expanded for the purposes of cytokine addition or maintenance of cell concentration at 0.2 to $1.0 \times 10^6$ cells/ml, the media added to culture should be replete with rapamycin, and contain a concentration of rapamycin between 0.01 and 1.0 micromolar. The highest concentration of rapamycin that allows CD4 Th2 cell expansion should be utilized. In the case of Th2 generation in rapamycin, it is typically not necessary to restimulate the CD4 cells with anti-CD3 and anti-CD28, as the cells have attained a purified Th2 phenotype after only one round of CD3, CD28 co-stimulation. This methodology therefore allows rapid and uncomplicated generation of Th2 cells and represents a technical advance that allows Th2 generation with reduced reagent utilization and reduced labor.

When the CD4 cell mean cell volume approaches 500 fl (acceptable range of 650 to 350), the cells are harvested and cryopreserved.

The following is the minimal phenotypic requirements of any particular Th2 cell culture to qualify for cryopreservation with subsequent administration:

1. Presence of predominately CD4+ T cells by flow cytometry (greater than 70% CD4+ T cells, and less than 5% contaminating CD8+ T cells).

2. In addition, the cryopreserved product is tested for sterility with both fungal and bacterial cultures, through the ongoing testing done on cell products processed in the NIH Department of Transfusion Medicine. In addition, the CD4 Th2 cell product is tested for endotoxin content by the limulus assay. Cell products positive for fungal, bacterial, or endotoxin content are discarded.

Transplant Procedure: Allogeneic Peripheral Blood Stem Cell Transplantation a) On day 0, the patient receives the cryopreserved PBSC.

b) The cryopreserved PBSC product is thawed and administered intravenously immediately. The target dose of the PBSC is $\geq 4 \times 10^6$ CD34+ cells per kg.

However, if donor apheresis on days 5, 6, and 7 yields a total of $\geq 3 \times 10^6$ CD34+ cells per kg, this level of CD34+ cell dose is also allowed.

(c) No steroids are allowed in the management of DMSO-related toxicities (chills, muscle aches) that may occur immediately after cellular infusion (diphenhydramine and meperidine are allowed).

(d) In the case of rapamycin generated Th2 cells, standard GVHD prevention strategy may involve either the standard calcineurin inhibitor drugs cyclosporine A or FK506, or most preferably, in vivo rapamycin.

Transplant Procedure: Donor Th2 Cell Administration a) On day 1 of the transplant procedure, the cryopreserved donor Th2 cells are thawed and immediately administered intravenously.

b) No steroids are allowed in the management of DMSO-related toxicities (chills, muscle aches) that may occur immediately after cellular infusion (diphenhydramine and meperidine are allowed).

c) The determination of whether a Th2 cell infusion is safe will be based on the presence or absence of hyperacute GVHD and of any grade 4 or 5 toxicity attributable to the Th2 cells that occurs in the first 14 days post-transplant.

d) Hyperacute GVHD is defined as a severe level of acute GVHD (grade III or IV) that occurs within the first 14 days post-transplant.

e) The initial three patients to be enrolled to Th2 cell dose level #1 ($5 \times 10^6$ Th2 cells/kg). If no hyperacute GVHD or grade 4 or 5 toxicity attributable to the Th2 cells is observed in these initial three patients, then it will be determined that this dose level is safe, and accrual to dose level #2 will commence. If hyperacute GVHD or grade 4 or 5 toxicity attributable to the Th2 cells is observed in any of the initial three patients, then accrual to dose level #1 will be expanded to include a total of six patients. If two patients in six develop hyperacute GVHD or a grade IV toxicity related to the Th2 cells, then it will be determined that dose level #1 is not safe, and further accrual to the study will stop at that point. If only one of the six patients experiences such an adverse effect, then it will be determined that dose level #1 is safe, and accrual will proceed to dose level #2.

f) Three patients may then be enrolled to Th2 cell dose level #2 ($2.5 \times 10^7$ Th2 cells/kg). The same accrual and stopping rules will apply to this dose level as those used for dose level #1. As such, either three or six patients will be accrued to dose level #2.

g) If it is determined that Th2 cell dose level #2 is safe, accrual to the final dose level #3 will start (Th2 cell dose of $1.25 \times 10^8$ cells/kg). Six patients in total will be evaluated on dose level #3. If more than one patient on dose level #3 develops hyperacute GVHD or grade 4 or 5 toxicity attributable to the Th2 cells, then accrual to dose level #3 will stop.

h) In the phase II component of this study, eighteen (18) additional patients will receive Th2 cells at either dose level #2 or level #3. To help ensure that the Th2 cells continue to be safely administered in this expanded cohort, the same accrual and stopping rules pertaining to severe toxicity attributed to the Th2 cells will be continued. Specifically, 24 total patients (6 in the Phase I cohort, 18 in the expanded Phase II cohort) will be evaluated at either Th2 cell dose level #2 or level #3. Accrual and stopping rules will be applied after each cohort of six patients. Therefore, if at any point, the frequency of severe toxicity attributable to the Th2 cells exceeds 1/6, 2/12, 3/18, or 4/24, then accrual to that treatment arm will be stopped.

Example 1

CD4+ Th1/Th2 Modulation

Use of the calcineurin inhibitors cyclosporine A or FK506 is a standard component of immune suppression after allogeneic PBSCT. Given the known role of Th1/Th2 biology in the modulation of immunity post-SCT, it is an important goal to identify any differential influence of these two agents on the Th1/Th2 balance. In addition to CSA and FK506, rapamycin is an immune suppression agent that has been studied in murine models, and more recently, in clinical trials of allogeneic PBSCT. Rapamycin, by binding to the mammalian target of rapamycin, controls multiple aspects of T cell metabolism, including phosphorylation of Rb protein with subsequent regulation of cyclin dependent kinases and control of protein translation via the 14-3-3 pathway. As such, the mechanism of action of rapamycin stands in stark contrast to that of CSA and FK506, which work primarily through inhibition of cytokine and other molecule mRNA transcription. To this extent, a thorough evaluation and comparison of these three molecules as they relate to the modulation of Th1/Th2 biology is warranted, particularly as it relates to immunity in the allogeneic PBSCT context.

In FIG. 1, results are shown that illustrate the differential effect of CSA, FK506, and rapamycin on the generation of murine CD4+ Th1 and Th2 cells. Murine CD4 cells were purified, stimulated in a polyclonal manner with anti-CD3 and anti-CD28 antibodies, and propagated in culture conditions that promote either Th1 or Th2 differentiation. For Th1 cultures, media was supplemented with IL-12, antibody to IL-4, IL-2, IL-7, and the cell death inhibitor N-acetyl cysteine; for Th2 cultures, media was supplemented with IL-4, IL-2, IL-7, and NAC. As FIG. 1 shows, control Th1 and Th2 cell cultures expanded approximately 2 to 3 logs in six days. In contrast, Th1 or Th2 expansion in the presence of either 0.004 μM or 0.02 μM of FK506 was associated with a dramatic reduction in CD4 cell expansion under these optimized conditions; in both Th1 or Th2 conditions, there was only a two to three fold increase in CD4 cell number in the presence of FK506. Presence of CSA at either 0.04 μM or 0.2 μM concentrations yielded a similar inhibition of Th1 and Th2 expansion. As such, there did not appear to be any preferential Th2 or Th1 generation with the calcineurin inhibitors. Remarkably, at concentrations of rapamycin that in the literature have previously been associated with T cell inhibition (0.004 μM and 0.02 μM), no significant inhibition in CD4+ T cell expansion under either Th1 or Th2 conditions, was observed. In fact, Th1 and Th2 expansion under the 0.02 μM concentration of rapamycin actually resulted in an increased CD4 cell number relative to the Th1 and Th2 control cultures.

Example 2

Evaluation of Immunosuppressive Agents on Th2 Responses

To evaluate for Th2-bias relative to the three immune suppression agents, CSA, FK506, and rapamycin, on day 6 after Th2 expansion, the CD4 cells were harvested from culture, washed, normalized to a concentration of $0.5 \times 10^6$ cells/ml, and re-stimulated with anti-CD3 and anti-CD28 for supernatant generation. On day 6 of culture, T cells were harvested, washed, normalized to a concentration of $0.5 \times 10^6$ cells/ml, and re-stimulated with anti-CD3 and anti-CD28 (3:1 bead to T cell ratio) for 24 hours to generate a supernatant. Culture supernatants were tested for IL-4 and IL-10 content by a two site ELISA (BioSource), with experimental samples scored relative to a standard curve generated from evaluation of recombinant murine IL-4 and IL-10. Cell culture labels along the x-axis represent cytokine and immune suppression agent conditions during the initial six days of T cell generation; there were no cytokines or immune suppression agents added during the time of 24 hour supernatant generation.

Figure 2:
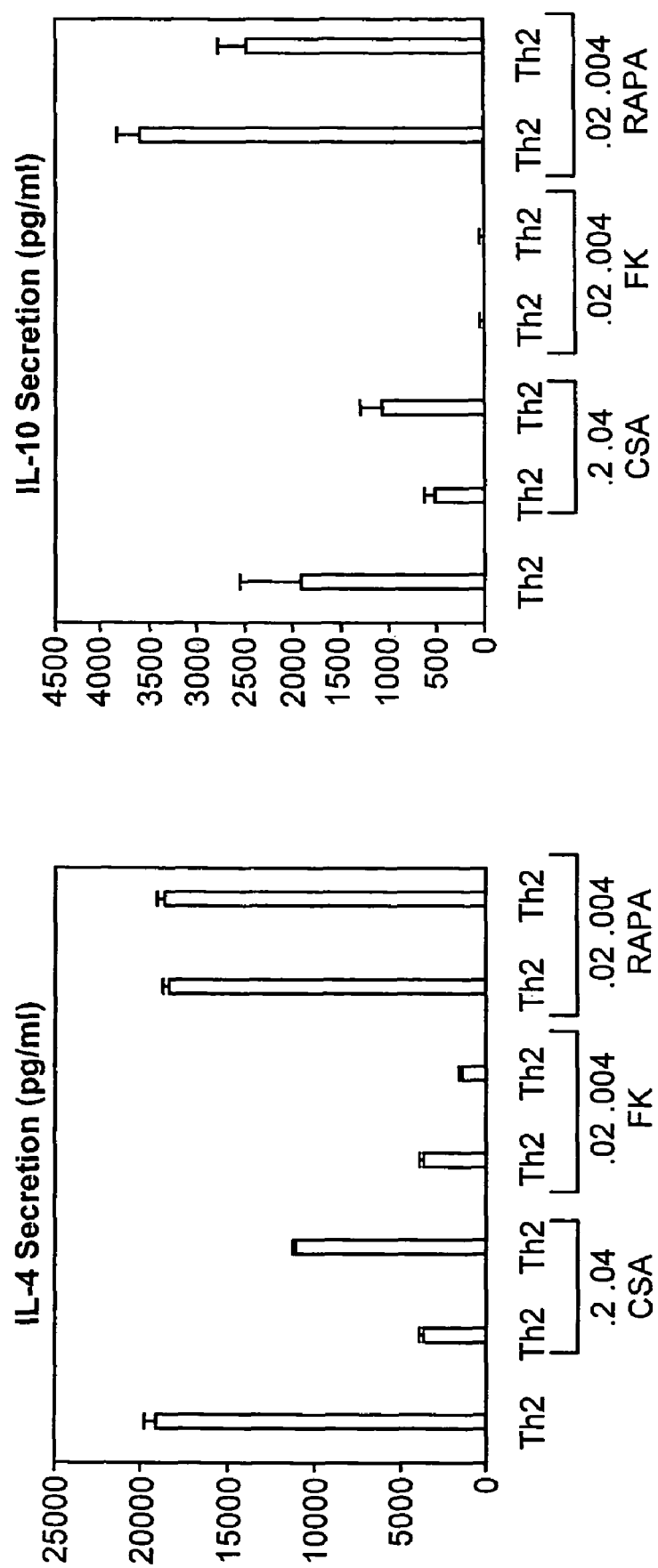
FIG. 2 is a graph showing supernatant ELISA results for the type II cytokines IL-4 and IL-10.

FIG. 2 shows supernatant ELISA results for the type II cytokines IL-4 and IL-10. Th2 expansion in the presence of CSA, and in particular, in the presence of FK506, reduced the capacity of the CD4 cells to produce IL-4 and IL-10 relative to the control Th2 culture. In contrast, Th2 expansion in the presence of rapamycin resulted in Th2 cells with similar IL-4 and IL-10 secretion relative to the control. As such, rapamycin, but not CSA or FK506, facilitated or maintained Th2 cell generation, both with regards to CD4+ cell expansion and effector Th2 cytokine production.

Example 3

Evaluation of Immunosuppressive Agents on Th1 Responses

To evaluate the effect of these three agents, CSA, FK506, and rapamycin, on potential Th1-bias, the Th1 cultured cells were also re-stimulated with anti-CD3, anti-CD28, and the supernatant was tested for the type I cytokines IL-2 and IFN-γ. Murine CD4+ cells were expanded under the Th1 culture condition using anti-CD3, anti-CD28 co-stimulation. On day 6 of culture, T cells were harvested, washed, normalized to a concentration of $0.5 \times 10^6$ cells/ml, and re-stimulated with anti-CD3 and anti-CD28 (3:1 bead to T cell ratio) for 24 hours to generate a supernatant. Culture supernatants were tested for IL-2 and IFN-γ content by a two site ELISA (BioSource). Experimental samples scored relative to a standard curve generated from evaluation of recombinant murine IL-2 and IFN-γ. Cell culture labels along the x-axis represent cytokine and immune suppression agent conditions during the initial six days of T cell generation; there were no cytokines or immune suppression agents added during the time of 24 hour supernatant generation.

Figure 3:
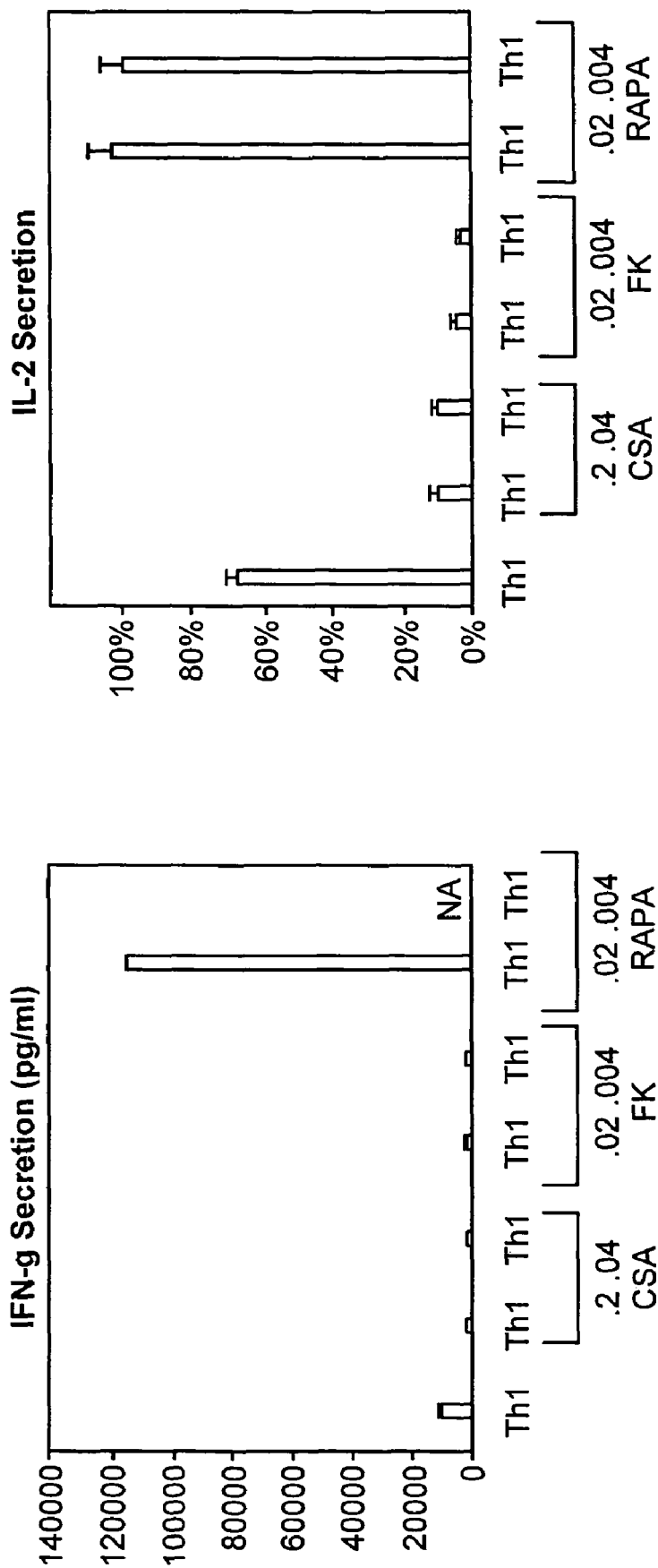
FIG. 3 is a graph showing that addition of CSA, and in particular, FK506, results in Th1 cells with significantly diminished capacity for both IL-2 and IFN-γ secretion.

As FIG. 3 shows, CSA, and in particular, FK506, resulted in Th1 cells with significantly diminished capacity for both IL-2 and IFN-γ secretion. In marked contrast, Th1 expansion in the presence of rapamycin resulted in a dramatic increase in Th1 cell capacity for IFN-γ secretion, and a nominal increase in IL-2 secretion capacity. As such, rapamycin, but not CSA or FK506, facilitated or maintained Th1 cell generation, both with regards to CD4+ expansion and effector Th1 cytokine production. In sum, these results also indicate that rapamycin, although it has been associated with a type II cytokine immune shift upon in vivo administration, does not appear to induce a Th1 to Th2 shift directly upon CD4+ cells. This observation implies that rapamycin induced type II promotion may operate indirectly, for example, through its actions on APC modulation.

Given these results that rapamycin unexpectedly preserved or enriched for Th1/Th2 polarity, a five-fold higher concentration of rapamycin, 0.1 µM, was evaluated. Murine CD4+ cells were co-stimulated with anti-CD3 and anti-CD28 coated magnetic beads under Th1 or Th2 conditions at previously tested rapamycin concentrations (0.008 µM to 0.02 µM), and a relatively high concentration (0.1 µM). Cell expansion was monitored over the six day culture by Multi-Sizer evaluation, and plotted on a log scale. FIG. 4 shows that even at this higher dose of rapamycin, the method of optimized co-stimulation and cytokine supplementation disclosed herein, allowed for the expansion of either Th1 or Th2 subsets without any apparent reduction in CD4 cell yield.

Example 4

Evaluation of Th1 and Th2 Responses Generated in Rapamycin

The Th1 or Th2 populations generated in the 0.1 µM rapamycin concentration were also evaluated. Murine CD4+ cells were expanded with anti-CD3, anti-CD28 coated magnetic beads under the Th1 or the Th2 culture conditions in the absence or presence of rapamycin (0.008 µM to 0.1 µM), as denoted on the x-axis of this figure. On day 6 of culture, the T cells were harvested, washed, and restimulated with fresh CD3, CD28 coated beads (3:1 bead to T cell ratio) in media not containing cytokines or immune suppression agent. A 24 hour culture supernatant was generated and tested for IL-2 and IFN-γ cytokine content by two site ELISA (BioSource) in reference to a standard curve.

Figure 5:
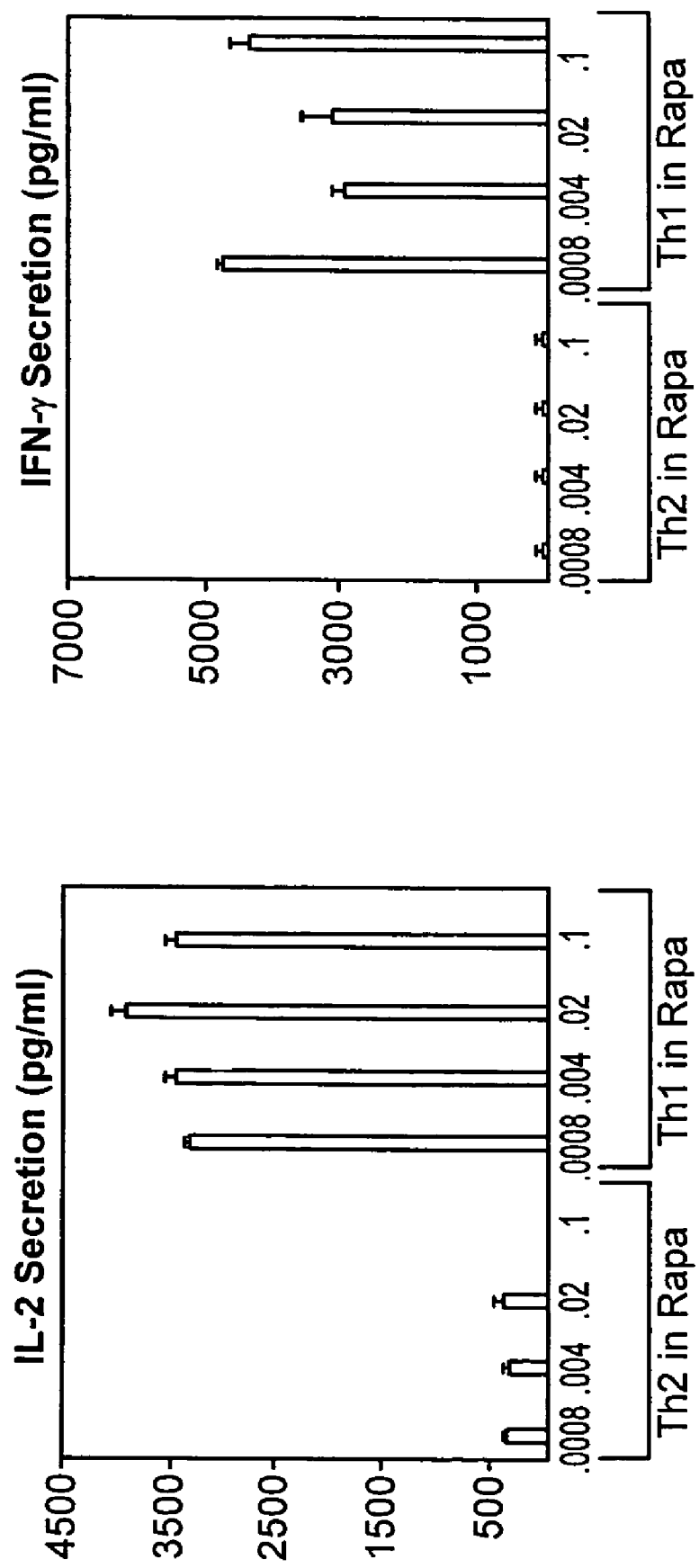
FIG. 5 is a graph showing that Th1 cells in each of the rapamycin concentrations had similarly high secretion of both IL-2 and IFN-γ.
Figure 6:
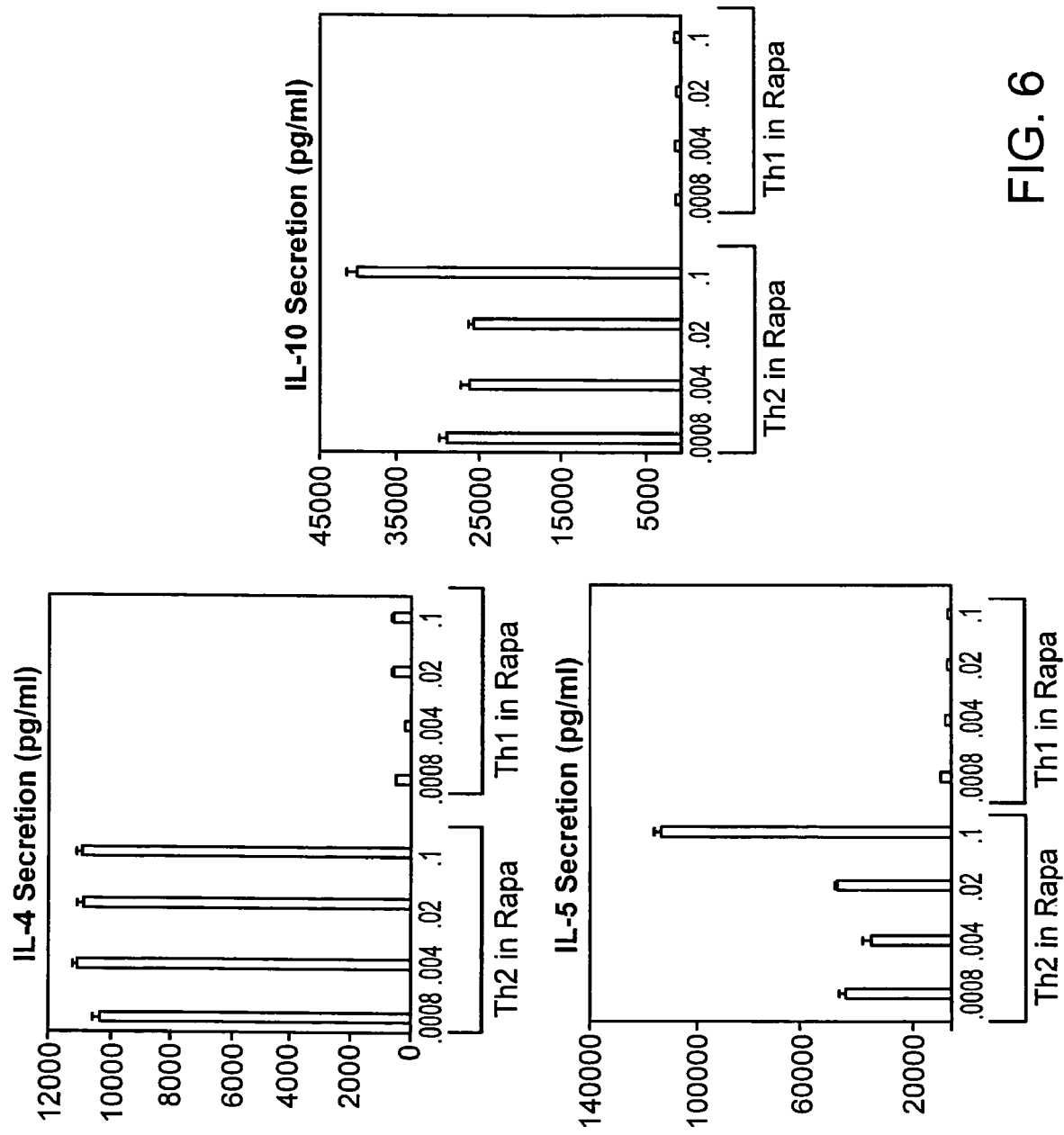
FIG. 6 is a graph showing that Th2 cells propagated in the 0.1 μM rapamycin concentration had preservation of capacity for secretion of the type II cytokines IL-4, IL-5, and IL-10.

As FIG. 5 shows, Th1 cells in each of the rapamycin concentrations had similarly high secretion of both IL-2 and IFN-γ. With respect to Th2 cell expansion in rapamycin, it was observed that expansion in the 0.1 µM rapamycin concentration was associated with elimination of the "contaminating" quantities of IL-2 secretion that were present in the lower dose rapamycin cultures and the control Th2 cultures. As such, the higher dose of rapamycin was associated with an improved Th2 phenotype, as defined by reduced IL-2 secretion. In contrast, FIG. 6 shows that Th2 cells propagated in the 0.1 µM rapamycin concentration had preservation of capacity for secretion of the type II cytokines IL-4, IL-5, and IL-10. Th1 cells propagated in 0.1 µM rapamycin did not have an increased capacity for type II cytokine secretion. These results thus further confirm that, in our system, Th1 or Th2 polarization can be maintained or even enhanced in the presence of relatively high rapamycin concentrations.

In FIG. 6, murine CD4+ cells were expanded with anti-CD3, anti-CD28 coated magnetic beads under the Th1 or the Th2 culture conditions in the absence or presence of rapamycin (0.008 µM to 0.1 µM), as denoted on the x-axis of this figure. On day 6 of culture, the T cells were harvested, washed, and restimulated with fresh CD3, CD28 coated beads (3:1 bead to T cell ratio) in media not containing cytokines or immune suppression agent. A 24 hour culture supernatant was generated and tested for type II cytokine content (IL-4, IL-5, and IL-10) by two site ELISA (BioSource) in reference to a standard curve.

Example 5

Cytokine Production after Rapamycin Exposure without Co-Stimulation

To determine whether CD28 signaling, perhaps through up-regulation of survival molecules such as bcl-2 family members or activation of the AKT pathway, might account for the observed capacity to overcome the expected rapamycin immune T cell suppression effect, the following experiments were conducted. The experiments were performed evaluating the polarizing cytokine conditions and rapamycin exposure after activation without co-stimulation through use of beads conjugated with only anti-CD3 antibodies. Murine CD4+ T cells were expanded with magnetic beads conjugated with only the T cell receptor activating antibody anti-CD3 or with beads conjugated with both anti-CD3 and anti-CD28 (denoted in figure by Th1 or Th2 condition). The condition receiving only anti-CD3 stimulation was performed either with or without the addition of rapamycin (0.02 µM concentration). Cell expansion was monitored over the six day culture by Multi-Sizer evaluation, and plotted on a log scale.

Figure 7:
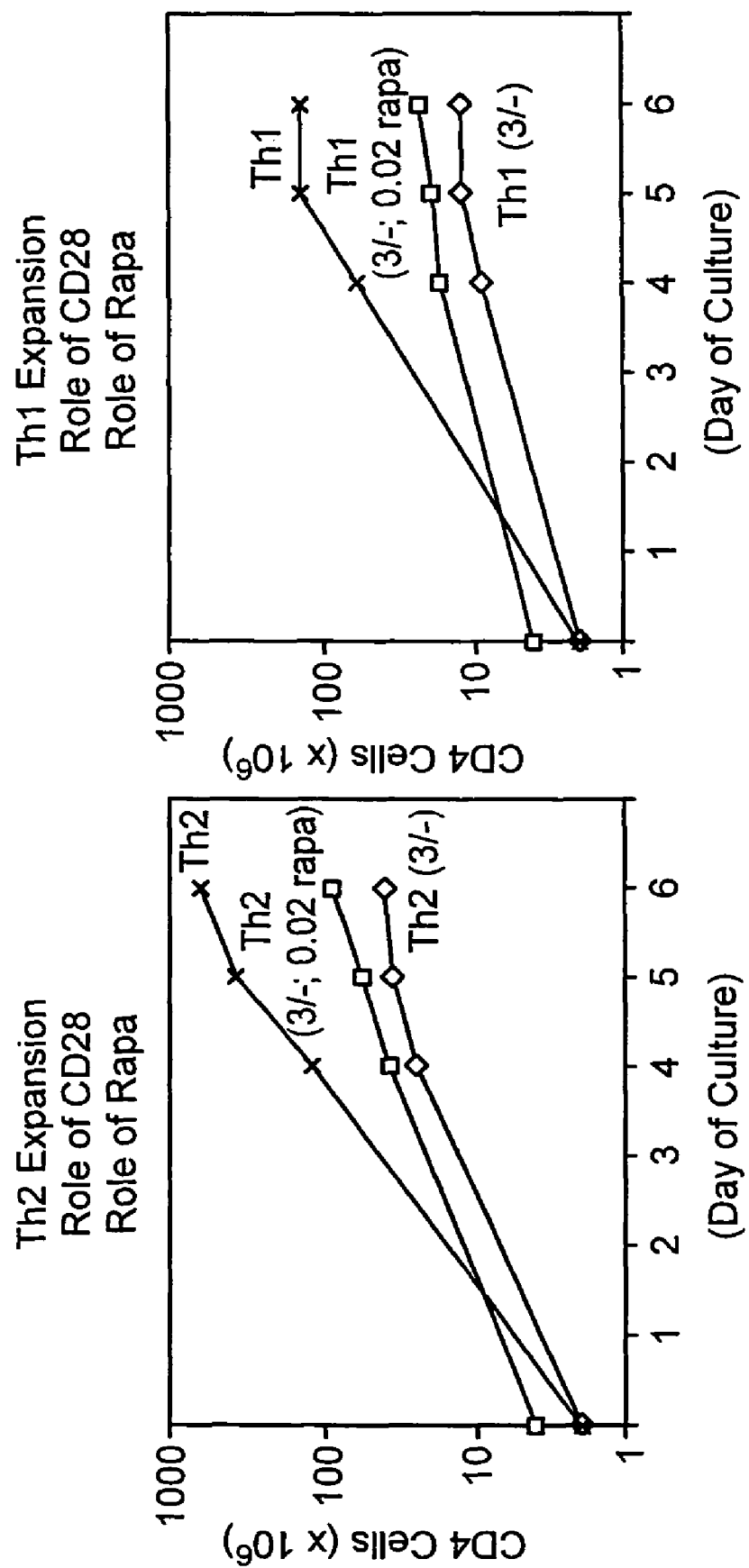
FIG. 7 is a graph showing Th2, and Th1 cell expansion was greatly reduced relative to CD3, CD28 co-stimulated control Th1/Th2 cultures.

As FIG. 7 shows, Th2, and in particular, Th1 cell expansion was greatly reduced relative to CD3, CD28 co-stimulated control Th1/Th2 cultures. However, addition of rapamycin to "signal 1 only" generated Th1 or Th2 cultures did not result in a significant decrease in CD4+ cell yield. This result suggests, at least at the 0.02 µM rapamycin concentration tested, that CD28 in this system may not provide a specific T cell activation or survival signal for the abrogation of the expected rapamycin T cell inhibition effects.

Example 6

Evaluation of Th1/Th2 Differentiation Generated in High Doses of Rapamycin

Higher dose levels of rapamycin during Th1/Th2 differentiation were evaluated. In the first panel of FIG. 8, murine CD4+ cells were expanded in the Th2 culture condition using anti-CD3 and anti-CD28 coated magnetic beads, with culture performed either in the absence or presence of rapamycin (0.1 µM to 10 µM). Cell expansion was monitored over the six day culture by Multi-Sizer evaluation, and plotted on a log scale.

Figure 8:
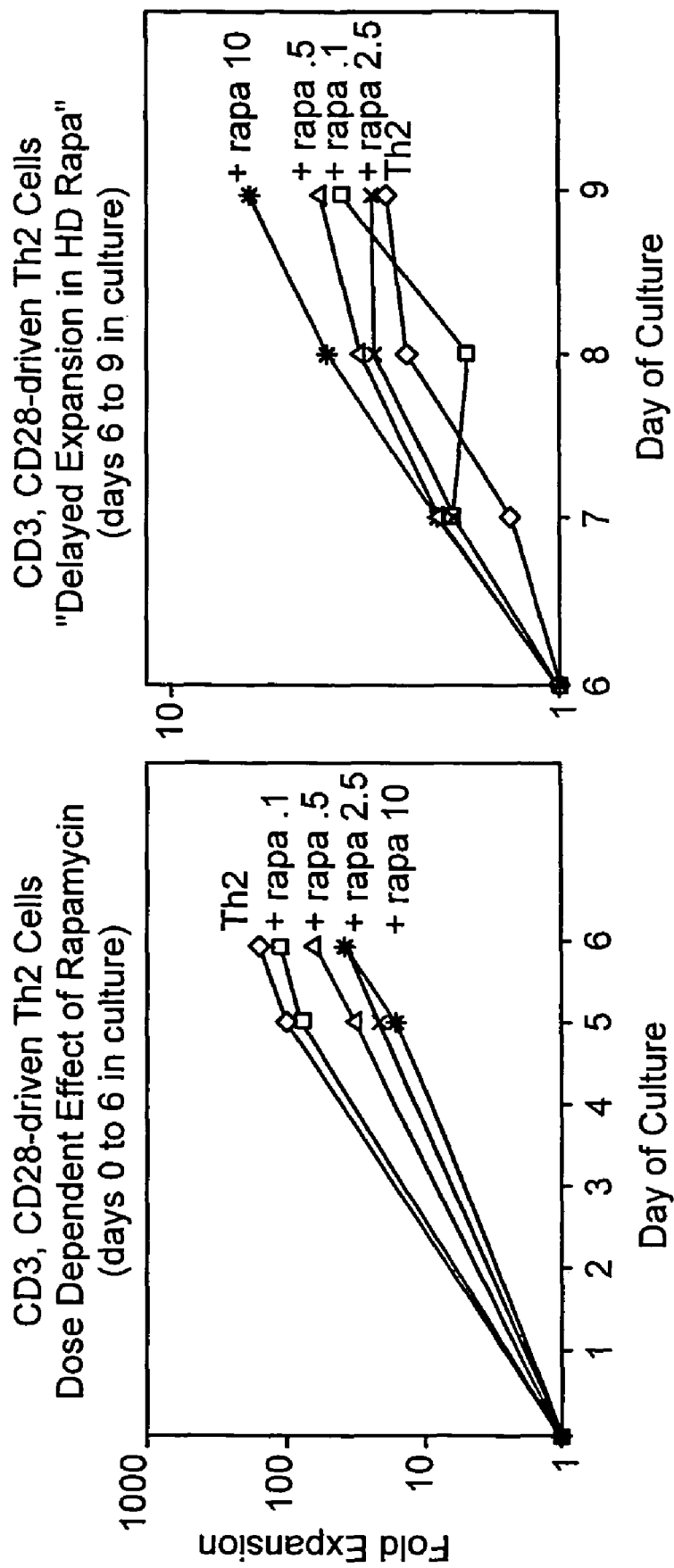
FIG. 8 is a graph showing CD3, CD28 generated Th2 cell expansion from day 0 to 6 of culture at rapamycin concentrations ranging from 0.1 μM to 10.0 μM.

In FIG. 8 (second-panel), CD4+ cells in each of the Th2 culture conditions were replated with normalization of T cell concentrations, and further expanded in media containing both the Th2 culture condition additives and rapamycin at the same concentrations as during culture initiation. Cell expansion was monitored from day 6 to day 9 of culture by Multi-Sizer evaluation, and plotted on a log scale.

Figure 9:
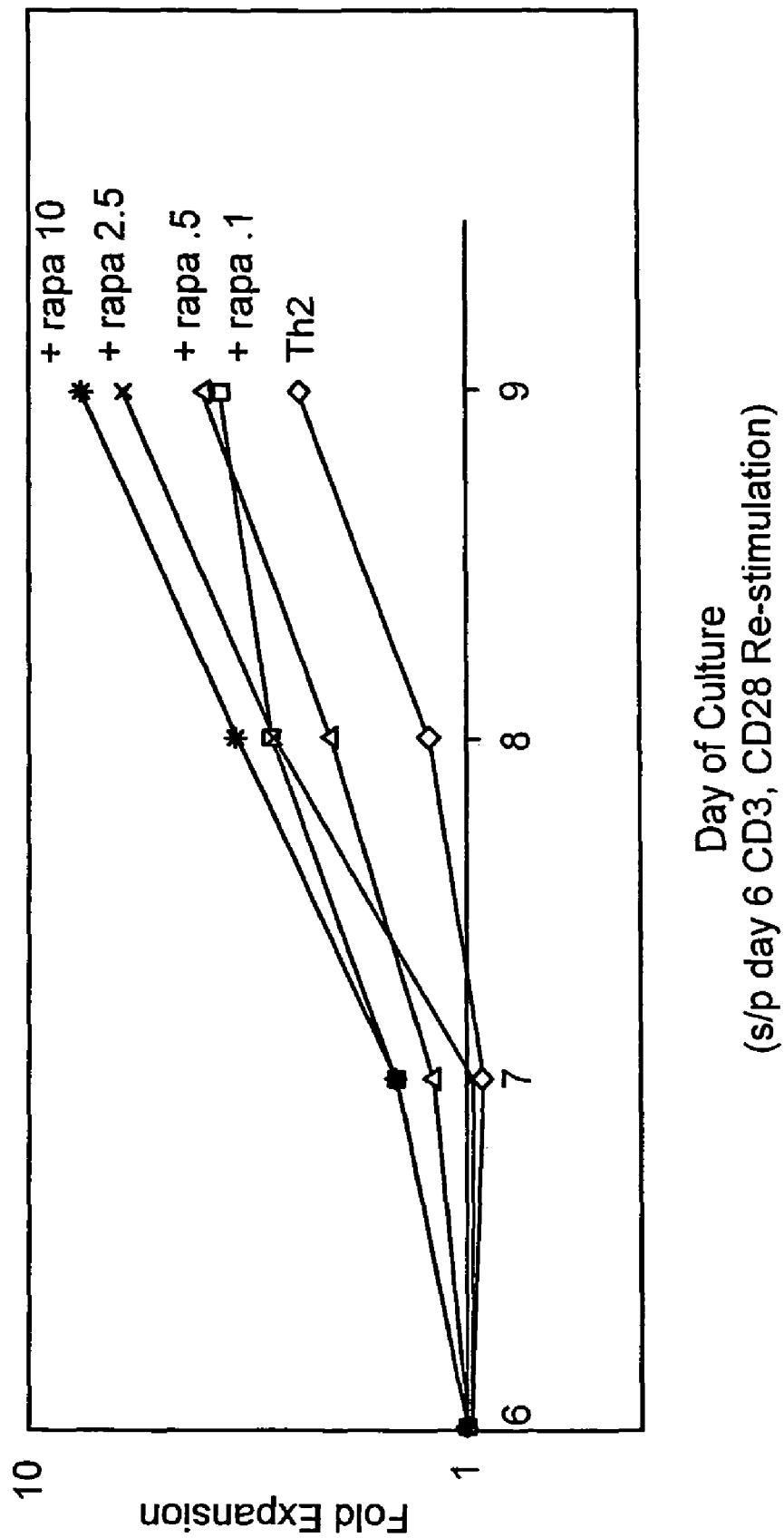
FIG. 9 is a graph showing the increase in numbers of CD4+ expressing cells in the high dose rapamycin cultures after day 6.

FIG. 8 shows CD3, CD28 co-stimulation, generated Th2 cell expansion from day 0 to 6 of culture at rapamycin concentrations ranging from 0.1 µM to 10.0 µM (left panel). As this figure shows, at both the 2.5 µM and 10 µM concentration, Th2 cell expansion was reduced approximately one log relative to the control culture. To evaluate whether this rapamycin-associated reduction in Th2 cell expansion was a progressive or transient process, cultures were each normalized for cell number on day 6 of culture, and propagated an additional three days in cytokine replete media (no further CD3, CD28 re-stimulation; FIG. 8, right panel). As this panel shows, the Th2 cultures initiated and continued in the higher concentration of rapamycin, had an increase in CD4+ cell expansion during day 6 to day 9 culture interval relative to the control Th2 culture. The increased CD4+ expansion in the high dose rapamycin cultures was also observed after day 6 anti-CD3 and anti-CD28 re-stimulation of cultures (with ongoing cytokine and rapamycin addition; result in FIG. 9).

Figure 10:
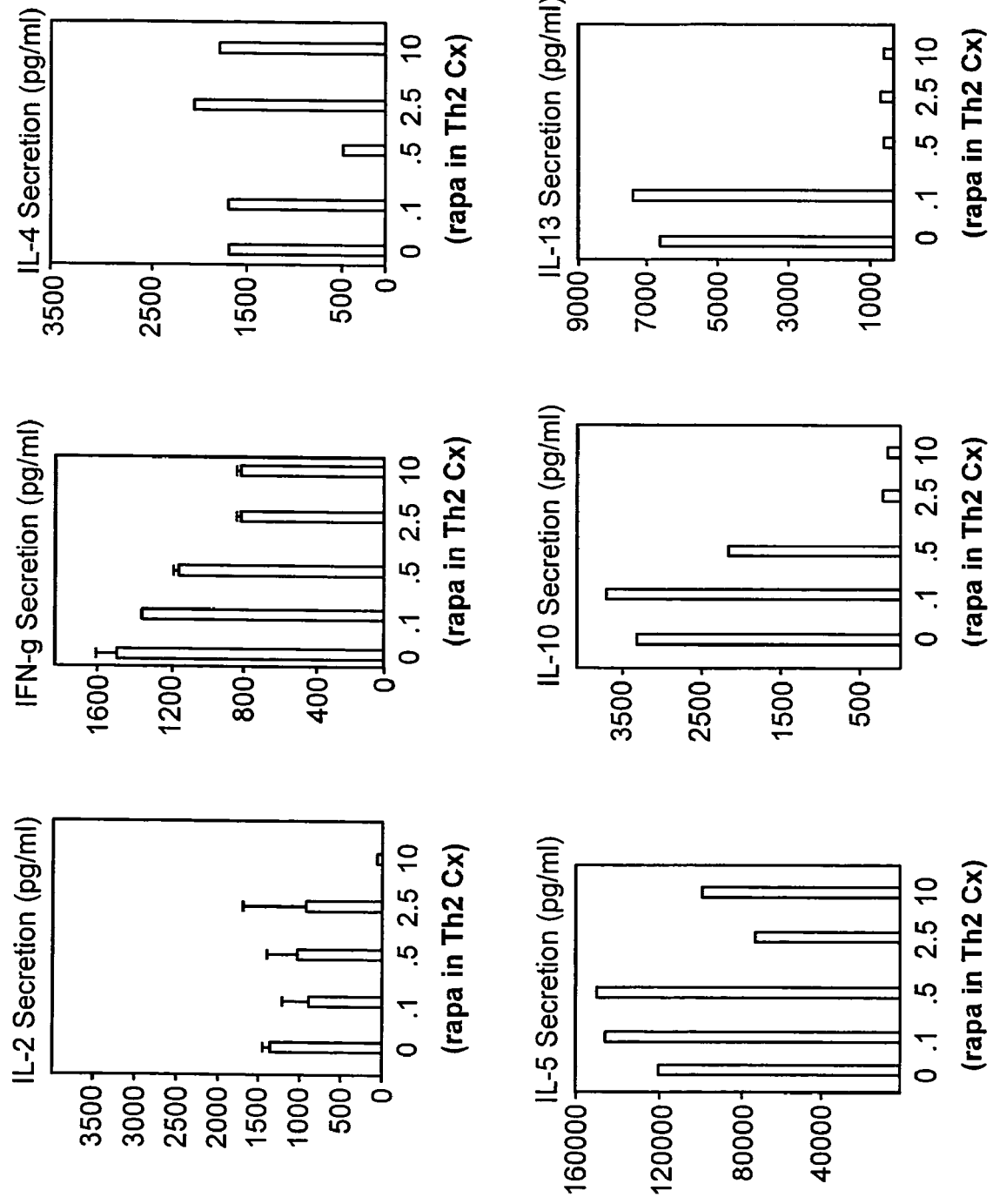
FIG. 10 is a graph showing that at the highest rapamycin concentration, the Th2 cells had an enhanced Th2 polarity on the basis of abrogation of contaminating IL-2 secretion and modest reduction in IFN-γ secretion.

These co-stimulated Th2 cultures generated in concentrations of rapamycin ranging from 0.1 to 10.0 µM were also evaluated for their Th1/Th2 cytokine secretion capacity (FIG. 10). As this figure shows, at the highest rapamycin concentration, the Th2 cells had an enhanced Th2 polarity on the basis of abrogation of contaminating IL-2 secretion and modest reduction in IFN-γ secretion. Such high-dose rapamycin generated Th2 cells had full preservation of the Th2-type cytokines associated with more proximal Th2 effector function, namely IL-4 and IL-5. In contrast, such cells had a significant reduction in the Th2-type cytokines associated with more distal Th2 effector function, IL-10 and IL-13. In sum, these results indicate that the high-dose rapamycin facilitated generation of a Th2 cell of enhanced purity (less Th1 contaminating elements) that was more proximal in its state of Th2 differentiation.

Figure 11:
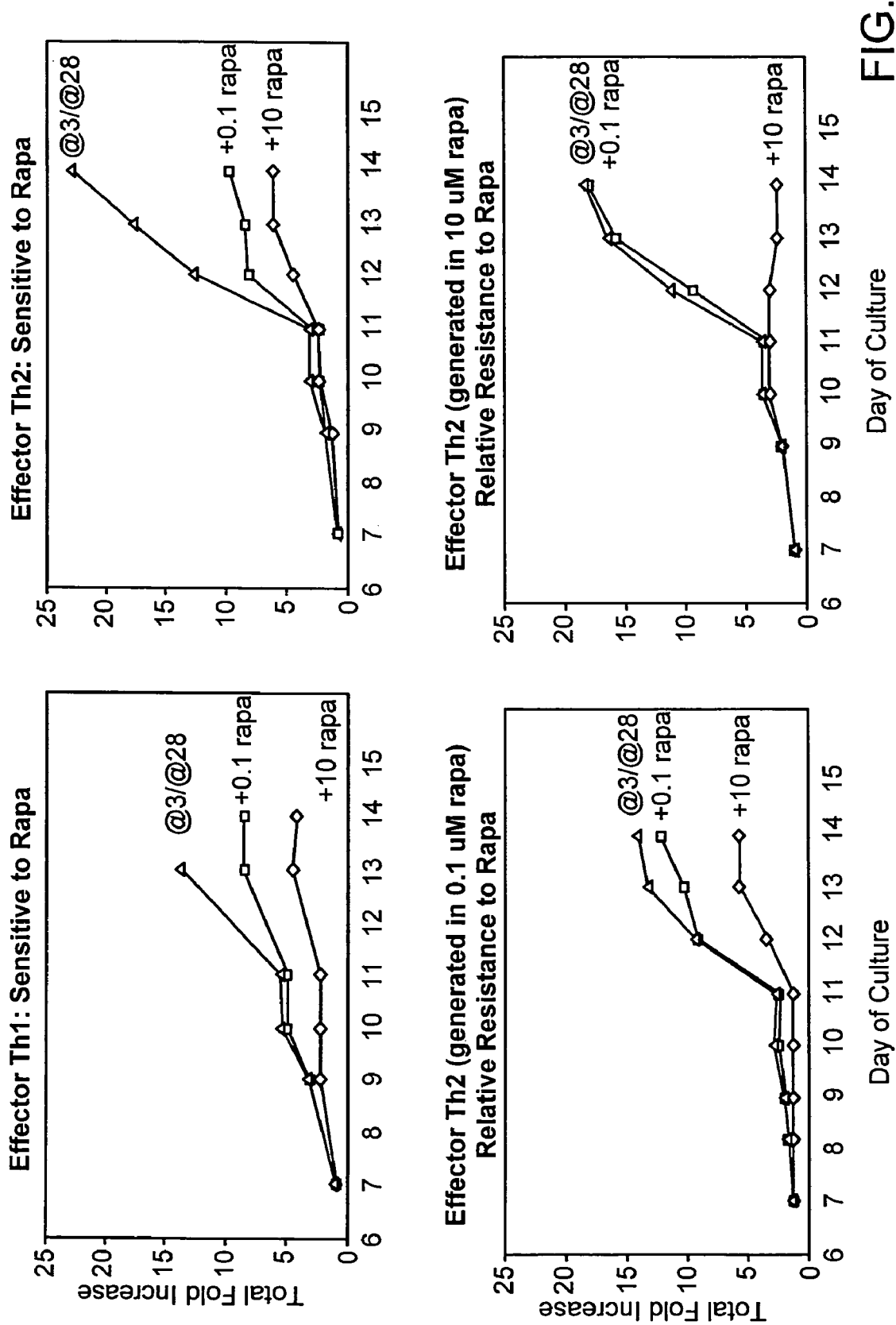
FIG. 11 is a graph showing Th1 or Th2 cells re-stimulated in the presence of 0.1 μM rapamycin, and 10 μM rapamycin.

To further evaluate the issue of rapamycin resistance in the murine Th1 or Th2 cultures, control effector Th1 or Th2 cells (day 6 of culture) or rapamycin-generated Th1 or Th2 effectors were re-stimulated with anti-CD3, anti-CD28 in the presence or absence of rapamycin (FIG. 11). As this figure shows, control Th1 or Th2 effectors re-stimulated in the presence of 0.1 µM rapamycin, and in particular, 10 µM rapamycin, had significantly reduced secondary expansion capacity. In contrast, Th2 cells generated in either 0.1 µM or 10 µM rapamycin had similar secondary expansion in either unsupplemented media or media supplemented with 0.1 µM rapamycin. This result indicates that, at the 0.1 µM rapamycin concentration, the rapamycin-generated Th2 cells are relatively resistant to the T cell inhibition compared to control Th2 effectors. However, secondary anti-CD3, anti-CD28 re-stimulation in the presence of 10 µM rapamycin resulted in significant inhibition of Th2 expansion even in the Th2 culture initially propagated in the 10 µM rapamycin concentration.

Figure 12:
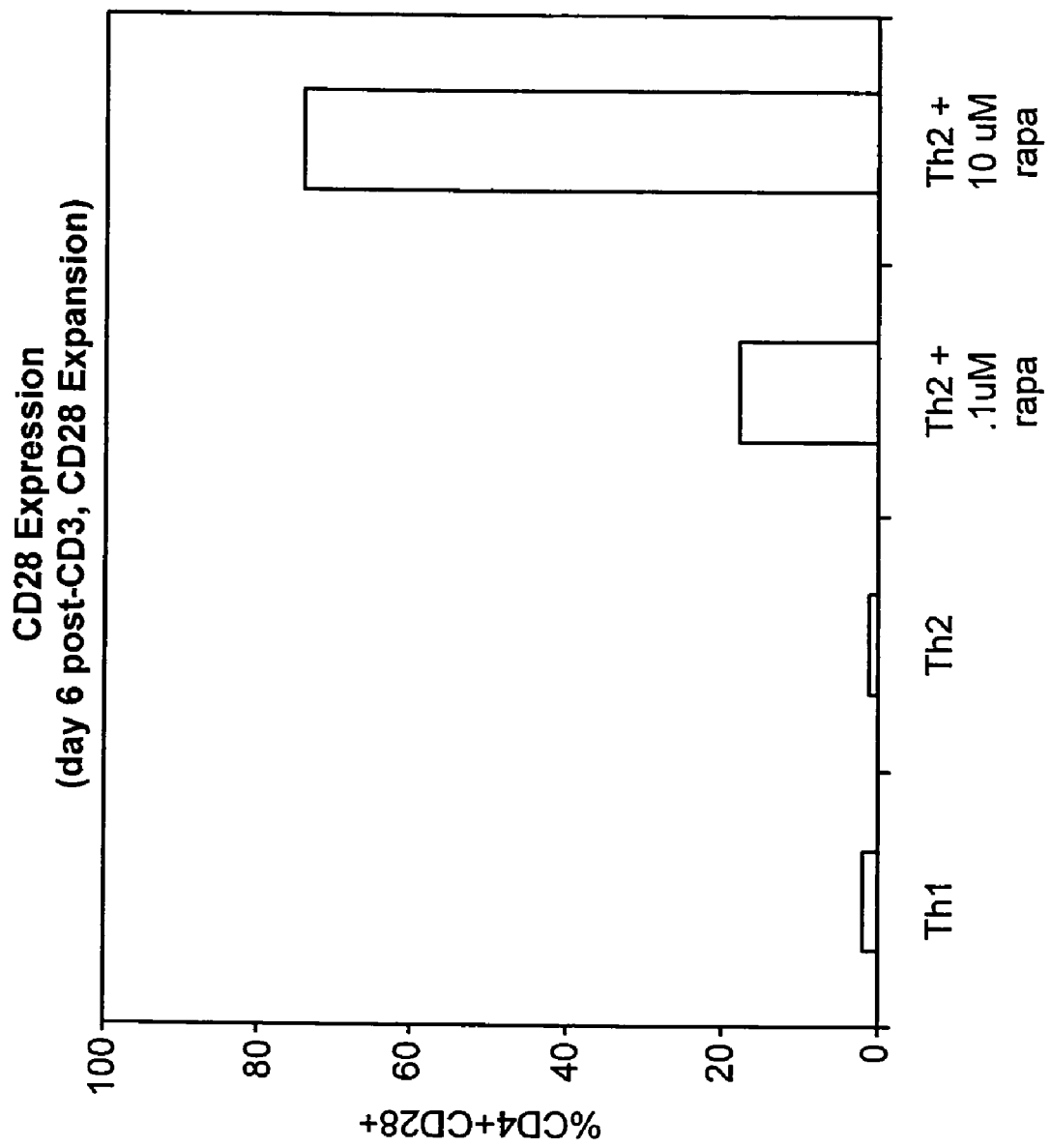
FIG. 12 is a graph showing that CD28 was greatly increased on the CD4+ cells that were propagated in high dose (10 μM) rapamycin.

In the high dose rapamycin generated Th2 cultures, the purity of cytokine polarity and the pattern of individual Th2 cytokine member secretion suggested that the CD4 cells emanating from such cultures possessed a more naïve phenotype. To address the possibility that high dose rapamycin might be selecting for a more naïve CD4 cell in culture, an evaluation of surface markers characteristic of naïve vs. memory function was conducted. One such functional marker is CD28 itself, which is present on nearly all naïve CD4+ cells, only to be reduced during the end stages of memory CD4+ effector differentiation. FIG. 12 demonstrates that CD28 indeed was greatly increased on the CD4+ cells propagated in high dose rapamycin. This result demonstrates that rapamycin, and in particular, the high dose rapamycin conditions, select for a more naïve CD4+ cell phenotype that expands during CD3, CD28 co-stimulation and thereby attains an increased purity of Th2 polarity.

Figure 13:
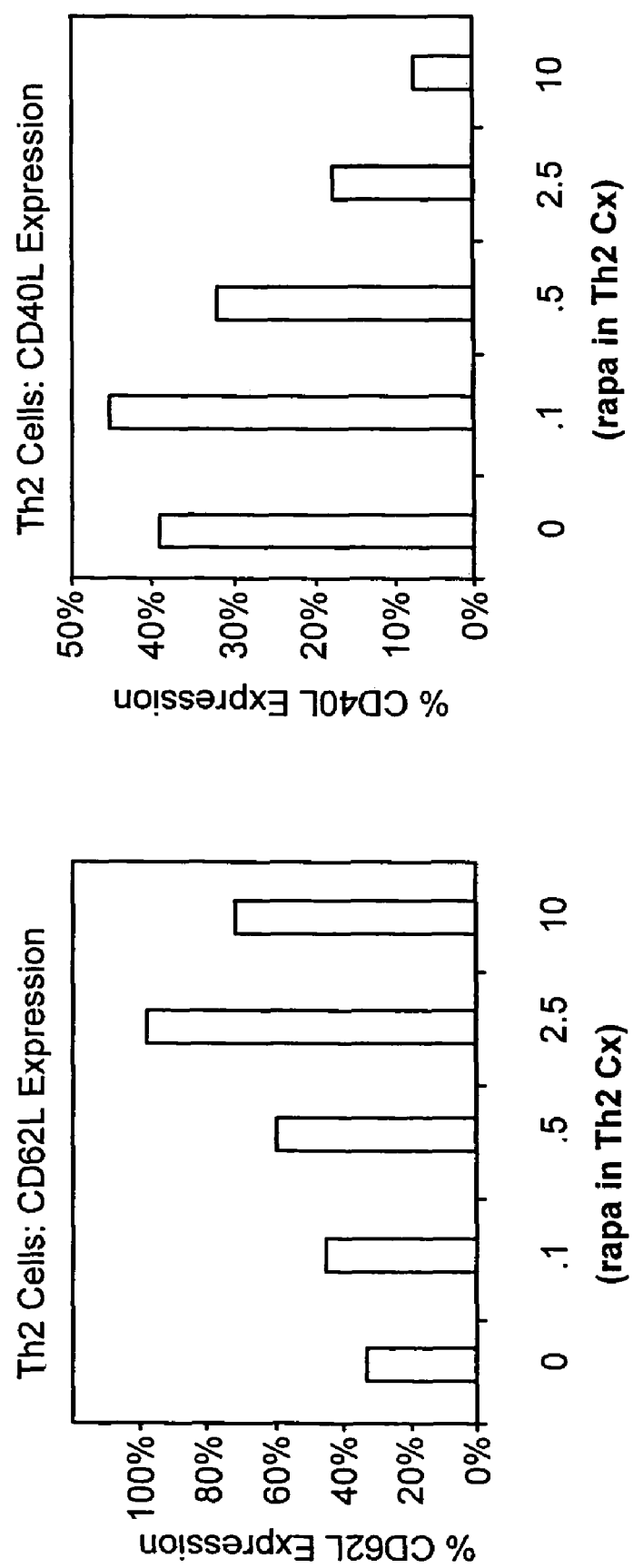
FIG. 13 is a graph showing that Th2 cells expanded in high dose rapamycin, had an increased expression of CD62L.

To further evaluate this, another cell surface molecule was measured. CD62L that functionally helps determine naïve vs. memory CD4 cell function. CD62, which is primarily expressed by more naïve CD4 cells, dictates T cell lymph node homing capacity rather than tissue-based effector function. As FIG. 13 shows, Th2 cells expanded in rapamycin, in particular, high dose rapamycin, had an increased expression of CD62L. Another cell surface molecule evaluated in these cultures was CD40L. CD40L is not so much a characteristic of naïve vs. memory status, but rather is a marker for Th1/Th2 polarity. That is, in our prior results, Th1-type cells have significantly increased CD40L relative to Th2-type cells. This association is of importance in light of the role of CD4 cell CD40L expression in up-regulation of IL-12 production in dendritic cell populations. A significant reduction in Th2 cell CD40L expression in the Th2 cultures propagated in rapamycin, in particular, high dose rapamycin was observed. In sum, Th2 generation in high-dose rapamycin provided a more pure Th2 profile, both on the basis of reduced contamination with IL-2 and IFN-γ secretion and reduced CD40L expression.

Example 7

CD8+ Tc1/Tc2 Modulation

Figure 14:
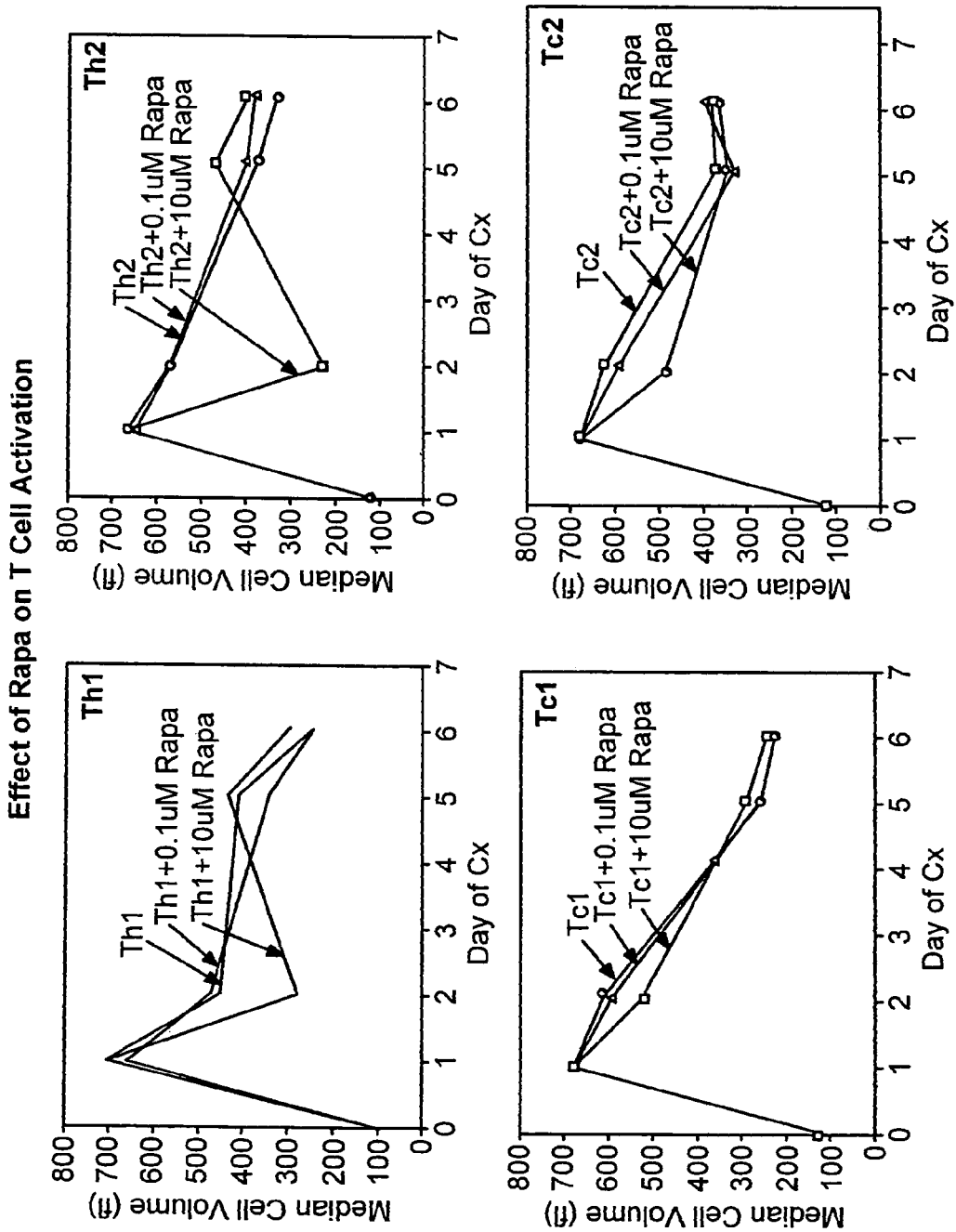
FIG. 14 is a graph showing shows median cell volume changes during Th1, Th2, Tc1, or Tc2 expansion in the presence or absence of either 0.1 or 0.0 μM rapamycin.

Both low- and high-dose rapamycin was evaluated on the generation of murine Tc1 and Tc2 populations after CD3, CD28 co-stimulatory conditions. As a first step in this direction, T cell activation patterns of murine CD4+ and CD8+ T cells under Th1/Th2 or Tc1/Tc2 differentiation conditions were evaluated. In prior studies, we have demonstrated that median cell volume, as measured by Coulter counting, is a surrogate marker for T cell activation as it correlates with other events such as CD25 and CD69 up-regulation. FIG. 14 shows median cell volume changes during Th1, Th2, Tc1, or Tc2 expansion in the presence or absence of either 0.1 or 10.0 µM rapamycin. Without rapamycin, each T cell subset has a dramatic increase in median cell volume after CD3, CD28 co-stimulation. With rapamycin addition, even at the 10 µM condition, maximal median cell volume in each T cell subset was not reduced relative to the control T cells. However, in the CD4+ Th1 and Th2 cultures, there was a more rapid return of median cell volumes towards the basal levels in high dose rapamycin. In contrast, there was not such a dramatic rapamycin-associated reduction in median cell volume in the CD8+ Tc1 or Tc2 conditions. This result suggests that CD4+ T cells may be more amenable to modulation by high-dose rapamycin than CD8+ T cells.

Figure 15:
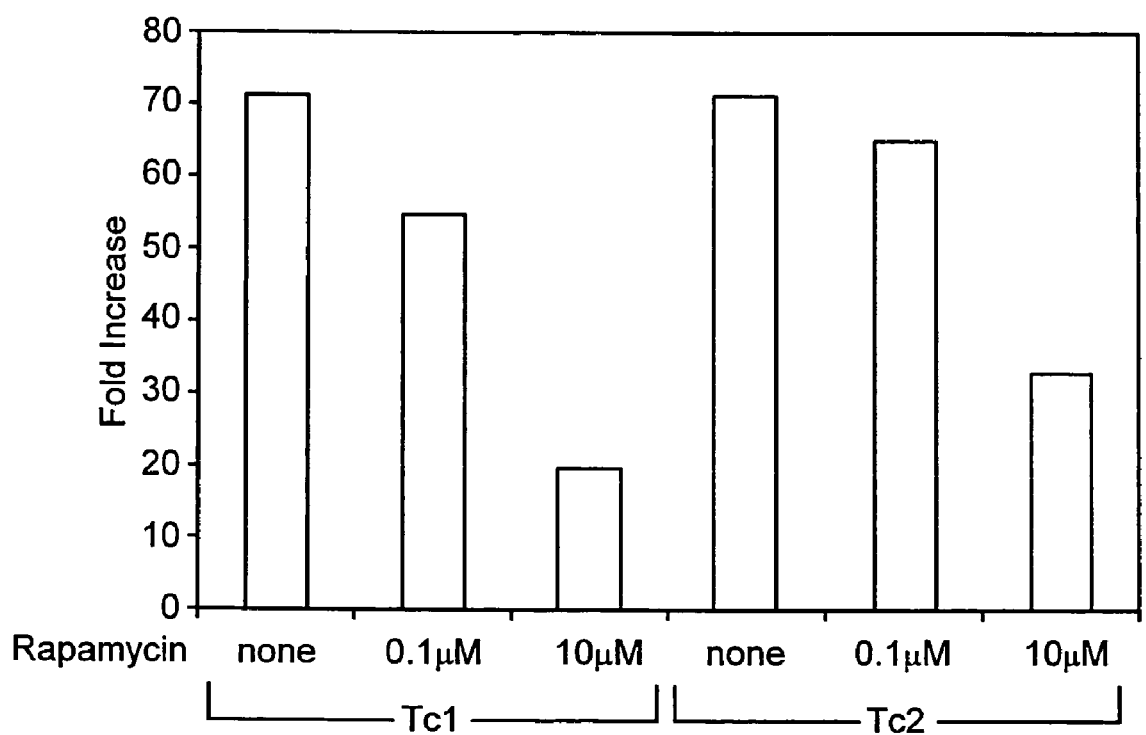
FIG. 15 is a graph showing $CD8^+$ Tc1/Tc2 expansion after CD3, CD28 co-stimulation in the presence of 0.1 μM and 10 μM of rapamycin.

Similar to results with CD4+ Th1/Th2 generation, CD8+ Tc1/Tc2 expansion after CD3, CD28 costimulation was nominally reduced at the 0.1 µM rapamycin concentration, with more significant reductions occurring at 10 µM of rapamycin (FIG. 15).

Example 8

Effects of Rapamycin on Cytotoxic T Cells

To evaluate whether rapamycin exposure influenced CD8+ cytotoxic effector function, chromium release assays were performed (FIG. 16 shows CTL assays using Tc2 effectors generated in the presence or absence of rapamycin). As this figure shows, the Tc2 cells propagated in high dose rapamycin had reduced lytic capacity through the fas pathway, as evidenced by their reduced capacity to lyse L1210-fas transfected tumor targets under conditions of calcium neutralization (left panel). Similarly, Tc2 cells propagated in high dose rapamycin had a reduced capacity to lyse the P815 tumor target in a heteroconjugate assay in calcium-replete conditions, an assay that reflects granule-mediated killing function. In sum, Tc2 cells generated in high dose rapamycin had reduced granule and fasL killing function relative to Tc2 cells propagated in low-dose or no rapamycin.

Figure 18:
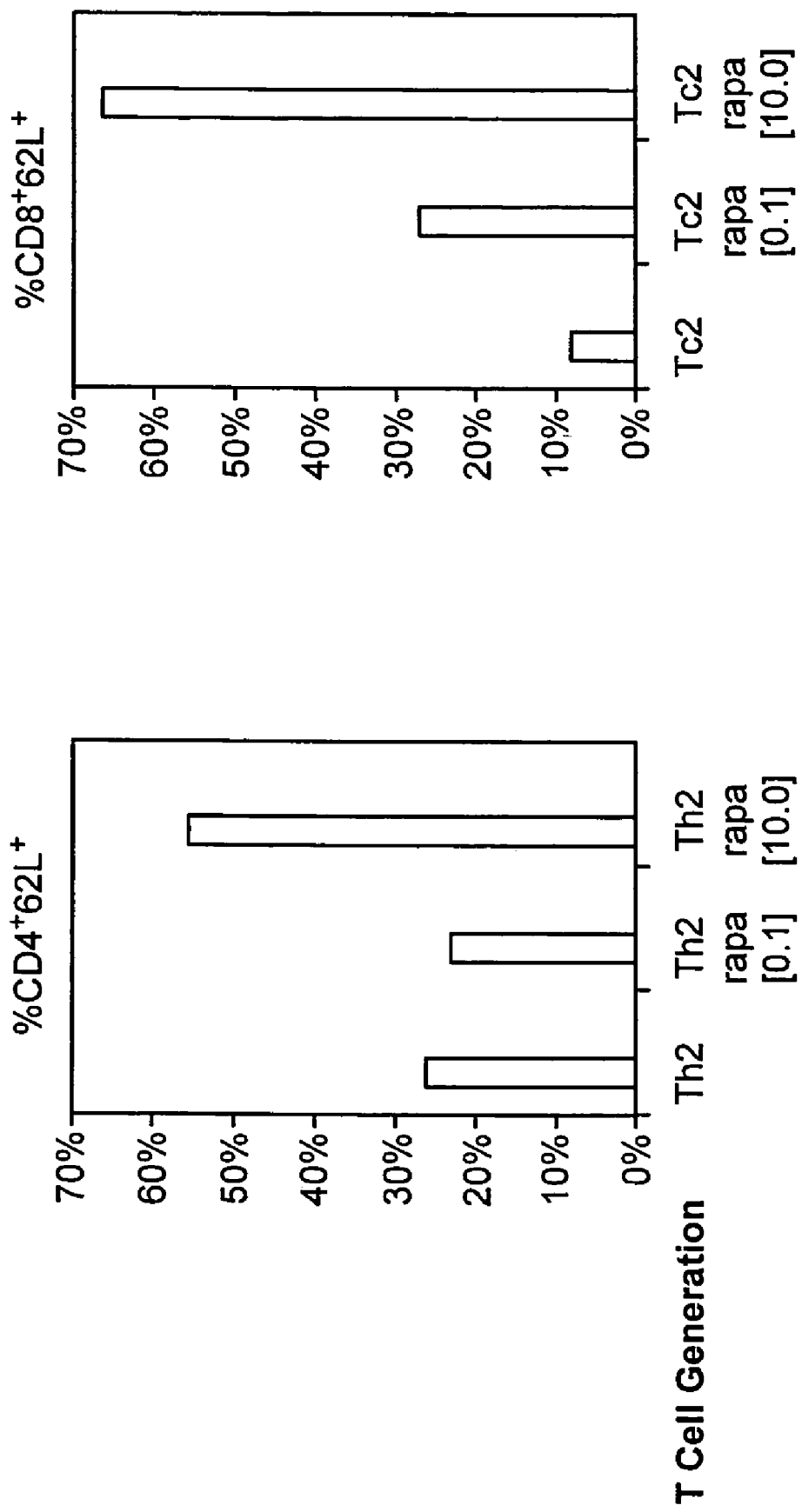
FIG. 18 is a graph showing that $CD8^+$ cell expansion in high-dose rapamycin was associated with a more naïve T cell phenotype, as evidenced by increased CD62L expression.

In contrast to Th1/Th2 differentiation in high dose rapamycin, where either phenotype could be attained without evidence for Th1/Th2 bias, the results indicate that CD8 expansion in rapamycin may favor a type II cytokine bias. That is, as FIG. 17 shows, Tc1 cells expanded in the high dose of rapamycin lost their capacity for IFN-γ secretion and had reduced capacity for IL-2 secretion. Similarly, Tc2 cells expanded in high dose rapamycin lost their capacity for IFN-γ secretion. In marked contrast, Tc2 cell secretion of the type II cytokines IL-4, IL-5, and IL-10 was not reduced by the high dose rapamycin condition. As such, similar to the Th2 cell culture in high dose rapamycin, the purity of Tc2 cells can be increased (on the basis of reduction in contaminating type I cytokine secretion) by high dose rapamycin exposure. It is interesting to note that loss of IFN-γ secretion in the rapamycin-generated Tc1 culture was not associated with induction of Tc1 cell type II cytokine secretion, and therefore does not indicate a simple rapamycin-associated T1 to T2 shift in polarity. Similar to the case with CD4+ Th2 cells, CD8 expansion in high-dose rapamycin was associated with a more naïve T cell phenotype, as evidenced by increased CD62L expression (FIG. 18).

Example 9

Evaluation of Rapamycin In Vitro and In Vivo: GVHD and GVT

In prior studies, allogeneic donor Th2 cells were associated with reduced GVHD, and could modulate GVHD induced by unmanipulated donor CD4+ and CD8+ T cells. In light of the results shown herein, that rapamycin enhanced Th2 purity of costimulated donor Th2 cells, it is likely that rapamycin-generated Th2 cells may have enhanced in vivo capacity to modulate GVHD. Furthermore, since the rapamycin-generated cells maintained resistance to rapamycin inhibition relative to unmanipulated T cells it was hypothesized that in vivo rapamycin may allow selective expansion of the Th2 cells relative to other, unmanipulated donor T cells.

Figure 19:
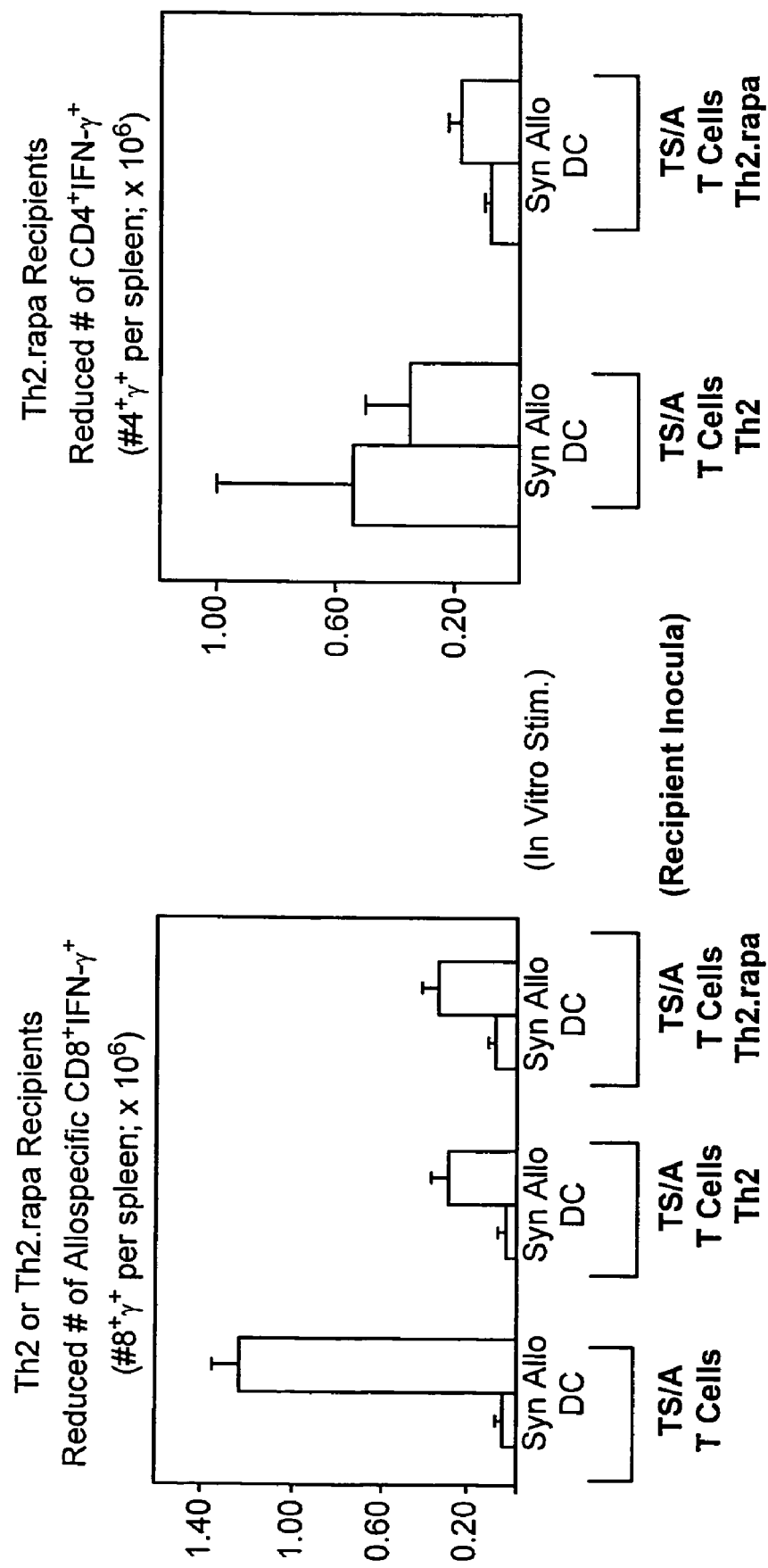
FIG. 19 is a graph showing that recipients of allogeneic splenic T cell inocula had a significant number of alloreactive $CD8^+$ T cells capable of IFN-γ secretion at day 7 post-BMT.

In a murine model of fully MHC-mismatched transplantation, the in vivo effect of co-stimulated control Th2 cells relative to rapamycin-generated Th2 cells was evaluated. This model involves transfer of C57Bl/6 (B6) bone marrow and splenic CD4+ and CD8+ T cells into lethally irradiated F1 hosts (C57Bl/6×Balb/c). After parental transplantation with this GVHD-inducing inocula, recipient mice were further injected i.v. with host-type breast cancer cells, the TS/A cell line (spontaneously arising tumor of balb/c origin). On day 7 after BMT, n=5 mice were killed per treatment group, splenic T cells were isolated, re-stimulated with either syngeneic B6 or allogeneic F1 dendritic cells in vitro, and cytokine secretion (IFN-γ) from splenic CD8+ T cells was evaluated by Miltenyi cytokine capture assay. The absolute number of splenic CD8+, IFN-γ+ donor T cells was then calculated per spleen, with this result being a biologic endpoint for acute GVHD biology. As FIG. 19 shows (left panel), recipients of the allogeneic splenic T cell inocula had a significant number of alloreactive CD8+ T cells capable of IFN-γ secretion at day 7 post-BMT. Other treatment groups received the same splenic T cell inoculate and additional donor Th2 cells that were either co-stimulated in the presence or absence of rapamycin (in this experiment, 0.1 µM rapamycin). As FIG. 19 shows, recipients of additional donor Th2 cells had reduced in vivo generation of allospecific CD8+ IFN-γ cells, indicating Th2 down-modulation of GVHD. The level of reduction in CD8+ IFN-γ secretion was comparable in recipients of Th2 or rapamycin-generated Th2 populations. In addition, Th2 recipients were also evaluated for IFN-γ secretion from the expanded Th2 cells 7 days after in vivo transfer in the GVHD/GVT model (Th2 cells were identified by flow cytometry on the basis of their expression of the congenic marker, Ly5.1). As FIG. 19 shows (right panel), Th2 cells propagated in rapamycin had a reduced capacity for IFN-γ secretion after in vivo transfer relative to conventional co-stimulated Th2 cells. This reduced Th2 cell IFN-γ secretion in rapamycin-generated Th2 recipients was observed with syngeneic DC re-stimulation, which likely reflects true in vivo activation in the GVHD model, and with potential for IFN-γ secretion upon allogeneic DC stimulation. These data thus indicate that rapamycin-generated Th2 cells maintained a more pure Th2 function in vivo in the GVHD model as determined by reduced IFN-γ secretion.

Figure 20:
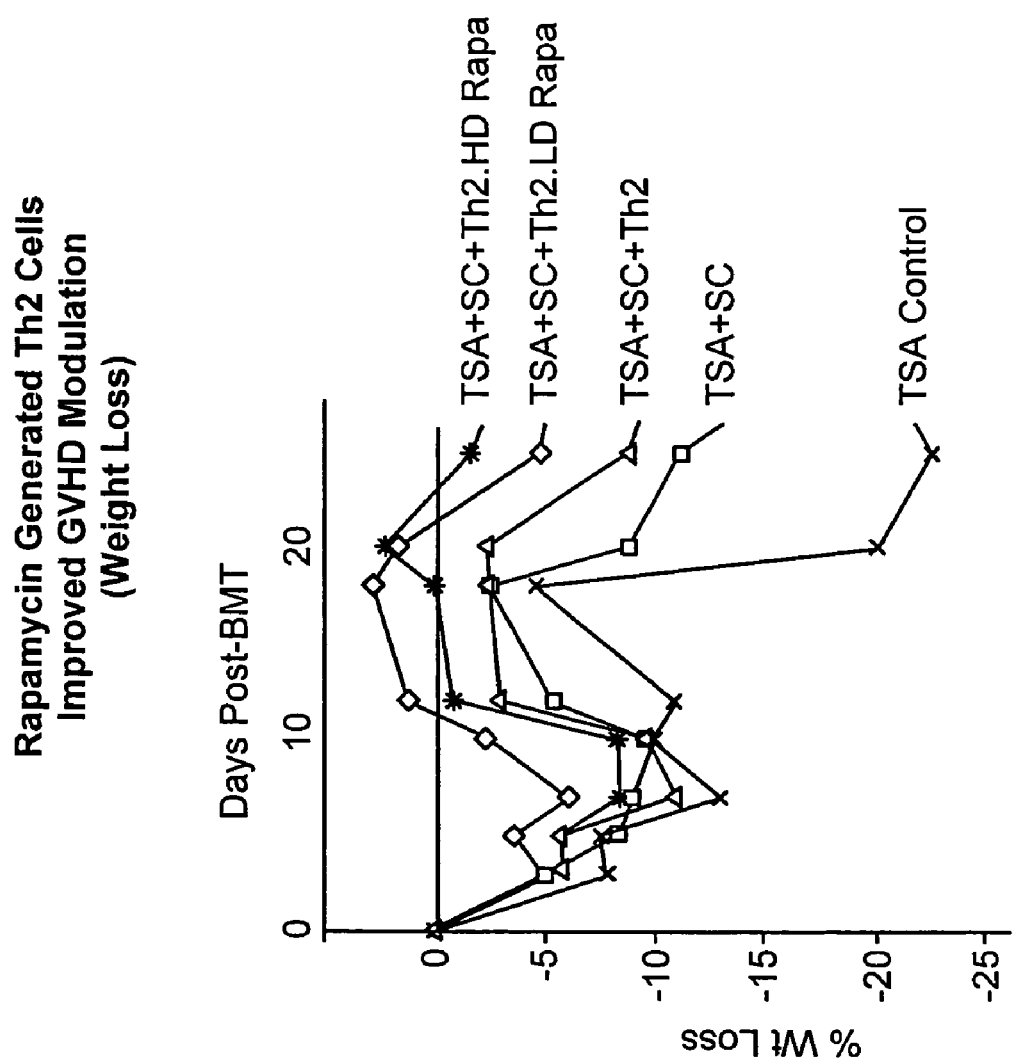
FIG. 20 is a graph showing that recipients of splenic $CD4^+$ and $CD8^+$ T cells underwent weight loss consistent with acute GVHD.

In a separate experiment, conventional Th2 cells or Th2 cells expanded in low dose (0.1 µM) or high dose (10 µM) rapamycin were evaluated in the same GVHD/GVT model, with weight loss, histology, and survival as experimental endpoints. As FIG. 20 shows, recipients of splenic CD4+ and CD8+ T cells underwent weight loss consistent with acute GVHD. Also shown in this figure is the TS/A control group that received tumor and no donor splenic T cells; weight loss in this group is thus attributed to tumor (pulmonary metastasis): Supplementation of splenic T cell inoculate with conventional co-stimulated Th2 cells resulted in a modest amelioration of acute GVHD-related weight loss. Importantly, recipients of Th2 cells generated under either low dose or high dose rapamycin had a more dramatic reduction in GVHD-related weight loss. This result indicates that rapamycin-generated Th2 cells were more effective at GVHD modulation.

Figure 21:
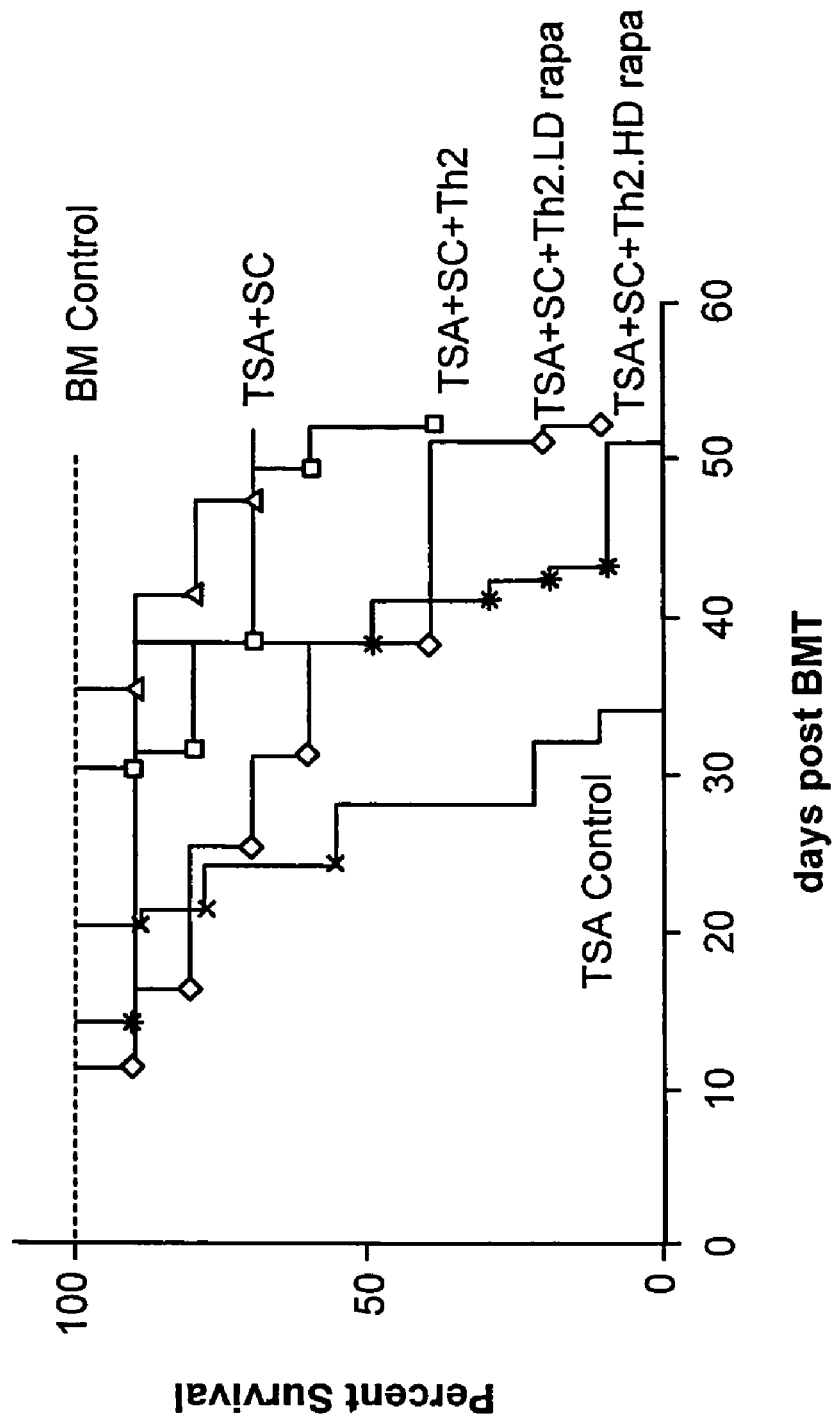
FIG. 21 is a graph showing survival results in recipients of Th2 cells generated under either low dose or high dose rapamycin.

FIG. 21 shows survival results from this experiment, with n=10 mice in each group evaluated for survival. As this figure shows, each recipient of carcinoma cells and no donor T cells (TS/A control) died of tumor within one month post-BMT. In this experiment, which was carried out at a modest irradiation dose of 1050 cGy, the GVHD control group receiving splenic T cells did not undergo lethality in spite of the dramatic pattern of progressive GVHD-induced weight loss. In this treatment cohort, there was a significant GVT effect based on increased survival, with deaths in this group attributed to GVHD. Recipients of additional Th2 cells, and in particular, Th2 cells expanded in rapamycin, had preservation of a component of the GVT effect. The potency of this GVT effect, however, was reduced relative to the GVHD control, as deaths occurring in these treatment cohorts were attributable to tumor relapse. As such, these data indicate that co-stimulated Th2 cells reduce GVHD (rapamycin-generated Th2>conventional Th2) and that Th2 modulation of GVHD reduced but did not abrogate the potency of the GVT effect. Further experiments evaluating these treatment cohorts are being conducted at higher radiation doses. GVHD-related lethality is generated in the control groups and a survival advantage in recipients of the rapamycin-generated Th2 cells is shown.

Example 10

Preferential Expansion of Rapamycin Resistant T Cells In Vivo

Figure 22:
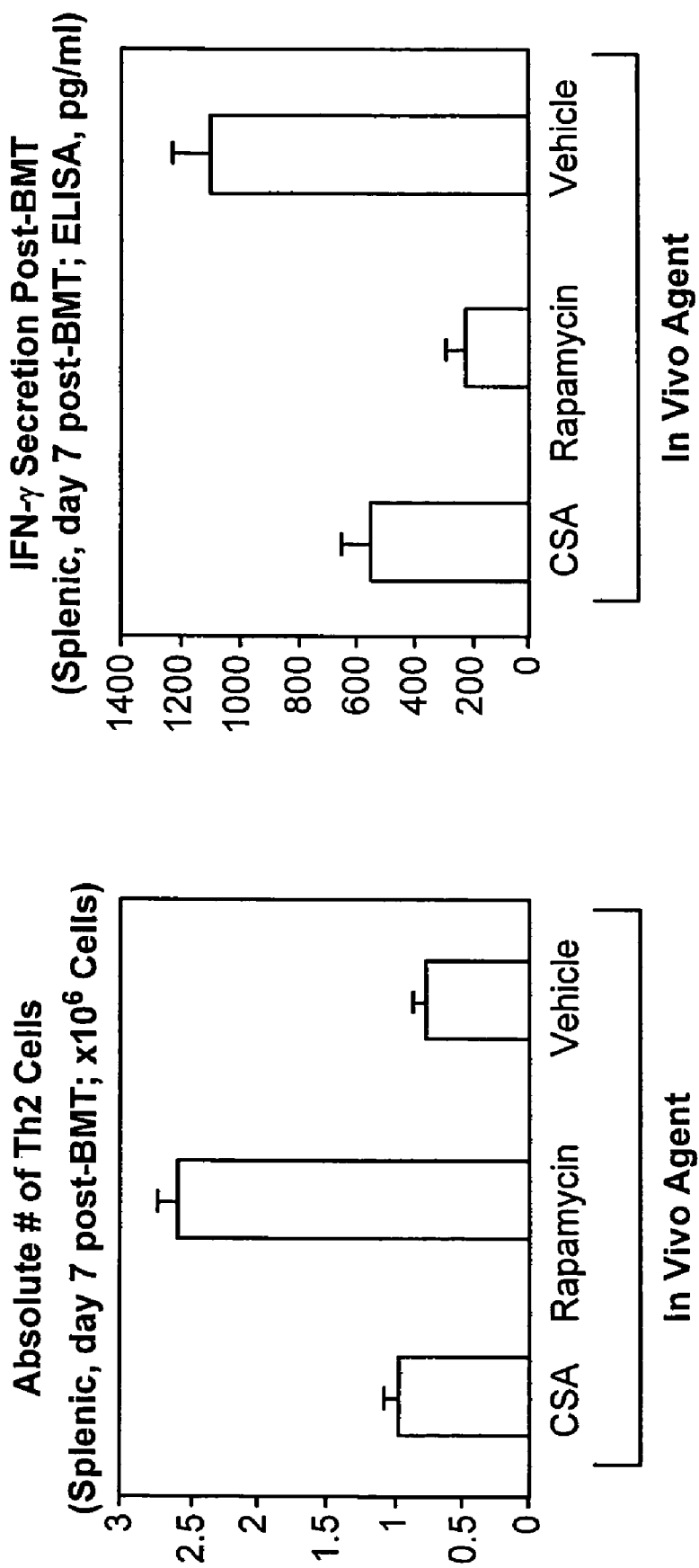
FIG. 22 is a graph showing that administration of rapamycin-generated Th2 cells and in vivo rapamycin resulted in a greater number of Th2 cells in the day+7 spleens than cell administration and CSA or vehicle administration.

As a further strategy for Th2 modulation of acute GVHD, it was evaluated whether rapamycin-generated Th2 cells might be preferentially expanded by in vivo rapamycin administration. To this extent, the GVHD/GVT model was utilized, with splenic T cell inoculate supplemented with rapamycin-generated donor Th2 cells (0.1 µM concentration). In addition, recipient mice were injected daily with either rapamycin, cyclosporin A, or CMC vehicle from day 0 to day+7 post-BMT. As FIG. 22 shows (left panel), administration of rapamycin-generated Th2 cells and in vivo rapamycin resulted in a greater number of Th2 cells in the day+7 spleens than cell administration and CSA or vehicle administration. Importantly, as FIG. 22 (right panel) indicates, this enhanced Th2 cell expansion in vivo was associated with a net reduction in the capacity of post-BMT splenic T cells to secrete IFN-γ. In sum, these results indicate that rapamycin generated Th2 cells, which have a more pure Th2 phenotype and a more naïve phenotype, have a greater capacity for GVHD modulation; this Th2 modulation can be further optimized by in vivo rapamycin administration.

Example 11

Evaluation of Rapamycin in Human CD4+ Cells

Figure 24:
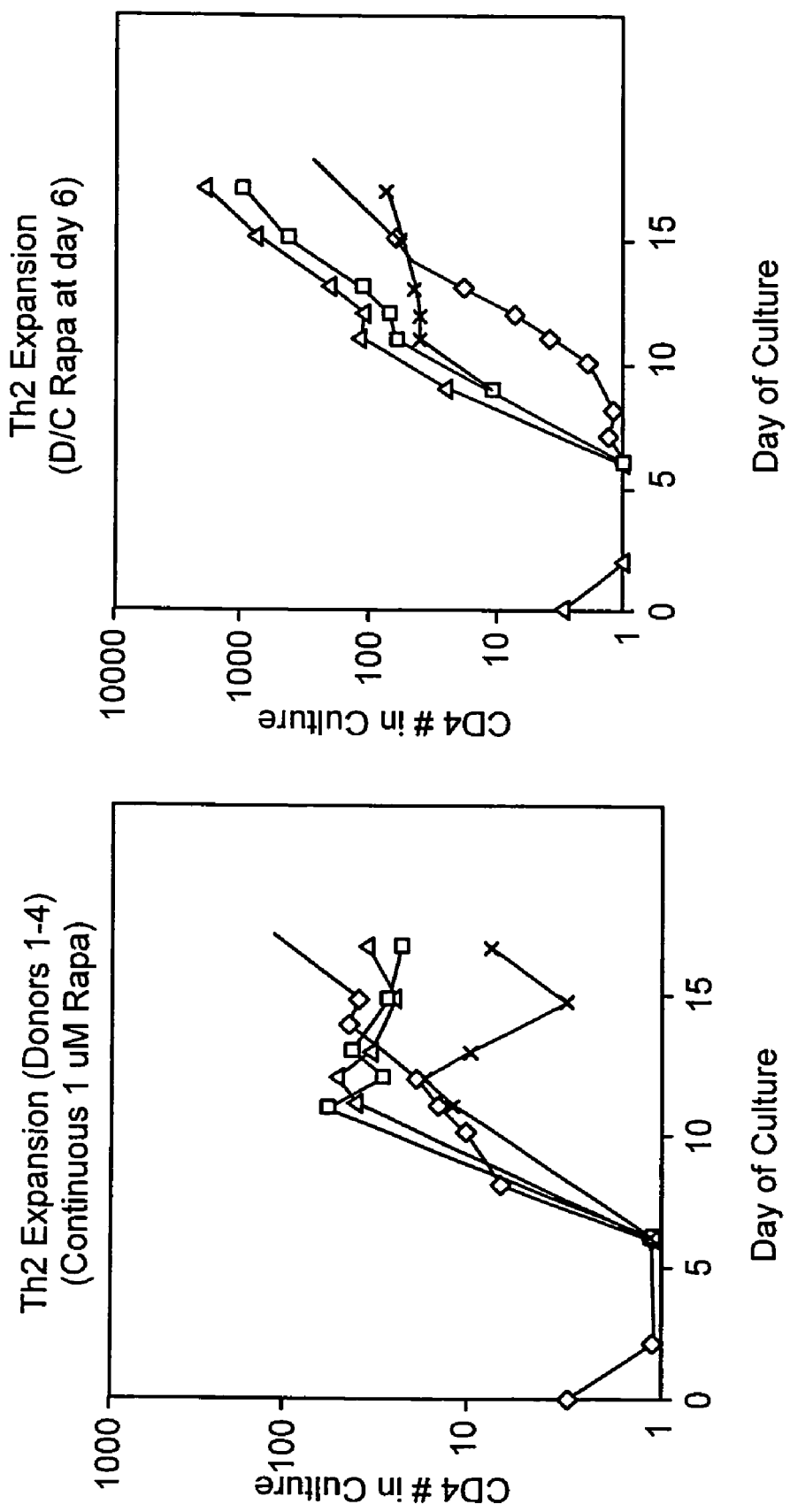
FIG. 24 is a graph showing the growth curves of CD4+ cell in the presence of rapamycin.
Figure 25:
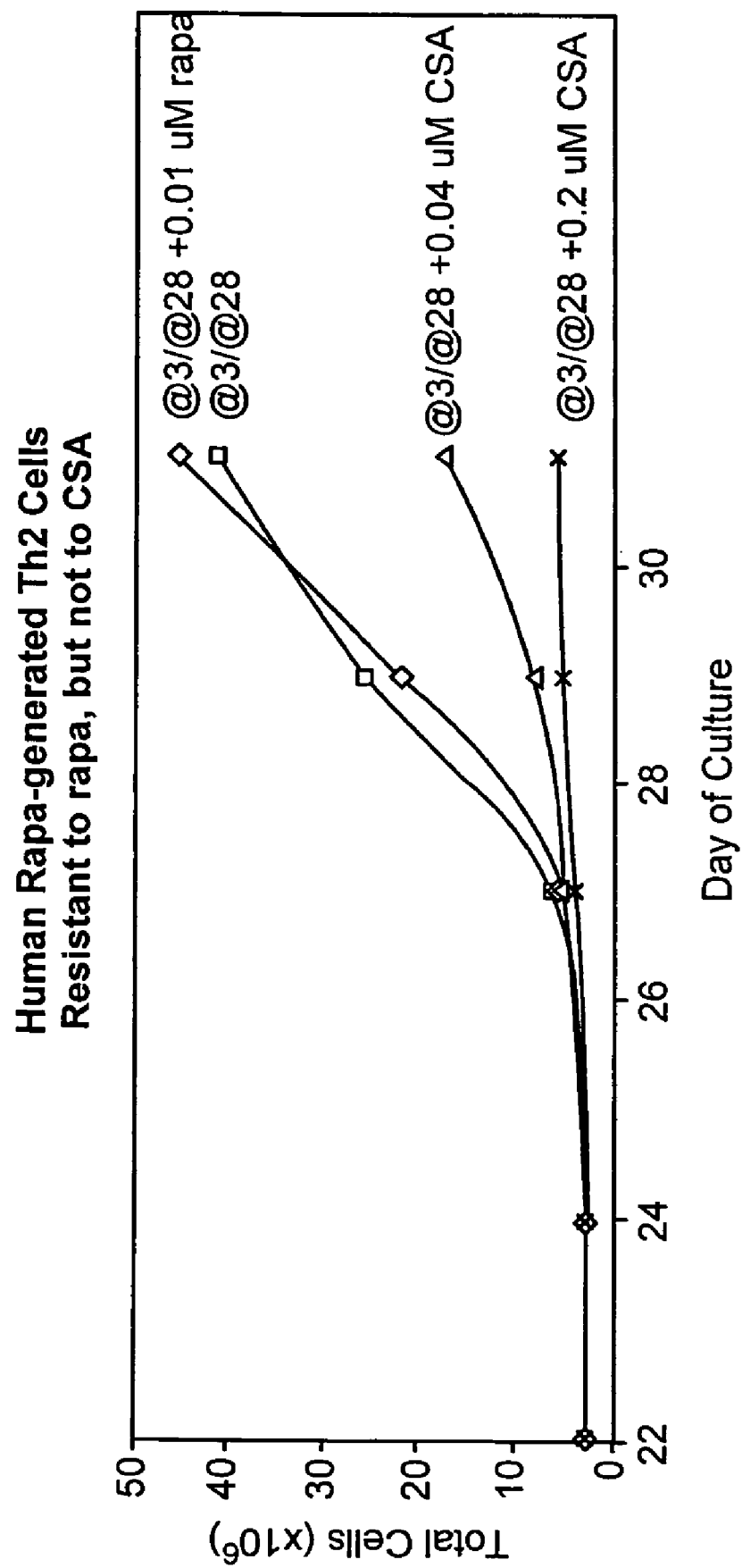
FIG. 25 is a graph showing CD3, CD28 re-stimulation of rapamycin-generated Th2 cells with or without 0.01 µM rapamycin.

To evaluate whether a similar rapamycin biology exists in human CD4 cells, and to initiate a translation of rapamycin-generated Th2 cells into clinical trials, experiments of human CD4 cell co-stimulation in the presence or absence of rapamycin were performed. FIG. 23 shows the results of CD4 expansion from n=4 normal donors either without (left panel) or with rapamycin (1.0 μM; right panel). In vitro conditions consisted of anti-CD3, anti-CD28 co-stimulation with IL-4 and IL-2. As this figure shows, without rapamycin, a three to four log CD4 Th2 cell expansion occurred over 20 days in culture. In contrast, addition of rapamycin was associated with an initial significant reduction in CD4 cell numbers in the first six days of culture, followed by a period of CD4 expansion. This pattern of CD4 cell contraction/expansion appeared consistent with an initial CD4 cell selection process, followed by a period of rapamycin-resistant expansion. To begin evaluating this possibility, we expanded n=4 donor cultures for six days in the presence of rapamycin, and then either continued to propagate the cultures in rapamycin (FIG. 24, left panel) or in the absence of rapamycin (FIG. 24, right panel). As this figure shows, the post day 6 CD4 cells expanded significantly whether maintained with or without rapamycin (without rapamycin >with rapamycin). Experiments were then performed to evaluate whether rapamycin-generated Th2 cells were indeed relatively resistant to rapamycin, and to evaluate whether cross-resistance to CSA existed (FIG. 25). As this figure shows, CD3, CD28 re-stimulation of rapamycin-generated Th2 cells with or without 0.01 μM rapamycin yielded a similar degree of CD4 cell expansion. This concentration of rapamycin was shown in the same experiment to significantly reduce expansion of conventionally propagated Th2 cells. In contrast, rapamycin-generated Th2 cells were sensitive to inhibition by CSA at concentrations of either 0.2 or 0.04 μM. As such, the rapamycin-generated Th2 cells appear to have resistance to further rapamycin challenge, without cross-resistance to CSA.

Example 12

Purity of Th1/Th2 Cells

Figure 26:
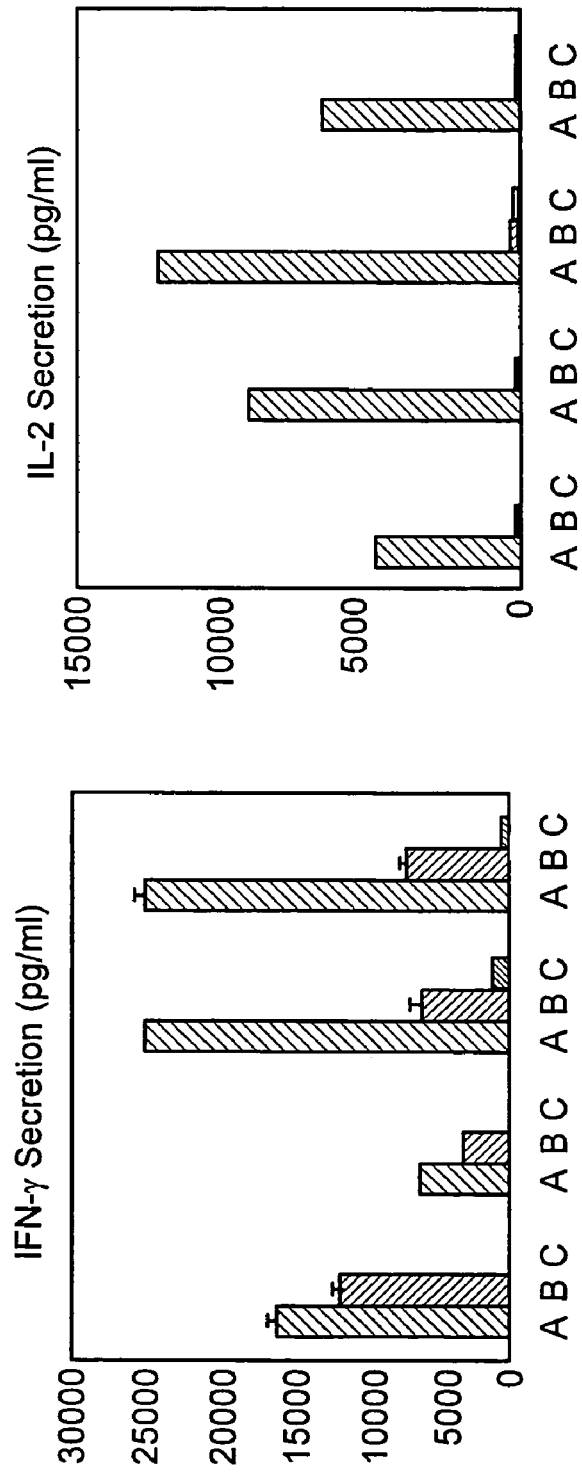
FIG. 26 is a graph showing that cells propagated under Th2 conditions and rapamycin had an increased Th2 cytokine purity, as evidenced by reduction in capacity for IFN-γ secretion.
Figure 27:
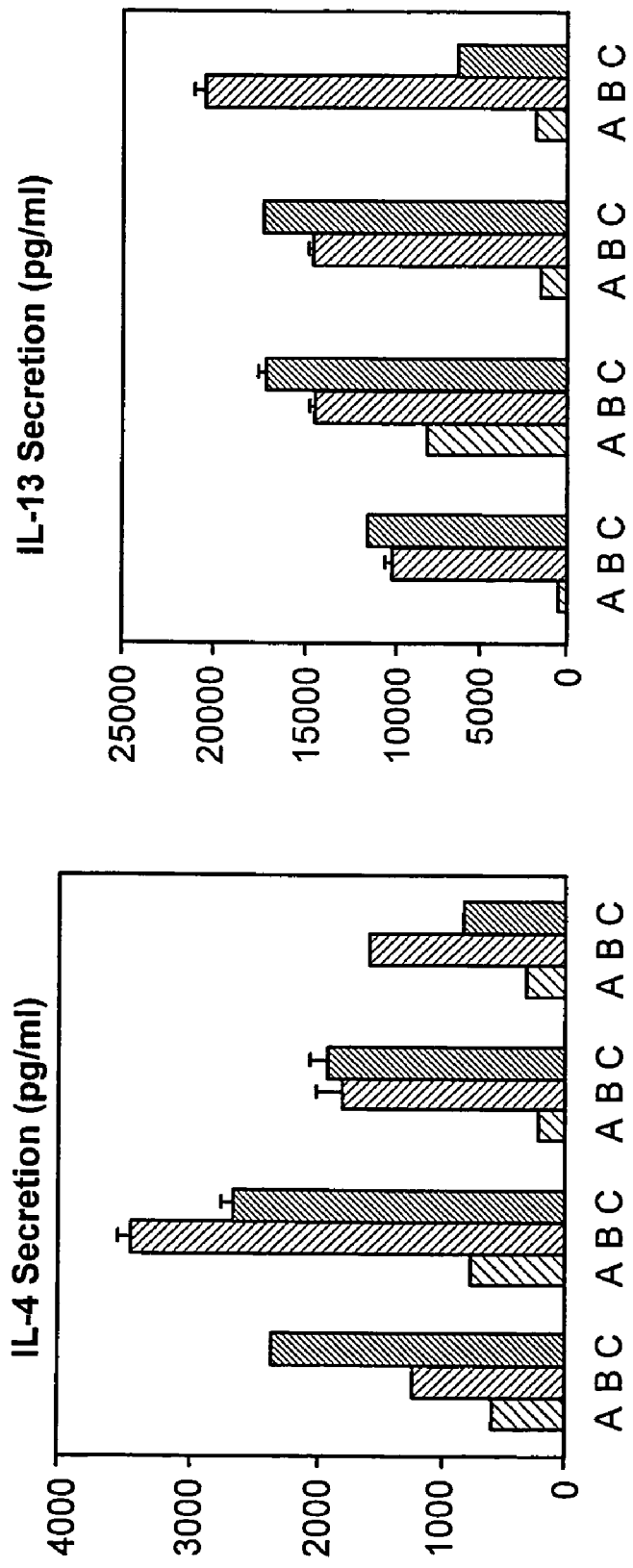
FIG. 27 is a graph showing that rapamycin-generated Th2 cells had an increased capacity for secretion of the type II cytokines IL-4 and IL-13.

The human Th2 cultures were additionally evaluated for issues of Th1/Th2 purity. As FIG. 26 shows, cells propagated under Th2 conditions and rapamycin had an increased Th2 cytokine purity, as evidenced by reduction in capacity for IFN-γ secretion. This increased Th2 purity (reduced IFN-γ) was observed simply by an initial day 0 to day 6 rapamycin exposure, and was more fully realized by continued presence of rapamycin in the Th2 culture. This result indicated that rapamycin may operate initially by some CD4 cell subset selection mechanism (acute process), and additionally by a more chronic mechanism that maintains Th2 purity. Surprisingly, rapamycin generated Th2 cells had a dramatic reduction in IL-2 secretion, with this effect occurring during the initial six days of rapamycin exposure. Concomitant with these reductions in type I cytokine contaminations, FIG. 27 demonstrates that rapamycin-generated Th2 cells had an increased capacity for secretion of the type II cytokines IL-4 and IL-13. In sum, rapamycin enhanced the ability of CD28 co-stimulation and cytokines to generate human Th2 cells, both on the basis of reducing Th1 cytokines and increasing Th2 cytokines.

Figure 28:
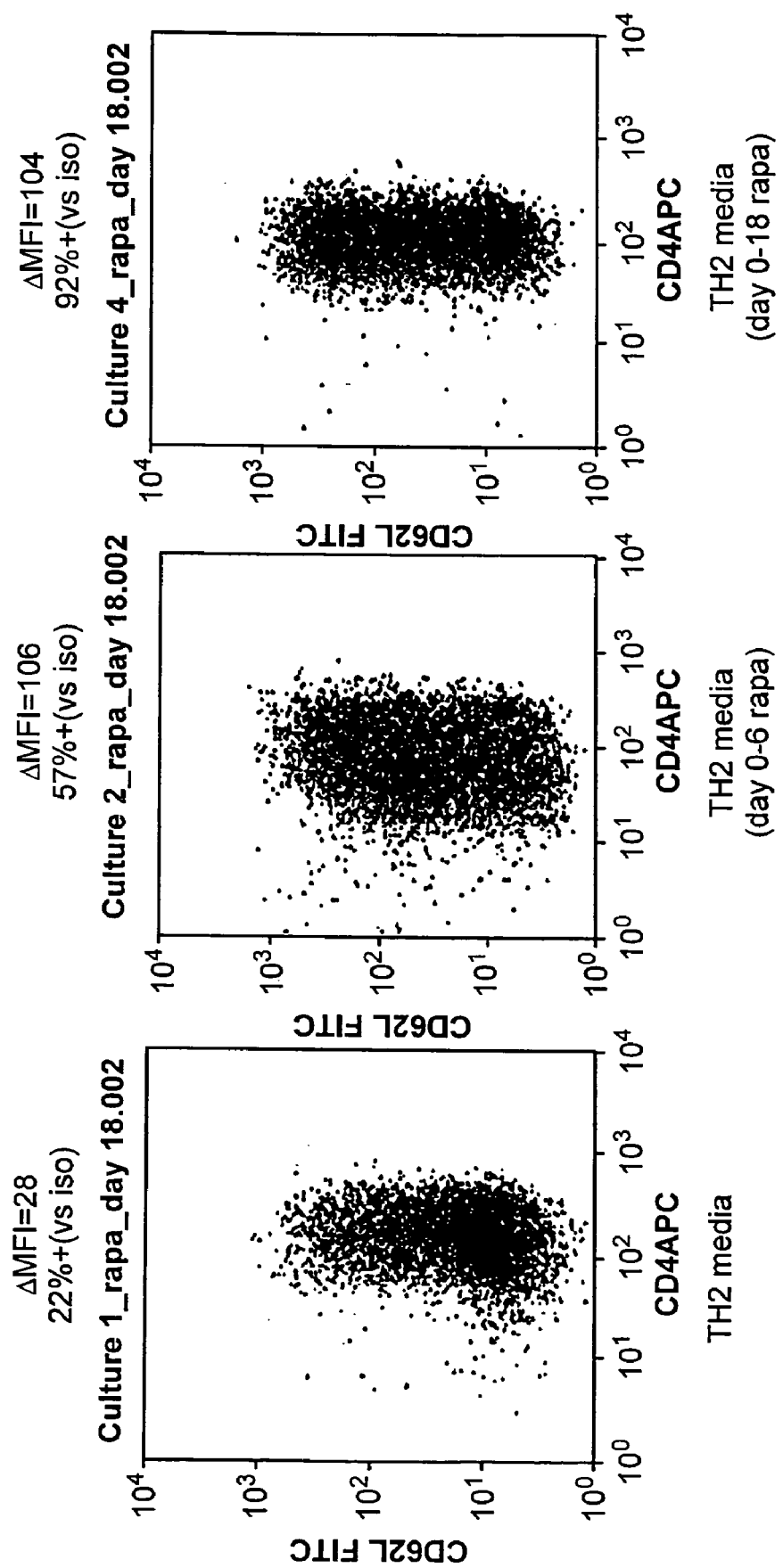
FIG. 28 is a graph showing that rapamycin-generated Th2 cells had increased expression of CD62L relative to control Th2 cells; the increase in CD62L was most marked in Th2 cultures that were continuously exposed to rapamycin.

Similar to results in the murine system, rapamycin-generated Th2 cells in the human system displayed a more naïve CD4 cell phenotype relative to conventionally co-stimulated Th2 cells. As FIG. 28 shows, rapamycin-generated Th2 cells had increased expression of CD62L relative to control Th2 cells; the increase in CD62L was most marked in Th2 cultures that were continuously exposed to rapamycin. Also similar to the murine studies, human rapamycin-generated Th2 cells also expressed significantly reduced CD40L relative to control Th2 cells; because CD40L is a molecule preferentially expressed on Th1 cells, this observation further supports the conclusion that rapamycin facilitates generation of a human Th2 cell with enhanced purity.

Example 13

Rapamycin Treated Naïve CD4+ T Cells

In an attempt to tie these results together, we predicted that naïve CD4 cells would be more resistant to rapamycin, and would therefore exhibit a higher cloning efficiency after co-stimulation during rapamycin exposure. To this extent, naïve or memory human CD4 cells were purified by flow sorting, and co-stimulated either with or without rapamycin (results in FIG. 31). As this figure shows, naïve sorted CD4 cells had only a nominal reduction in CD4 expansion in rapamycin relative to the control culture (~25% reduction in CD4 yield). In contrast, memory CD45RO+ sorted cells not only had reduced expansion to CD28 co-stimulation, but also had a more significant degree of rapamycin-associated reduction in CD4+ T cell expansion (~50% reduction). Together, these results show that naïve CD4+ T cells are more resistant to rapamycin inhibition, perhaps in part through their increased expression of MDR molecules, which results in co-stimulation of CD4+ T cells that have a more naïve effector phenotype and a greater capacity for Th2 polarization.

Example 14

Reduction of GVHD by Th2 Cells

Materials and Methods

Lymphocyte Harvest and T Cell Isolation from Donor (a) After determination that donor is HLA-matched with recipient, donor will undergo a 2 to 5 liter apheresis procedure using a CS-3000 or an equivalent machine.

(b) Apheresis product will be subjected to counterflow centrifugal elutriation by the standard operating procedure of the NIH DTM.

(c) The lymphocyte fraction of the elutriation product (120 to 140 fraction) will be depleted of B cells by incubation with an anti-B cell antibody (anti-CD20; Nexell) and an anti-CD8 antibody (Nexell) and sheep anti-mouse magnetic beads (Dynal; obtained through Nexell) by a standard operating procedure of the NIH DTM using the MaxCep Device (Nexell). Flow cytometry will be performed to document that CD8+ T cell contamination is <1%.

(d) The resultant CD4-enriched donor lymphocyte product will be cryopreserved using an NIH DTM protocol in aliquots of 50 to 200×10$^6$ cells/vial. Sterility of the population will not be tested at this early stage of the Th2 cell generation procedure; such testing will occur after final co-culture of donor CD4 cells.

Peripheral Blood Stem Cell Harvest from Donor a) Immediately following lymphocyte harvest, the donor will receive filgrastim as an outpatient (10 µg/kg/day each morning; subcutaneously) for 5, 6, or 7 days. The donor should take the filgrastim as early as possible upon awakening in the morning. This is especially important on days 5, 6, and 7 of the injections.

b) Apheresis will typically be performed on days 5 and 6 of this regimen. On some occasions, sufficient numbers of CD34+ cells might be obtained with a single apheresis on day 5; on other occasions, it may be necessary to perform apheresis on days 5, 6, and 7 to reach the target CD34+ cell number ($\geq$4×10$^6$ per kg). The donor will be instructed to take filgrastim for the complete 7 day period, unless notified by the transplant team that adequate CD34+ cells were harvested before day 7.

c) If $\geq$3×10$^6$ CD34+ cells per kg are harvested after apheresis on days 5, 6, and 7, no further mobilization or apheresis will be performed, and the patient will be eligible to receive the stem cell transplant with that dose of CD34+ cells.

d) In the event that less than 3×10$^6$ CD34+ cells per kg are harvested after apheresis on days 5, 6, and 7, the donor will be given two weeks of rest, and then will be re-treated with filgrastim followed by repeat peripheral blood stem cell harvesting.

e) A 15 to 25 liter large volume whole blood pheresis will be performed in the NIH DTM via a 2-armed approach or via a temporary central venous catheter in the femoral position using the Baxter CS3000Plus, Cobe Spectra, or an equivalent instrument. This procedure typically takes 4 to 6 hours.

f) Apheresis procedure will typically use ACD-A anti-coagulant; alternatively, partial anti-coagulation with heparin may be utilized.

g) The apheresis product will be cryopreserved and stored at −180 degrees Celsius in a solution containing Plasmalyte A, Pentastarch, human serum albumin, DMSO, and preservative free heparin (10 U/ml).

h) The concentration of CD34+ cells in the apheresis product will be determined by flow cytometry, and the number of CD34+ cells in each cryopreserved bag calculated.

i) If the donor and host are ABO incompatible, red blood cells will be depleted from the stem cell product by standard DTM protocols.

In Vitro Generation of Donor CD4+ Th2 Cells a) Cryopreserved donor CD4+ T cells will be resuspended to a concentration of 0.3×10$^6$ cells per ml. Media will consist of X-Vivo 20 supplemented with 5% heat-inactivated autologous plasma.

b) The donor CD4+ T cells will be cultured in filtered flasks at 37° C. in 5% CO2 humidified incubators. At the time of culture initiation, T cells will be stimulated with anti-CD3/anti-CD28 coated magnetic beads (3 to 1 ratio of beads to T cells).

c) At the time of co-culture initiation and on day 2 of culture, the following reagents will be added: recombinant human IL-4 (obtained through cross-filing on CTEP IND of Shering IL-4; 1000 I.U. per ml), and recombinant human IL-2 (purchased from Chiron Therapeutics; 20 I.U. per ml).

d) After day 2, cells will be maintained at a concentration of 0.25 to 1.0×10$^6$ cells per ml by the addition of fresh X-Vivo 20 media supplemented with autologous plasma (5%), IL-2 (20 I.U./ml), and IL-4 (1000 I.U./ml).

e) The median cell volume will be determined using a Multisizer II instrument (Coulter). When the T cell volume approaches 500 fl (acceptable range of 650 to 350), the T cells will be restimulated with anti-CD3/anti-CD28 beads; typically, this time of restimulation will be after 8 to 12 days of culture.

f) Bead restimulation will be at a bead to T cell ratio of 3:1. T cell concentration will be 0.2×10$^6$ cell/ml. Media will again consist of X-Vivo 20 supplemented with autologous plasma (5%), IL-2 (20 I.U./ml), and IL-4 (1000 I.U./ml).

g) After bead restimulation, CD4 cells will be maintained at a concentration of 0.25 to 1.0×106 cells per ml by the addition of fresh X-Vivo 20 media supplemented with autologous plasma (5%), IL-2 (20 I.U./ml), and IL-4 (1000 I.U./ml).

h) When the CD4 cell mean cell volume approaches 500 fl (acceptable range of 650 to 350), the cells will be harvested and cryopreserved by the NIH DTM method in protocol-relevant quantities for administration on study. It is anticipated that the total time of CD4 cell culture will be 15 to 20 days.

i) If an adequate numbers of CD4 cells is obtained, then such cells may be available for administration on this protocol as a Th2 infusion.

j) The following will be the minimal phenotypic requirements of any particular Th2 cell culture to qualify for cryopreservation with subsequent administration:

1. Presence of predominately CD4+ T cells by flow cytometry (greater than 70% CD4+ T cells, and less than 5% contaminating CD8+ T cells).

2. In addition, the cryopreserved product will be tested for sterility with both fungal and bacterial cultures, through the ongoing testing done on cell products processed in the NIH Department of Transfusion Medicine. In addition, the CD4 Th2 cell product will be tested for endotoxin content by the limulus assay. Cell products positive for fungal, bacterial, or endotoxin content will be discarded.

Pre-Transplant Induction Chemotherapy a) After cell products have been harvested from the patient, chemotherapy will be administered as an outpatient. All patients will receive at least one cycle of induction chemotherapy, even if their CD4 count is less than 50 cells per µl at the time of study entry. At this point in the protocol or earlier at the time of cell harvesting, placement of permanent central venous access may be requested.

| Cycle 1 of Induction Chemotherapy | | |
| --- | --- | --- |
| Drug | Dose | Days |
| Fludarabine | 25 mg/m² per day IV Infusion over 30 minutes, Daily for 3 days | Days 1, 2, 3 |
| Etoposide | 50 mg/m² per day continuous IV Infusion over 24 hours, Daily for 3 days | Days 1, 2, 3 |
| Doxorubicin | 10 mg/m² per day continuous IV Infusion over 24 hours, Daily for 3 days | Days 1, 2, 3 |
| Vincristine | 0.5 mg/m² per day continuous IV Infusion over 24 hours, Daily for 3 days | Days 1, 2, 3 |
| Cyclophosphamide | 600 mg/m² IV Infusion over 2 hr | Day 4 |
| Prednisone | 60 mg/m² per day orally, daily for 4 days | Days 1, 2, 3, 4 |
| Filgrastim | 10 ug/kg per day subcutaneously | Daily from day 5 Until ANC > 1000/ul for two days | b) Fludarabine will be administered i.v. at a dose of 25 mg/m2 per day for three days (days 1, 2, and 3). Fludarabine will administered over a 30 minute interval. Steroids should not be used as an anti-emetic during this chemotherapy regimen.

d) Cyclophosphamide will be administered i.v. at a dose of 600 mg/m2 over 30 minutes on day 4.

d) Etoposide will be administered at a dose of 50 mg/m2 per day by continuous intravenous infusion for three days (days 1, 2, and 3).

e) Doxorubicin will be administered at a dose of 10 mg/m2 per day by continuous intravenous infusion for three days (days 1, 2, and 3).

f) Vincristine will be administered at a dose of 0.5 mg/m2 per day by continuous intravenous infusion for three days (days 1, 2, and 3).

g) Prednisone will be administered at a dose of 60 mg/m2 per day orally for four days (days 1, 2, 3, and 4).

h) Filgrastim will be initiated on day 5 at a dose of 10 µg/kg/day; G-CSF will be continued until the ANC is greater than 1000 cells per µl on two consecutive days.

Determination of Number of Cycles of Induction Chemotherapy (a) Because the primary purpose of the induction chemotherapy is to establish severe host immune T cell depletion prior to the allotransplant, the number of induction chemotherapy cycles administered will be determined by the severity of immune T cell depletion observed.

(b) The CD4 count will be measured by flow cytometry in the interval of day 15 to day 21 of the fludarabine/EPOCH chemotherapy. If there are 50 or more CD4 cells per µl of blood during this interval, further cycles of induction chemotherapy will be administered (in an attempt to achieve greater immunosuppression prior to transplantation). However, a maximum of three cycles of induction chemotherapy will be administered.

(c) Patients will receive the second cycle of chemotherapy on day 22 after the first cycle was initiated. However, an additional two weeks of recovery time before administration of the second cycle may be provided if medically indicated (for example, for delay in neutrophil recovery, documented infection, or other complication resulting from the induction chemotherapy regimen).

(d) If there are less than 50 CD4 cells per µl of blood when measured within days 15 to 21 after fludarabine/EPOCH administration, then that patient will receive the transplant preparative regimen.

(e) If a patient develops neutropenia of less than 500 PMN's per µl for more than seven days during any cycle of induction chemotherapy, the patient will receive no further induction chemotherapy. At that point, they will receive the transplant preparative regimen (even if the CD4 count is not less than 50 cells per µl).

(f) A maximum of three cycles of induction chemotherapy can be administered. Patients will then proceed to the preparative regimen chemotherapy (even if the CD4 count is still greater than 50 cells per µl).

(g) If a patient develops progressive disease at any point during induction chemotherapy cycles, such a patient will proceed to the transplant preparative regimen (independent of the CD4 count).

Determination of Cycle 2 and Cycle 3 Dose Escalation a) If the first cycle of induction chemotherapy does not reduce the CD4 count to a value below 50 cells per µl and does not result in febrile neutropenia or prolonged neutropenia as evidenced by two consecutive bi-weekly ANC values less than 500 cells per µl, then the next cycle of induction chemotherapy may be dose escalated.

b) Dose escalation will consist of a 20% escalation in the daily dose of fludarabine, etoposide, adriamycin, and cyclophosphamide.

c) If a third cycle of chemotherapy is required (CD4 count still greater than 50) and febrile neutropenia or two timepoints of ANC less than 500 did not occur after cycle 2, then the third cycle of induction chemotherapy may be administered at a further 20% escalation of doses administered for cycle 2.

Dose Reduction of Pre-Transplant Induction Chemotherapy (a) In the event that more than one patient experiences a period of neutropenia (ANC less than 500 per µl) for more than 10 days, the etoposide, doxorubicin, vincristine, and prednisone will be reduced from three days to two days of administration. The doses of these medications will remain unchanged. In the event of this change, the cyclophosphamide and filgrastim will be given on day 3.

(b) The same schedule modification described in subsection a) (above) will be performed if any grade IV toxicity by the NCI Common Toxicity Criteria is observed in more than one patient.

Transplant Procedure: Preparative Regimen a) On day 22 after the final cycle of induction chemotherapy, patients will be eligible to receive the following transplant preparative regimen. Therefore; day 22 of the final induction chemotherapy cycle will be transplant day −6. However, in cases where additional recovery time is required (for example, due to prolonged neutropenia, documented infection, or other medical complications of the induction regimen), an additional two weeks of recovery time may be utilized prior to initiation of the transplant preparative regimen.

| Transplant Preparative Regimen | | |
| --- | --- | --- |
| Drug | Dose | Days |
| Fludarabine | 30 mg/m$^2$ per day IV Infusion over 30 minutes, daily for 4 days | Transplant Days −6, −5, −4, −3 |
| Cyclophosphamide | 1200 mg/m$^2$ per day IV Infusion over 2 hours, daily for 4 days | Transplant Days −6, −5, −4, −3 |
| Mesna | 1200 mg/m$^2$ per day by continuous IV Infusion, daily for 4 days (start 1 hr before cyclophosphamide) | Transplant Days −6, −5, −4, −3 | b) Fludarabine will be administered i.v. over 15 to 30 minutes at a dose of 30 mg/m$^2$/day on days −6, −5, −4, and −3.

c) Cyclophosphamide will be administered at a dose of 1200 mg/m$^2$/day over a two hour infusion on days −6, −5, −4, and −3.

d) Mesna will be administered at a dose of 1200 mg/m$^2$ per day by continuous i.v. infusion on days −6, −5, −4, and −3. The mesna should be started one hr prior to the cyclophosphamide. Bag #1 of the mesna will be 150 mg/m$^2$ in 250 ml over a 3 hr infusion (thus stopping when cyclophosphamide ends). Then, mesna will be given at 1200 mg/m$^2$ in 500 ml over 24 hour infusion, for four days (days −6, −5, −4, and −3).

Transplant Procedure: GVHD Chemoprophylaxis with Cyclosporine (CSA)

a) Cyclosporine will be initiated on the day −1 before the transplant. CSA will be administered by i.v. infusion at a dose of 2 mg/kg. CSA will administered 12 hours, with each infusion administered over a 2 hour period.

b) In the first two weeks post-transplant, CSA dose may be modified to achieve adequate steady-state CSA levels. Once this intravenous dose is established and the patient is able to tolerate oral feedings (typically by day 14 post-transplant); then CSA will be switched to the oral formulation. Conversion of CSA to the oral formulation is typically performed by multiplying the adequate i.v. dose by a factor of 1.5 to 2.0. Patients will then be maintained on oral CSA on a 12 hour schedule, with a goal to achieve steady state trough CSA levels of 200 ng/ml CSA (acceptable range: 150 to 250 ng/ml).

c) This dose of CSA will continue until day 100 post-transplant, at which point it will be gradually tapered as long as the level of GVHD is less than grade 2. Taper will consist of a 5 to 10% dose reduction each week (patient will then be taken off of CSA by day 180 post-transplant).

| Taper Step | Days post-BMT | CSA Dosage (mg/kg/dose) |
| --- | --- | --- |
| Taper Step 1 | 101-107 | 95% of Maintenance Dose (M.D.) |
| Taper Step 2 | 108-114 | 90% of M.D. |
| Taper Step 3 | 115-121 | 85% of M.D. |
| Taper Step 4 | 122-128 | 80% of M.D. |
| Taper Step 5 | 129-135 | 70% of M.D. |
| Taper Step 6 | 136-142 | 60% of M.D. |
| Taper Step 7 | 143-149 | 50% of M.D. |
| Taper Step 8 | 150-156 | 40% of M.D. |
| Taper Step 8 | 157-163 | 30% of M.D. |
| Taper Step 10 | 164-170 | 20% of M.D. |
| Taper Step 11 | 171-180 | 10% of M.D. |

Transplant Procedure: Allogeneic Peripheral Blood Stem Cell Transplantation a) On day 0, the patient will receive the cryopreserved PBSC.

b) The cryopreserved PBSC product will be thawed and administered intravenously immediately. The target dose of the PBSC is $\geq 4 \times 106$ CD34$^+$ cells per kg. However, if donor apheresis on days 5, 6, and 7 yields a total of $\geq 3 \times 10^6$ CD34$^+$ cells per kg, this level of CD34$^+$ cell dose will also be allowed.

(a) No steroids will be allowed in the management of DMSO-related toxicities (chills, muscle aches) that may occur immediately after cellular infusion (diphenhydramine and meperidine are allowed).

Transplant Procedure: Donor Th2 Cell Administration a) On day 1 of the transplant procedure, the cryopreserved donor Th2 cells will be thawed and immediately administered intravenously.

b) No steroids will be allowed in the management of DMSO-related toxicities (chills, muscle aches) that may occur immediately after cellular infusion (diphenhydramine and meperidine are allowed).

c) The determination of whether a Th2 cell infusion is safe will be based on the presence or absence of hyperacute GVHD and of any grade 4 or 5 toxicity attributable to the Th2 cells that occurs in the first 14 days post-transplant.

d) For this study, hyperacute GVHD will be defined as a severe level of acute GVHD (grade III or IV) that occurs within the first 14 days post-transplant.

e) The initial three patients will be enrolled to Th2 cell dose level #1 ($5 \times 10^6$ Th2 cells/kg). If no hyperacute GVHD or grade 4 or 5 toxicity attributable to the Th2 cells is observed in these initial three patients, then it will be determined that this dose level is safe, and accrual to dose level #2 will commence. If hyperacute GVHD or grade 4 or 5 toxicity attributable to the Th2 cells is observed in any of the initial three patients, then accrual to dose level #1 will be expanded to include a total of six patients. If two patients in six develop hyperacute GVHD or a grade IV toxicity related to the Th2 cells, then it will be determined that dose level #1 is not safe, and further accrual to the study will stop at that point. If only one of the six patients experiences such an adverse effect, then it will be determined that dose level #1 is safe, and accrual will proceed to dose level #2.

f) Three patients may then be enrolled to Th2 cell dose level #2 ($2.5 \times 10^7$ Th2 cells/kg). The same accrual and stopping rules will apply to this dose level as those used for dose level #1. As such, either three or six patients will be accrued to dose level #2.

g) If it is determined that Th2 cell dose level #2 is safe, accrual to the final dose level #3 will start (Th2 cell dose of $1.25 \times 10^8$ cells/kg). Six patients in total will be evaluated on dose level #3. If more than one patient on dose level #3 develops hyperacute GVHD or grade 4 or 5 toxicity attributable to the Th2 cells, then accrual to dose level #3 will stop.

h) In the phase II component of this study, eighteen (18) additional patients will receive Th2 cells at either dose level #2 or level #3. To help ensure that the Th2 cells continue to be safely administered in this expanded cohort, the same accrual and stopping rules pertaining to severe toxicity attributed to the Th2 cells will be continued. Specifically, 24 total patients (6 in the Phase I cohort, 18 in the expanded Phase II cohort) will be evaluated at either Th2 cell dose level #2 or level #3.

Accrual and stopping rules will be applied after each cohort of six patients. Therefore, if at any point, the frequency of severe toxicity attributable to the Th2 cells exceeds 1/6, 2/12, 3/18, or 4/24, then accrual to that treatment arm will be stopped.

Treatment of Persistent Disease Post-Transplant: DLI and Other Therapy (a) Patients with persistent or progressive malignant disease post-SCT will be eligible to receive donor lymphocytes ("delayed lymphocyte infusion" or DLI). DLI may be administered alone or after chemotherapy administration.

(b) Donor lymphocytes will be collected by apheresis, either in steady state (no donor therapy) or after G-CSF mobilization. The donor product may be enriched for lymphocytes by Ficoll-Hypaque procedure as per NIH DTM protocol. Alternatively, in cases where additional donor stem cells are desired, the donor product may be administered without lymphocyte purification. DLI may be sequentially administered, with initial dosing at $1 \times 10^6$ CD3+ T cells per kg, and with subsequent dose increases to $1 \times 10^7$ and $1 \times 10^8$ per kg.

(c) Alternatively, persistent or progressive disease may be treated with any approved therapy thought to be in the best standard care of the patient, such as chemotherapy, cytokine therapy, or monoclonal antibody therapy. Alternatively, patients with relapse may receive therapy on other NCI protocols.

Evaluation of Pre-Transplant Induction Chemotherapy Cycles a) Blood samples (10 cc in green-top heparinized tube) will be drawn to evaluate the effects of the combination fludarabine/EPOCH regimen on host immune depletion.

b) This sample should be drawn just prior to each cycle of induction chemotherapy (within six days of the next cycle).

c) Experiments will consist of flow cytometry to detect depletion of lymphoid versus myeloid subpopulations during induction chemotherapy.

Determination of Donor/Host Chimerism Post-Transplant a) Blood samples (10 cc in green-top heparinized tube) will be drawn to evaluate the extent of donor versus host chimerism post-transplant. Samples will be sent to the Milwaukee Blood Banking Center for VNTR-PCR analysis of chimerism. If a result of mixed chimerism is obtained at day 15 post-transplant, subsequent draws may be increased to 60 ml of blood so that cell sorting experiments can be performed to evaluate chimerism in cell subsets.

b) Timepoints for chimerism analysis will be at day 15, day 30, and day 100 post-transplant. After day 100, chimerism may be determined if clinically indicated (in the setting of disease relapse).

c) Chimerism will be evaluated by a PCR-based assay, performed by the Milwaukee Blood Banking Center.

Statistical Section a) One objective of this study is to establish a safe and feasible dose of donor Th2 cells to administer after allogeneic PBSCT. Once such a determination is made, eighteen (18) additional patients will be treated at that Th2 cell dose level in order to gain more safety information relating to Th2 cells, and to determine the incidence and severity of acute GVHD associated with allogeneic SCT containing Th2 cells.

b) The 18 additional Th2 recipients will either be treated at Th2 dose level #2 ($25 \times 10^6$/kg) or at Th2 dose level #3 ($125 \times 10^6$/kg). The incidence of grade II to IV acute GVHD at Th2 dose level #2 is 2/6; results from Th2 dose level #3 are not known, as accrual to this cohort has just now been initiated. If Th2 dose level #3 is associated with unacceptable toxicity (more than 1/6 incidence of severe toxicity) or significant GVHD (more than 2/6 cases of grade II to IV acute GVHD), the additional 18 patients will be treated on Th2 dose level #2. If recipients of Th2 dose level #3 have 0/6 or 1/6 cases of severe toxicity and 0/6, 1/6, or 2/6 cases of grade II to IV acute GVHD, the additional 18 patients will be treated at dose level #3. In the event that the high dose of Th2 cells can not be consistently generated, then the phase II component of accrual may be initiated at dose level #2.

c) The incidence and severity of acute GVHD in the cohort of 24 patients receiving Th2 cells at dose level #2 or #3 will be determined, and compared to the initial protocol cohort of 19 patients receiving transplantation without Th2 cells. In this protocol, we hypothesize that recipients of the Th2 cells will have reduced GVHD relative to non-Th2 recipients. In the cohort of non-Th2 recipients, the incidence of grade II to grade IV acute GVHD was 12/19. Based on this experience, one can conclude that the true rate of grade II to IV GVHD without Th2 cells is approximately 60%. In this protocol, we hypothesize that the expanded cohort of n=24 Th2 recipients will have a significantly reduced incidence of grade II to IV acute GVHD. Based on our current results, we predict that the incidence of grade II to IV acute GVHD will be reduced from 60% without Th2 cells to 20% with Th2 cells. The predicted power to detect a Th2-mediated reduction in grade II to IV acute GVHD from 60% to 20% in the expanded Th2 cohort will depend on the incidence of grade II to IV GVHD observed on that arm during the phase I aspect of patient accrual. Using a two-tailed conditional power statistical analysis at the p=0.05 level, accrual of 18 additional subjects to a Th2 cell treatment arm will provide either 72%, 87%, or 95% power to detect a Th2-mediated reduction in the incidence of grade II to IV GVHD from 60% to 20%. Specifically, the initial incidence, from the phase I accrual, of grade II to IV acute GVHD for the Th2 cell dose selected for the phase II component will be either 2/6, 1/6, or 0/6. For these conditions, the statistical power for detecting a reduction in grade II to IV GVHD from 60% to 20% would be 72%, 87%, or 95%, respectively.

d) To help ensure that the Th2 cells continue to be safely administered in the expanded cohort, the same accrual and stopping rules pertaining to severe toxicity attributed to the Th2 cells will be continued. Specifically, 24 total patients (6 in the Phase I cohort, 18 in the expanded Phase II cohort) will be evaluated at either Th2 cell dose level #2 or level #3. Accrual and stopping rules pertaining to severe toxicity attributable to Th2 cells will be applied after each cohort of six patients. Therefore, if at any point, the frequency of severe toxicity attributable to the Th2 cells exceeds 1/6, 2/12, 3/18, or 4/24, then accrual to that treatment arm will be stopped.

e) An additional accrual and stopping rule pertaining to acute GVHD will be utilized in the expanded Phase II cohort. The incidence of grade II to IV acute GVHD in non-Th2 recipients was 12/19, or 63%. In the expanded cohort of Th2 recipients, the incidence of grade II to IV acute GVHD will be calculated on an ongoing basis and reviewed at the weekly protocol meeting. If at any point in protocol implementation the incidence of grade II to IV acute GVHD in Th2 recipients is 60% or greater, then further accrual to the protocol will be stopped.

Up to 2/6 cases of grade II to IV acute GVHD will be allowed for expansion of Th2 accrual to the phase II component. Therefore, it is possible that the phase II component of the Th2 accrual may be stopped after 4 patients (in the event that each develops grade II to IV acute GVHD).

Results

We demonstrated in murine models that Th2-mediated regulation of GVHD is not associated with an increased rate of graft rejection. In these studies, supplementation of marrow allografts with Th2 cells represents a strategy for reducing the detrimental aspect of allogeneic T cell administration (GVHD) while preserving the beneficial ability of donor T cells to prevent allograft rejection. In this clinical protocol, the G-CSF mobilized allograft contains approximately $1\times10^8$ CD4$^+$ T cells per kg of recipient weight. In the phase I aspect of this protocol, patients will receive additional donor Th2 cells, with the final Th2 cell dose being $1.25\times10^8$ Th2 cells per kg of recipient weight. As such, this design allows for a safety evaluation for administering donor Th2 cells in a dose range that we hypothesize would be associated with a reduction in GVHD (a 1:1 ratio of unmodified donor CD4$^+$ T cells to donor Th2 cells). Through administration of Th2 cells on the day following peripheral blood stem cell transplantation, we hypothesize that the unmanipulated T cells contained in the mobilized stem cell product will maintain their ability to prevent graft rejection but will have a reduced capacity to induce severe acute GVHD.

Complete Donor Engraftment and Development of GVHD

In this pilot study, we will utilize an induction chemotherapy regimen consisting of fludarabine in combination with the agents contained in the EPOCH regimen. The primary purpose of administering this chemotherapy cycle is to achieve a high level of host immunosuppression prior to allotransplantation. Our murine data indicate that very severe levels of host T cell depletion are required for the engraftment of fully-MHC mismatched allografts after fludarabine-based chemotherapy. As such, the development of induction chemotherapy regimens which induce severe host T cell depletion without myeloablation is a highly desirable goal. To develop such therapies, we have attempted to reduce the CD4 count to less than 50 cells per μl prior to administration of the transplant preparative regimen. This level of host CD4$^+$ T cell depletion is associated with significant immunosuppression and a reduced ability to reject allogeneic cells in patients with B cell malignancy.

Seven patients were treated with this fludarabine and EPOCH induction chemotherapy regimen prior to allogeneic PBSCT. In each case, we have noted a marked reduction in patient T cells, and have also observed either stable disease or partial disease responses to the chemotherapy. As such, we have observed that the induction chemotherapy regimen to be utilized on this pilot study achieves two important conditions prior to allogeneic PBSCT: immune depletion for the purpose of preventing graft rejection, and reduction or stabilization in malignant disease.

After such induction chemotherapy, patients receive preparative regimen chemotherapy consisting of fludarabine and cyclophosphamide. In the initial six patients treated with this regimen, rapid and complete donor engraftment has been observed in all recipients (98 to 100% donor elements by day 14 post-transplant). As such, this immunoablative induction and preparative regimen chemotherapy is very effective for the prevention of allogeneic stem cell graft rejection in the non-myeloablative transplant setting.

Allogeneic PBSCT in the Treatment of Leukemia and Lymphoid Neoplasia

Allogeneic bone marrow transplantation represents a potentially curative treatment for patients with multiple hematologic and lymphoid malignancies. The allogeneic graft-versus-leukemia effect contributes to disease remission in acute lymphocytic leukemia, acute myelogenous leukemia, chronic lymphocytic leukemia, chronic myelogenous leukemia, indolent and high-grade non-Hodgkin's lymphoma, Hodgkin's lymphoma, multiple myeloma, and myelodysplastic syndrome. Because the EPOCH regimen has an established response rate in patients with chemotherapy-refractory lymphoid malignancy, such patients will be eligible for this protocol. The addition of fludarabine to EPOCH may further improve the anti-tumor effects of this regimen. However, the activity of fludarabine and EPOCH chemotherapy in patients with leukemia is not known. As such, patients with leukemia (AML, myelodysplasia, ALL, and CML) will be candidates for this protocol.

Allogeneic SCT with Th2 Cells: Initial Phase I Results

In this protocol, donor CD4 cells are cultured in vitro to enhance Th2 differentiation and are administered on day 1 post-SCT. In the initial Th2 cohort ($5\times10^6$ cells/kg; n=3), no serious adverse events attributable to the Th2 cells were identified. Acute GVHD grade II (n=2) and grade III (n=1) were observed. As such, there was no apparent decrease in acute GVHD in this first Th2 dose cohort. In the second Th2 dose cohort ($25\times10^6$ cells/kg; n=6), the initial patient entered a pathologic complete remission from refractory bulky lymphoma, but died of DIC and shock at day 22 post-SCT (had grade II clinical GVHD). Subsequent patients at Th2 level #2 engrafted with full donor chimerism without significant toxicity, and appear to have reduced acute GVHD [grade 0 acute GVHD (n=4); liver only acute GVHD grade III (n=1)]. Th2 recipients have had rapid recovery of hematopoiesis, with full donor chimerism; the Th2 cells thus do not appear to impair engraftment. Anti-tumor responses have been observed in refractory malignancy patients, including a molecular CR in a patient with accelerated phase CML. Because this Th2 dose level #2 cohort has achieved alloengraftment with documented anti-tumor responses and limited GVHD (2/6 grade II-IV acute GVHD), this cohort is a candidate for evaluation in the phase II aspect of the protocol.

The Th2 level #3 is about $125\times10^6$ cells/kg; n=6. If the safety and feasibility of dose level #3 is demonstrated in the initial six subjects, 18 additional subjects will be treated with Th2 cells at dose level #3 ($125\times10^6$ cells/kg). In the event that dose level #3 results in more than 1/6 Th2-related adverse events or more than 2/6 cases of grade II to IV acute GVHD, the additional 18 subjects will be treated at the already established Th2 cell dose level #2 ($25\times10^6$ cells/kg). As such, 24 total patients will be treated with a defined dose of Th2 cells, either 25 or $125\times10^6$/kg. The rate and severity of acute GVHD in these Th2 recipients will be compared to the initial protocol cohort that did not receive Th2 cells (12/19 with grade II to III acute GVHD).

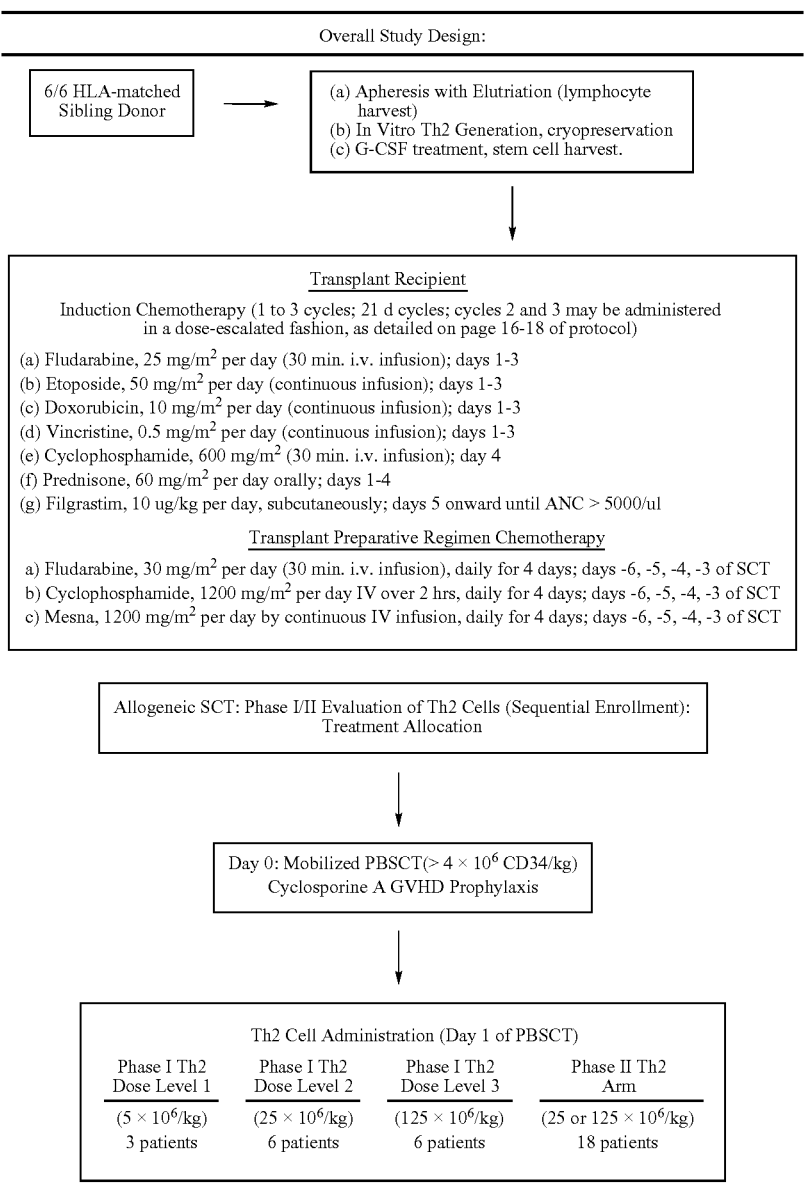

TABLE 2

Variations, modifications, and other implementations of what is described herein will occur to those of ordinary skill in the art without departing from the spirit and scope of the invention as described and claimed herein and such variations, modifications, and implementations are encompassed within the scope of the invention.

All publications mentioned herein are incorporated herein by reference to disclose and describe the methods and/or materials in connection with which the publications are cited.

What is claimed is:

1. A pharmaceutical composition comprising rapamycin resistant Th2 cells that are therapeutically effective, wherein the Th2 cells are selected from T cells cultured in vitro in (i) at least about 0.1 µM rapamycin or a rapamycin derivative and (ii) IL-4.

2. The pharmaceutical composition of claim 1 wherein the composition further comprises a pharmaceutically acceptable carrier.

3. The pharmaceutical composition of claim 1 wherein the composition is packaged together with written instructions for use of the composition to treat an infectious disease, an autoimmune disease and/or Graft Versus Host Disease.

4. The pharmaceutical composition of claim 1 wherein the T cells are cultured in at least 1.0 µM rapamycin or a rapamycin derivative.

5. The pharmaceutical composition of claim 1 wherein the T cells are cultured in at least 10 µM rapamycin or a rapamycin derivative.

6. The pharmaceutical composition of claim 1 wherein the selected rapamycin resistant Th2 cells comprise type II helper T-cell/cytotoxic T cells (Th2/Tc2).

7. The pharmaceutical composition of claim 1 further comprising rapamycin.

8. The pharmaceutical composition of claim 1 wherein the selected Th2 cells are obtained by steps comprising:
co-stimulating isolated T lymphocytes in vitro;
adding cytokines for selecting a T cell subset; and,
expanding the T cell subset in the presence of rapamycin or a rapamycin derivative.

9. Isolated rapamycin resistant Th2 cells selected from T cells cultured in (i) at least about 0.1 µM rapamycin or a rapamycin derivative and (ii) IL-4.

10. The cells of claim 9 wherein the T cells are cultured in at least 1.0 µM rapamycin or a rapamycin derivative.

11. The cells of claim 9 wherein the T cells are cultured in at least 10 µM rapamycin or a rapamycin derivative.

12. Isolated rapamycin resistant Th1 cells selected from T cells cultured in (i) at least about 0.1 µM rapamycin or a rapamycin derivative and (ii) IL-12.

13. The cells of claim 12 wherein the T cells are cultured in at least 1.0 µM rapamycin or a rapamycin derivative.

14. The cells of claim 12 wherein the T cells are cultured in at least 10 µM rapamycin or a rapamycin derivative.

15. A pharmaceutical composition comprising the Th1 cells of claim 12.

16. The pharmaceutical composition of claim 15 wherein the composition further comprises a pharmaceutically acceptable carrier.

17. The pharmaceutical composition of claim 15 wherein the composition is packaged together with written instructions for use of the composition to treat an infectious disease, an autoimmune disease and/or Graft Versus Host Disease.

* * * * *